US008328873B2

(12) United States Patent
Metzger et al.

(10) Patent No.: US 8,328,873 B2
(45) Date of Patent: Dec. 11, 2012

(54) KNEE JOINT PROSTHESIS SYSTEM AND METHOD FOR IMPLANTATION

(75) Inventors: Robert Metzger, Wakarusa, IN (US);
David R. Brown, Warsaw, IN (US);
Brian M. May, Warsaw, IN (US);
Audra Watson, Ft. Wayne, IN (US);
Nathan E. Belcher, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 311 days.

(21) Appl. No.: 12/729,852

(22) Filed: Mar. 23, 2010

(65) Prior Publication Data
US 2010/0174378 A1    Jul. 8, 2010

Related U.S. Application Data

(63) Continuation-in-part of application No. 12/536,056, filed on Aug. 5, 2009, now Pat. No. 8,163,028, which is a continuation-in-part of application No. 11/972,359, filed on Jan. 10, 2008, now Pat. No. 8,157,869, application No. 12/729,852, which is a continuation-in-part of application No. 12/248,517, filed on Oct. 9, 2008, now Pat. No. 8,187,280, which is a continuation-in-part of application No. 11/972,359, application No. 12/729,852, which is a continuation-in-part of application No. 12/248,509, filed on Oct. 9, 2008, which is a continuation-in-part of application No. 11/972,359.

(60) Provisional application No. 60/978,949, filed on Oct. 10, 2007, provisional application No. 60/879,733, filed on Jan. 10, 2007.

(51) Int. Cl.
*A61F 2/38* (2006.01)

(52) U.S. Cl. .................. 623/20.28; 20/20.31; 20/20.32; 20/20.34; 20/20.35

(58) Field of Classification Search ..... 623/20.14–20.36
See application file for complete search history.

(56) References Cited

U.S. PATENT DOCUMENTS
538,987 A     5/1895   Turley
(Continued)

FOREIGN PATENT DOCUMENTS
DE         3336004 A1   6/1985
(Continued)

OTHER PUBLICATIONS

"Advantim® Total Knee System," brochure,1996 (pp. 1-14) Wright Medical Technology, Inc.

(Continued)

*Primary Examiner* — Christopher D Koharski
*Assistant Examiner* — Yashita Sharma
(74) *Attorney, Agent, or Firm* — Harness, Dickey

(57) ABSTRACT

A prosthesis system for replacing a knee joint between a femur and a tibia can include a femoral component, a tibial component, a bearing, a first yoke, and a first key. The femoral component can include a first condylar portion, a second condylar portion, a first sidewall extending superiorly from the first condylar portion, a second sidewall extending superiorly from the second condylar portion where the first and second sidewalls collectively comprise a first hinge portion. The tibial component can have a bone engaging inferior surface and a bearing engaging superior surface. The bearing can have an inferior that engages the bearing engaging surface and a superior femoral engaging surface. The bearing can define an opening. The first yoke can have an inferior portion, a superior portion and a yoke keyway extending through the therethrough.

14 Claims, 25 Drawing Sheets

U.S. PATENT DOCUMENTS

| | | |
|---|---|---|
| 3,806,961 A | 4/1974 | Muller |
| 3,848,272 A | 11/1974 | Noiles |
| 3,859,992 A | 1/1975 | Amstutz |
| 3,878,566 A | 4/1975 | Bechtol |
| 3,964,106 A | 6/1976 | Hutter, Jr. et al. |
| 4,001,897 A | 1/1977 | Rambert et al. |
| 4,007,495 A | 2/1977 | Frazier |
| 4,012,796 A | 3/1977 | Weisman et al. |
| 4,041,550 A | 8/1977 | Frazier |
| 4,064,567 A | 12/1977 | Burstein et al. |
| 4,136,405 A | 1/1979 | Pastrick et al. |
| 4,151,615 A | 5/1979 | Hall |
| 4,202,055 A | 5/1980 | Reiner et al. |
| 4,219,893 A | 9/1980 | Noiles |
| 4,224,698 A | 9/1980 | Hopson |
| 4,284,080 A | 8/1981 | Rehder et al. |
| 4,305,394 A | 12/1981 | Bertuch, Jr. |
| 4,344,192 A | 8/1982 | Imbert et al. |
| 4,404,691 A | 9/1983 | Buning et al. |
| 4,475,549 A | 10/1984 | Oh |
| RE31,865 E | 4/1985 | Roux |
| 4,523,587 A | 6/1985 | Frey |
| 4,549,319 A | 10/1985 | Meyer |
| 4,579,558 A | 4/1986 | Ramer |
| 4,619,658 A | 10/1986 | Pappas et al. |
| 4,624,674 A | 11/1986 | Pappas et al. |
| 4,632,111 A | 12/1986 | Roche |
| 4,655,777 A | 4/1987 | Dunn et al. |
| 4,659,331 A | 4/1987 | Matthews et al. |
| 4,661,112 A | 4/1987 | Muller et al. |
| 4,676,797 A | 6/1987 | Anapliotis et al. |
| 4,676,798 A | 6/1987 | Noiles |
| 4,676,799 A | 6/1987 | Legrand et al. |
| 4,678,470 A | 7/1987 | Nashef et al. |
| 4,698,063 A | 10/1987 | Link et al. |
| 4,711,233 A | 12/1987 | Brown |
| 4,711,639 A | 12/1987 | Grundei |
| 4,714,477 A | 12/1987 | Fichera et al. |
| 4,716,894 A | 1/1988 | Lazzeri et al. |
| 4,718,909 A | 1/1988 | Brown |
| 4,718,911 A | 1/1988 | Kenna |
| 4,718,915 A | 1/1988 | Epinette |
| 4,718,916 A | 1/1988 | Morscher |
| 4,728,333 A | 3/1988 | Masse et al. |
| 4,735,625 A | 4/1988 | Davidson |
| 4,737,411 A | 4/1988 | Graves, Jr. et al. |
| 4,764,171 A | 8/1988 | Harder et al. |
| 4,770,658 A | 9/1988 | Geremakis |
| 4,770,659 A | 9/1988 | Kendall |
| 4,770,660 A | 9/1988 | Averill |
| 4,770,661 A | 9/1988 | Oh |
| 4,778,473 A | 10/1988 | Matthews et al. |
| 4,778,474 A | 10/1988 | Homsy |
| 4,784,662 A | 11/1988 | Muller |
| 4,784,663 A | 11/1988 | Kenna |
| 4,789,663 A | 12/1988 | Wallace et al. |
| 4,790,852 A | 12/1988 | Noiles |
| 4,790,854 A | 12/1988 | Harder et al. |
| 4,795,470 A | 1/1989 | Goymann et al. |
| 4,795,471 A | 1/1989 | Oh |
| 4,798,610 A | 1/1989 | Averill et al. |
| 4,801,301 A | 1/1989 | Noiles |
| 4,813,961 A | 3/1989 | Sostegni |
| 4,822,366 A | 4/1989 | Bolesky |
| 4,827,919 A | 5/1989 | Barbarito et al. |
| 4,828,566 A | 5/1989 | Griss |
| 4,842,606 A | 6/1989 | Kranz et al. |
| 4,846,839 A | 7/1989 | Noiles |
| 4,846,840 A | 7/1989 | Leclercq et al. |
| 4,851,007 A | 7/1989 | Gray |
| 4,871,368 A | 10/1989 | Wagner |
| 4,878,916 A | 11/1989 | Rhenter et al. |
| 4,883,488 A | 11/1989 | Bloebaum et al. |
| 4,883,492 A | 11/1989 | Frey et al. |
| 4,888,021 A | 12/1989 | Forte et al. |
| 4,892,547 A | 1/1990 | Brown |
| 4,904,265 A | 2/1990 | MacCollum et al. |
| 4,908,033 A | 3/1990 | Frey et al. |
| 4,908,034 A | 3/1990 | Weightman et al. |
| 4,908,036 A | 3/1990 | Link et al. |
| 4,911,723 A | 3/1990 | Menschik |
| 4,919,674 A | 4/1990 | Schelhas |
| 4,923,472 A | 5/1990 | Ugolini |
| 4,936,847 A | 6/1990 | Manginelli |
| 4,936,853 A | 6/1990 | Fabian et al. |
| 4,936,855 A | 6/1990 | Sherman |
| 4,936,861 A | 6/1990 | Muller et al. |
| 4,938,769 A | 7/1990 | Shaw |
| 4,938,772 A | 7/1990 | Frey et al. |
| 4,944,756 A | 7/1990 | Kenna |
| 4,944,757 A | 7/1990 | Martinez et al. |
| 4,950,297 A | 8/1990 | Elloy et al. |
| 4,950,298 A | 8/1990 | Gustilo et al. |
| 4,950,299 A | 8/1990 | Noiles |
| 4,959,071 A | 9/1990 | Brown et al. |
| 4,960,427 A | 10/1990 | Noiles |
| 4,961,748 A | 10/1990 | Frey et al. |
| 4,963,154 A | 10/1990 | Anapliotis et al. |
| 4,963,155 A | 10/1990 | Lazzeri et al. |
| 4,964,869 A | 10/1990 | Auclair et al. |
| 4,978,356 A | 12/1990 | Noiles |
| 4,985,037 A | 1/1991 | Petersen |
| 4,990,161 A | 2/1991 | Kampner |
| 4,994,064 A | 2/1991 | Aboczky |
| 4,995,158 A | 2/1991 | Howell et al. |
| 4,995,883 A | 2/1991 | Demane et al. |
| 5,002,578 A | 3/1991 | Luman |
| 5,002,581 A | 3/1991 | Paxson et al. |
| 5,009,666 A | 4/1991 | Van Syckle et al. |
| 5,019,103 A | 5/1991 | Van Zile et al. |
| 5,019,105 A | 5/1991 | Wiley |
| 5,019,108 A | 5/1991 | Bertin et al. |
| 5,021,062 A | 6/1991 | Adrey et al. |
| 5,030,221 A | 7/1991 | Buechel et al. |
| 5,032,134 A | 7/1991 | Lindwer |
| 5,037,424 A | 8/1991 | Aboczky |
| 5,037,438 A | 8/1991 | Davidson |
| 5,037,441 A | 8/1991 | Bouvet |
| 5,041,140 A | 8/1991 | Teinturier |
| 5,061,269 A | 10/1991 | Muller |
| 5,061,270 A | 10/1991 | Aboczky |
| 5,062,852 A | 11/1991 | Dorr et al. |
| 5,062,853 A | 11/1991 | Forte |
| 5,074,879 A | 12/1991 | Pappas et al. |
| 5,080,677 A | 1/1992 | Shelley |
| 5,084,051 A | 1/1992 | Tormala et al. |
| 5,092,900 A | 3/1992 | Marchetti et al. |
| 5,098,437 A | 3/1992 | Kashuba et al. |
| 5,108,437 A | 4/1992 | Kenna |
| 5,108,439 A | 4/1992 | Morscher et al. |
| 5,108,445 A | 4/1992 | Ashby |
| 5,108,446 A | 4/1992 | Wagner et al. |
| 5,108,450 A | 4/1992 | Horber et al. |
| 5,112,338 A | 5/1992 | Anspach, III |
| 5,116,339 A | 5/1992 | Glock |
| 5,116,378 A | 5/1992 | Carbone |
| 5,116,379 A | 5/1992 | McLardy-Smith |
| 5,116,380 A | 5/1992 | Hewka et al. |
| 5,133,760 A | 7/1992 | Petersen et al. |
| 5,133,763 A | 7/1992 | Mullers |
| 5,137,535 A | 8/1992 | Keller |
| 5,137,536 A | 8/1992 | Koshino |
| 5,141,512 A | 8/1992 | Farmer et al. |
| 5,147,406 A | 9/1992 | Houston et al. |
| 5,152,796 A | 10/1992 | Slamin |
| 5,152,797 A | 10/1992 | Luckman et al. |
| 5,163,963 A | 11/1992 | Hewka et al. |
| 5,163,966 A | 11/1992 | Norton et al. |
| 5,169,399 A | 12/1992 | Ryland et al. |
| 5,171,243 A | 12/1992 | Kashuba et al. |
| 5,171,276 A | 12/1992 | Caspari et al. |
| 5,171,286 A | 12/1992 | Lawes et al. |
| 5,171,313 A | 12/1992 | Salyer |
| 5,171,323 A | 12/1992 | Willert et al. |
| 5,176,709 A | 1/1993 | Branemark |
| 5,180,394 A | 1/1993 | Davidson |
| 5,181,925 A | 1/1993 | Houston et al. |

| Patent | Date | Name |
|---|---|---|
| 5,181,929 A | 1/1993 | Prats et al. |
| 5,192,331 A | 3/1993 | Spotorno et al. |
| 5,194,066 A | 3/1993 | Van Zile |
| 5,197,488 A | 3/1993 | Kovacevic |
| 5,197,987 A | 3/1993 | Koch et al. |
| 5,197,988 A | 3/1993 | Spotorno et al. |
| 5,201,769 A | 4/1993 | Schutzer |
| 5,211,664 A | 5/1993 | Tepic et al. |
| 5,211,666 A | 5/1993 | Fetto |
| 5,217,496 A | 6/1993 | Bruce et al. |
| 5,217,498 A | 6/1993 | Henssge et al. |
| 5,219,362 A | 6/1993 | Tuke et al. |
| 5,222,983 A | 6/1993 | Schmitz et al. |
| 5,222,984 A | 6/1993 | Forte |
| 5,226,915 A | 7/1993 | Bertin |
| 5,242,445 A | 9/1993 | Ashman |
| 5,246,459 A | 9/1993 | Elias |
| 5,250,051 A | 10/1993 | Maryan |
| 5,258,034 A | 11/1993 | Furlong et al. |
| 5,258,035 A | 11/1993 | Hofmann et al. |
| 5,263,988 A | 11/1993 | Huebner |
| 5,275,601 A | 1/1994 | Gogolewski et al. |
| 5,282,867 A | 2/1994 | Mikhail |
| 5,282,870 A | 2/1994 | Moser et al. |
| 5,284,483 A | 2/1994 | Johnson et al. |
| 5,290,311 A | 3/1994 | Baumann |
| 5,290,313 A | 3/1994 | Heldreth |
| 5,290,315 A | 3/1994 | DeCarlo, Jr. |
| 5,290,318 A | 3/1994 | Ling et al. |
| 5,292,322 A | 3/1994 | Faccioli et al. |
| 5,314,478 A | 5/1994 | Oka et al. |
| 5,314,479 A | 5/1994 | Rockwood, Jr. et al. |
| 5,314,491 A | 5/1994 | Thongpreda et al. |
| 5,318,571 A | 6/1994 | Benson |
| 5,320,625 A | 6/1994 | Bertin |
| 5,326,358 A | 7/1994 | Aubriot et al. |
| 5,326,359 A | 7/1994 | Oudard |
| 5,330,534 A | 7/1994 | Herrington et al. |
| 5,336,267 A | 8/1994 | Kubein-Meesenburg et al. |
| 5,342,360 A | 8/1994 | Faccioli et al. |
| 5,343,877 A | 9/1994 | Park |
| 5,344,460 A | 9/1994 | Turanyi et al. |
| 5,344,461 A | 9/1994 | Phlipot |
| 5,356,629 A | 10/1994 | Sander et al. |
| 5,358,529 A | 10/1994 | Davidson |
| 5,358,530 A | 10/1994 | Hodorek |
| 5,360,449 A | 11/1994 | Branemark |
| 5,360,451 A | 11/1994 | Keller |
| 5,364,403 A | 11/1994 | Petersen et al. |
| 5,370,692 A | 12/1994 | Fink et al. |
| 5,370,693 A | 12/1994 | Kelman et al. |
| 5,370,698 A | 12/1994 | Heimke et al. |
| 5,370,701 A | 12/1994 | Finn |
| 5,370,702 A | 12/1994 | Jones |
| 5,376,122 A | 12/1994 | Pappas et al. |
| 5,376,123 A | 12/1994 | Klaue et al. |
| 5,376,124 A | 12/1994 | Gustke et al. |
| 5,383,938 A | 1/1995 | Rohr et al. |
| 5,387,239 A | 2/1995 | Bianco et al. |
| 5,387,240 A | 2/1995 | Pottenger et al. |
| 5,387,241 A | 2/1995 | Hayes |
| 5,397,360 A | 3/1995 | Cohen et al. |
| 5,405,392 A | 4/1995 | Deckner |
| 5,405,395 A | 4/1995 | Coates |
| 5,405,400 A | 4/1995 | Linscheid et al. |
| 5,405,401 A | 4/1995 | Lippincott, III et al. |
| 5,405,403 A | 4/1995 | Mikhail |
| 5,405,404 A | 4/1995 | Gardner et al. |
| 5,411,555 A | 5/1995 | Nieder |
| 5,413,605 A | 5/1995 | Ashby et al. |
| 5,413,607 A | 5/1995 | Engelbrecht et al. |
| 5,413,610 A | 5/1995 | Amino et al. |
| 5,417,696 A | 5/1995 | Kashuba et al. |
| 5,425,778 A | 6/1995 | Zichner et al. |
| 5,425,779 A | 6/1995 | Schlosser et al. |
| 5,431,657 A | 7/1995 | Rohr |
| 5,443,512 A | 8/1995 | Parr et al. |
| 5,443,516 A | 8/1995 | Albrektsson et al. |
| 5,447,492 A | 9/1995 | Cartmell et al. |
| 5,458,637 A | 10/1995 | Hayes |
| 5,462,563 A | 10/1995 | Shearer et al. |
| 5,474,560 A | 12/1995 | Rohr, Jr. |
| 5,480,443 A | 1/1996 | Elias |
| 5,480,444 A | 1/1996 | Incavo et al. |
| 5,480,445 A | 1/1996 | Burkinshaw |
| 5,480,446 A | 1/1996 | Goodfellow et al. |
| 5,480,447 A | 1/1996 | Skiba |
| 5,480,448 A | 1/1996 | Mikhail |
| 5,480,451 A | 1/1996 | Grundei et al. |
| 5,480,452 A | 1/1996 | Hofmann et al. |
| 5,486,178 A | 1/1996 | Hodge |
| 5,486,181 A | 1/1996 | Cohen et al. |
| 5,489,311 A | 2/1996 | Cipolletti |
| 5,507,745 A | 4/1996 | Logroscino et al. |
| 5,507,817 A | 4/1996 | Craig et al. |
| 5,507,818 A | 4/1996 | McLaughlin |
| 5,507,820 A | 4/1996 | Pappas |
| 5,507,826 A | 4/1996 | Besselink et al. |
| 5,507,829 A | 4/1996 | Thongpreda et al. |
| 5,507,832 A | 4/1996 | Michielli et al. |
| 5,510,396 A | 4/1996 | Prewett et al. |
| 5,522,902 A | 6/1996 | Yuan et al. |
| 5,527,317 A | 6/1996 | Ashby et al. |
| 5,531,791 A | 7/1996 | Wolfinbarger, Jr. |
| 5,531,793 A | 7/1996 | Kelman et al. |
| 5,534,032 A | 7/1996 | Hodorek |
| 5,540,697 A | 7/1996 | Rehmann et al. |
| 5,549,684 A | 8/1996 | Amino et al. |
| 5,549,685 A | 8/1996 | Hayes |
| 5,549,689 A | 8/1996 | Epstein et al. |
| 5,549,696 A | 8/1996 | Willi |
| 5,549,699 A | 8/1996 | MacMahon et al. |
| 5,549,701 A | 8/1996 | Mikhail |
| 5,549,703 A | 8/1996 | Daigle et al. |
| 5,549,704 A | 8/1996 | Sutter |
| 5,549,706 A | 8/1996 | McCarthy |
| 5,552,454 A | 9/1996 | Kretschmann et al. |
| 5,556,432 A | 9/1996 | Kubein-Meesenburg et al. |
| 5,556,433 A | 9/1996 | Gabriel et al. |
| 5,571,111 A | 11/1996 | Aboczky |
| 5,571,193 A | 11/1996 | Kampner |
| 5,571,194 A | 11/1996 | Gabriel |
| 5,571,196 A | 11/1996 | Stein |
| 5,571,201 A | 11/1996 | Averill et al. |
| 5,571,202 A | 11/1996 | Mathys, Sr. et al. |
| 5,580,352 A | 12/1996 | Sekel |
| 5,584,837 A | 12/1996 | Petersen |
| 5,593,447 A | 1/1997 | Angeli |
| 5,593,449 A | 1/1997 | Roberson, Jr. |
| 5,593,450 A | 1/1997 | Scott et al. |
| 5,593,451 A | 1/1997 | Averill et al. |
| 5,609,641 A | 3/1997 | Johnson et al. |
| 5,609,642 A | 3/1997 | Johnson et al. |
| 5,609,645 A | 3/1997 | Vinciguerra |
| 5,609,647 A | 3/1997 | K alberer et al. |
| 5,609,648 A | 3/1997 | Oehy et al. |
| 5,624,444 A | 4/1997 | Wixon et al. |
| 5,639,280 A | 6/1997 | Warner et al. |
| 5,641,323 A | 6/1997 | Caldarise |
| 5,645,593 A | 7/1997 | Woods et al. |
| 5,645,594 A | 7/1997 | Devanathan et al. |
| 5,645,604 A | 7/1997 | Schneider et al. |
| 5,653,765 A | 8/1997 | McTighe et al. |
| 5,658,294 A | 8/1997 | Sederholm |
| 5,658,344 A | 8/1997 | Hurlburt |
| 5,658,346 A | 8/1997 | Willi |
| 5,658,348 A | 8/1997 | Rohr, Jr. |
| 5,658,349 A | 8/1997 | Brooks et al. |
| 5,662,656 A | 9/1997 | White |
| 5,676,700 A | 10/1997 | Black et al. |
| 5,676,704 A | 10/1997 | Ries et al. |
| 5,681,354 A | 10/1997 | Eckhoff |
| 5,683,399 A | 11/1997 | Jones |
| 5,683,472 A | 11/1997 | O'Neil et al. |
| 5,702,463 A | 12/1997 | Pothier et al. |
| 5,702,475 A | 12/1997 | Zahedi |
| 5,702,476 A | 12/1997 | Limacher et al. |
| 5,702,477 A | 12/1997 | Capello et al. |

| | | | | | |
|---|---|---|---|---|---|
| 5,702,478 A | 12/1997 | Tornier | 5,972,368 A | 10/1999 | McKay |
| 5,702,482 A | 12/1997 | Thongpreda et al. | 5,973,222 A | 10/1999 | Devanathan et al. |
| 5,702,487 A | 12/1997 | Averill et al. | 5,976,148 A | 11/1999 | Charpenet et al. |
| 5,720,752 A | 2/1998 | Elliott et al. | 5,976,188 A | 11/1999 | Dextradeur et al. |
| 5,725,589 A | 3/1998 | Pfaff et al. | 5,976,189 A | 11/1999 | Keller |
| 5,725,591 A | 3/1998 | DeCarlo, Jr. et al. | 5,977,204 A | 11/1999 | Boyan et al. |
| 5,725,597 A | 3/1998 | Hwang | 5,980,574 A | 11/1999 | Takei et al. |
| 5,735,901 A | 4/1998 | Maumy et al. | 5,984,968 A | 11/1999 | Park |
| 5,746,771 A | 5/1998 | Clement, Jr. et al. | 5,984,969 A | 11/1999 | Matthews et al. |
| 5,749,877 A | 5/1998 | Young | 5,989,293 A | 11/1999 | Cook et al. |
| 5,755,794 A | 5/1998 | Benson | 5,989,294 A | 11/1999 | Marlow |
| 5,755,800 A | 5/1998 | O'Neil et al. | 5,997,576 A | 12/1999 | Copf |
| 5,755,805 A | 5/1998 | Whiteside | 5,997,577 A | 12/1999 | Herrington et al. |
| 5,755,806 A | 5/1998 | Stalcup et al. | 5,997,579 A | 12/1999 | Albrektsson et al. |
| 5,755,807 A | 5/1998 | Anstaett et al. | 6,004,353 A | 12/1999 | Masini |
| 5,755,808 A | 5/1998 | DeCarlo et al. | 6,005,018 A | 12/1999 | Cicierega et al. |
| 5,766,255 A | 6/1998 | Slamin et al. | 6,007,580 A | 12/1999 | Lehto et al. |
| 5,766,256 A | 6/1998 | Oudard et al. | 6,008,432 A | 12/1999 | Taylor |
| 5,766,260 A | 6/1998 | Whiteside | 6,010,533 A | 1/2000 | Pope et al. |
| 5,766,262 A | 6/1998 | Mikhail | 6,010,534 A | 1/2000 | O'Neil et al. |
| 5,776,200 A | 7/1998 | Johnson et al. | 6,013,080 A | 1/2000 | Khalili |
| 5,776,201 A | 7/1998 | Colleran et al. | 6,013,081 A | 1/2000 | Burkinshaw et al. |
| 5,776,202 A | 7/1998 | Copf et al. | 6,013,103 A | 1/2000 | Kaufman et al. |
| 5,782,920 A | 7/1998 | Colleran | 6,013,104 A | 1/2000 | Kampner |
| 5,782,921 A | 7/1998 | Colleran et al. | 6,015,937 A | 1/2000 | Br.ang.nemark |
| 5,782,924 A | 7/1998 | Johnson | 6,027,505 A | 2/2000 | Peter et al. |
| 5,782,925 A | 7/1998 | Collazo et al. | 6,039,764 A | 3/2000 | Pottenger et al. |
| 5,782,928 A | 7/1998 | Ries et al. | 6,042,611 A | 3/2000 | Noiles |
| 5,782,930 A | 7/1998 | Lin et al. | 6,045,583 A | 4/2000 | Gross et al. |
| 5,788,976 A | 8/1998 | Bradford | 6,053,945 A | 4/2000 | O'Neil et al. |
| 5,798,924 A | 8/1998 | Eufinger et al. | 6,056,779 A | 5/2000 | Noyer et al. |
| 5,800,554 A | 9/1998 | Scholz | 6,059,833 A | 5/2000 | Doets |
| 5,800,555 A | 9/1998 | Gray, III | 6,063,091 A | 5/2000 | Lombardo et al. |
| 5,800,556 A | 9/1998 | Sanders et al. | 6,063,124 A | 5/2000 | Amstutz |
| 5,800,558 A | 9/1998 | LaHaise, Sr. | 6,066,176 A | 5/2000 | Oshida |
| 5,800,560 A | 9/1998 | Draenert | 6,071,311 A | 6/2000 | O'Neil et al. |
| 5,817,096 A | 10/1998 | Salyer | 6,074,424 A | 6/2000 | Perrone, Jr. et al. |
| 5,824,097 A | 10/1998 | Gabriel et al. | 6,074,425 A | 6/2000 | Pappas |
| 5,824,107 A | 10/1998 | Tschirren | 6,080,195 A | 6/2000 | Colleran et al. |
| 5,824,108 A | 10/1998 | Huebner | 6,086,614 A | 7/2000 | Mumme |
| 5,830,215 A | 11/1998 | Incavo et al. | 6,087,553 A | 7/2000 | Cohen et al. |
| 5,858,020 A | 1/1999 | Johnson et al. | 6,090,146 A | 7/2000 | Rozow, III et al. |
| 5,865,850 A | 2/1999 | Matthews | 6,093,208 A | 7/2000 | Tian |
| 5,871,547 A | 2/1999 | Abouaf et al. | 6,096,082 A | 8/2000 | Stegmuller et al. |
| 5,871,548 A | 2/1999 | Sanders et al. | 6,099,569 A | 8/2000 | Keller |
| 5,876,459 A | 3/1999 | Powell | 6,099,571 A | 8/2000 | Knapp |
| 5,879,387 A | 3/1999 | Jones et al. | 6,113,640 A | 9/2000 | Tormala et al. |
| 5,879,390 A | 3/1999 | Kubein-Meesenburg et al. | 6,117,175 A | 9/2000 | Bosredon |
| 5,879,391 A | 3/1999 | Slamin | 6,120,543 A | 9/2000 | Kubein-Meesenburg et al. |
| 5,879,398 A | 3/1999 | Swarts et al. | 6,120,545 A | 9/2000 | Hamelijnck et al. |
| 5,879,401 A | 3/1999 | Besemer et al. | 6,126,690 A | 10/2000 | Ateshian et al. |
| 5,879,402 A | 3/1999 | Lawes et al. | 6,126,691 A | 10/2000 | Kasra et al. |
| 5,879,404 A | 3/1999 | Bateman et al. | 6,126,692 A | 10/2000 | Robie et al. |
| 5,879,405 A | 3/1999 | Ries et al. | 6,126,693 A | 10/2000 | O'Neil et al. |
| 5,879,406 A | 3/1999 | Lilley | 6,126,694 A | 10/2000 | Gray, Jr. |
| 5,888,205 A | 3/1999 | Pratt et al. | 6,126,695 A | 10/2000 | Semlitsch |
| 5,888,206 A | 3/1999 | Lob et al. | 6,129,765 A | 10/2000 | Lopez et al. |
| 5,888,211 A | 3/1999 | Sanders | 6,132,468 A | 10/2000 | Mansmann |
| 5,899,942 A | 5/1999 | Berman | 6,132,469 A | 10/2000 | Schroeder |
| 5,902,340 A | 5/1999 | White et al. | 6,136,029 A | 10/2000 | Johnson et al. |
| 5,904,688 A | 5/1999 | Gilbert et al. | 6,136,033 A | 10/2000 | Suemer |
| 5,904,720 A | 5/1999 | Farrar et al. | 6,136,035 A | 10/2000 | Lob et al. |
| 5,906,644 A | 5/1999 | Powell | 6,139,584 A | 10/2000 | Ochoa et al. |
| 5,910,172 A | 6/1999 | Penenberg | 6,142,998 A | 11/2000 | Smith et al. |
| 5,916,269 A | 6/1999 | Serbousek et al. | 6,146,424 A | 11/2000 | Gray, Jr. et al. |
| 5,916,270 A | 6/1999 | Lipman | 6,149,687 A | 11/2000 | Gray, Jr. et al. |
| 5,919,236 A | 7/1999 | Pfaff et al. | 6,152,930 A | 11/2000 | Mastrorio |
| 5,928,286 A | 7/1999 | Ashby et al. | 6,152,961 A | 11/2000 | Ostiguy, Jr. et al. |
| 5,928,287 A | 7/1999 | Keller | 6,156,070 A | 12/2000 | Incavo et al. |
| 5,931,870 A | 8/1999 | Cuckler et al. | 6,162,255 A | 12/2000 | Oyola |
| 5,935,171 A | 8/1999 | Schneider et al. | 6,162,256 A | 12/2000 | Ostiguy, Jr. et al. |
| 5,935,175 A | 8/1999 | Ostiguy, Jr. et al. | 6,165,220 A | 12/2000 | McKellop et al. |
| 5,938,702 A | 8/1999 | Lopez et al. | 6,165,222 A | 12/2000 | Hoeppner et al. |
| 5,944,756 A | 8/1999 | Fischetti et al. | 6,165,223 A | 12/2000 | Metzger et al. |
| 5,944,759 A | 8/1999 | Link | 6,168,600 B1 | 1/2001 | Grace et al. |
| 5,951,603 A | 9/1999 | O'Neil et al. | 6,171,342 B1 | 1/2001 | O'Neil et al. |
| 5,954,727 A | 9/1999 | Collazo | 6,179,876 B1 | 1/2001 | Stamper et al. |
| 5,957,979 A | 9/1999 | Beckman et al. | 6,179,877 B1 | 1/2001 | Burke |
| 5,961,516 A | 10/1999 | Graf | 6,193,759 B1 | 2/2001 | Ro et al. |

| Patent No. | Date | Inventor |
|---|---|---|
| 6,197,032 B1 | 3/2001 | Lawes et al. |
| 6,200,324 B1 | 3/2001 | Regni, Jr. |
| 6,206,929 B1 | 3/2001 | Ochoa et al. |
| 6,214,014 B1 | 4/2001 | McGann |
| 6,214,052 B1 | 4/2001 | Burkinshaw |
| 6,214,053 B1 | 4/2001 | Ling et al. |
| 6,217,615 B1 | 4/2001 | Sioshansi et al. |
| 6,217,619 B1 | 4/2001 | Keller |
| 6,221,110 B1 | 4/2001 | Copf |
| 6,224,633 B1 | 5/2001 | Kalberer et al. |
| 6,228,091 B1 | 5/2001 | Lombardo et al. |
| 6,228,121 B1 | 5/2001 | Khalili |
| 6,231,611 B1 | 5/2001 | Mosseri |
| 6,235,060 B1 | 5/2001 | Kubein-Meesenburg et al. |
| 6,245,111 B1 | 6/2001 | Shaffner |
| 6,248,132 B1 | 6/2001 | Harris |
| 6,264,698 B1 | 7/2001 | Lawes et al. |
| 6,264,699 B1 | 7/2001 | Noiles et al. |
| 6,267,785 B1 | 7/2001 | Masini |
| 6,281,264 B1 | 8/2001 | Salovey et al. |
| 6,284,001 B1 | 9/2001 | Knapp |
| 6,290,725 B1 | 9/2001 | Weiss et al. |
| 6,290,726 B1 | 9/2001 | Pope et al. |
| 6,290,727 B1 | 9/2001 | Otto et al. |
| 6,293,971 B1 | 9/2001 | Nelson et al. |
| 6,296,667 B1 | 10/2001 | Johnson et al. |
| 6,302,890 B1 | 10/2001 | Leone, Jr. |
| 6,306,172 B1 | 10/2001 | O'Neil et al. |
| 6,319,285 B1 | 11/2001 | Chamier et al. |
| 6,325,829 B1 | 12/2001 | Schmotzer |
| 6,334,875 B1 | 1/2002 | Keller |
| 6,340,370 B1 | 1/2002 | Willert et al. |
| 6,342,075 B1 | 1/2002 | MacArthur |
| 6,344,060 B1 | 2/2002 | Schmotzer et al. |
| 6,344,496 B1 | 2/2002 | Niederauer et al. |
| 6,352,559 B1 | 3/2002 | Church |
| 6,358,282 B1 | 3/2002 | Wymann |
| 6,361,566 B1 | 3/2002 | Al-Hafez |
| 6,368,354 B2 | 4/2002 | Burstein et al. |
| 6,376,573 B1 | 4/2002 | White et al. |
| 6,379,389 B1 | 4/2002 | Koch |
| 6,383,227 B1 | 5/2002 | Baroud et al. |
| 6,387,131 B1 | 5/2002 | Miehlke et al. |
| 6,391,251 B1 | 5/2002 | Keicher et al. |
| 6,413,279 B1 | 7/2002 | Metzger et al. |
| 6,413,280 B1 | 7/2002 | Feiler |
| 6,416,552 B1 | 7/2002 | Hoeppner et al. |
| 6,423,096 B1 | 7/2002 | Musset et al. |
| 6,425,921 B1 | 7/2002 | Grundei et al. |
| 6,428,578 B2 | 8/2002 | White |
| 6,432,141 B1 | 8/2002 | Stocks et al. |
| 6,436,145 B1 | 8/2002 | Miller |
| 6,436,146 B1 | 8/2002 | Hassler et al. |
| 6,447,549 B1 | 9/2002 | Taft |
| 6,447,550 B1 | 9/2002 | Hunter et al. |
| 6,451,058 B2 | 9/2002 | Tuke et al. |
| 6,468,281 B1 | 10/2002 | Badorf et al. |
| 6,475,243 B1 | 11/2002 | Sheldon et al. |
| 6,482,237 B2 | 11/2002 | Mosseri |
| 6,485,519 B2 | 11/2002 | Meyers et al. |
| 6,488,713 B1 | 12/2002 | Hershberger |
| 6,488,715 B1 | 12/2002 | Pope et al. |
| 6,491,726 B2 | 12/2002 | Pappas |
| 6,494,914 B2 | 12/2002 | Brown et al. |
| 6,497,728 B2 | 12/2002 | Yong |
| 6,500,207 B1 | 12/2002 | Keller |
| 6,500,208 B1 | 12/2002 | Metzger et al. |
| 6,503,281 B1 | 1/2003 | Mallory |
| 6,506,215 B1 | 1/2003 | Letot et al. |
| 6,517,583 B1 | 2/2003 | Pope et al. |
| 6,518,328 B2 | 2/2003 | Kumar |
| 6,520,995 B2 | 2/2003 | Church |
| 6,524,344 B2 | 2/2003 | Yoon |
| 6,524,345 B1 | 2/2003 | Valimaa et al. |
| 6,527,807 B1 | 3/2003 | O'Neil et al. |
| 6,527,808 B1 | 3/2003 | Albertorio et al. |
| 6,527,809 B1 | 3/2003 | Doursounian et al. |
| 6,527,810 B2 | 3/2003 | Johnson et al. |
| 6,537,321 B1 | 3/2003 | Horber |
| 6,540,786 B2 | 4/2003 | Chibrac et al. |
| 6,558,427 B2 | 5/2003 | Leclercq et al. |
| 6,565,575 B2 | 5/2003 | Lewis |
| 6,565,606 B1 | 5/2003 | Bruce et al. |
| 6,589,248 B1 | 7/2003 | Hughes |
| 6,589,283 B1 | 7/2003 | Metzger et al. |
| 6,589,284 B1 | 7/2003 | Silberer |
| 6,602,259 B1 | 8/2003 | Masini |
| 6,605,293 B1 | 8/2003 | Giordano et al. |
| 6,610,097 B2 | 8/2003 | Serbousek et al. |
| 6,613,092 B1 | 9/2003 | Kana et al. |
| 6,616,696 B1 | 9/2003 | Merchant |
| 6,620,198 B2 | 9/2003 | Burstein et al. |
| 6,623,488 B1 | 9/2003 | Leone, Jr. |
| 6,626,950 B2 | 9/2003 | Brown et al. |
| 6,629,999 B1 | 10/2003 | Serafin, Jr. |
| 6,641,617 B1 | 11/2003 | Merrill et al. |
| 6,652,533 B2 | 11/2003 | O'Neil |
| 6,652,586 B2 | 11/2003 | Hunter et al. |
| 6,652,589 B2 | 11/2003 | Schmotzer et al. |
| 6,652,590 B2 | 11/2003 | Zitnansky et al. |
| 6,660,040 B2 | 12/2003 | Chan et al. |
| 6,669,728 B2 | 12/2003 | Despres, III et al. |
| 6,679,890 B2 | 1/2004 | Margulies et al. |
| 6,682,566 B2 | 1/2004 | Draenert |
| 6,682,567 B1 | 1/2004 | Schroeder |
| 6,682,568 B2 | 1/2004 | Despres, III et al. |
| 6,692,531 B1 | 2/2004 | Yoon et al. |
| 6,699,293 B2 | 3/2004 | White |
| 6,706,071 B1 | 3/2004 | Wolter |
| 6,706,072 B2 | 3/2004 | Dwyer et al. |
| 6,712,857 B1 | 3/2004 | Roger |
| 6,712,858 B1 | 3/2004 | Grundei et al. |
| 6,716,248 B2 | 4/2004 | Huene |
| 6,719,800 B2 | 4/2004 | Meyers et al. |
| 6,723,129 B2 | 4/2004 | Dwyer et al. |
| 6,726,725 B2 | 4/2004 | Hunter et al. |
| 6,740,092 B2 | 5/2004 | Lombardo et al. |
| 6,743,258 B1 | 6/2004 | Keller |
| 6,755,864 B1 | 6/2004 | Brack et al. |
| 6,758,864 B2 | 7/2004 | Storer et al. |
| 6,761,741 B2 | 7/2004 | Iesaka |
| 6,764,516 B2 | 7/2004 | Pappas |
| 6,770,097 B2 | 8/2004 | Leclercq |
| 6,773,461 B2 | 8/2004 | Meyers et al. |
| 6,783,550 B2 | 8/2004 | MacArthur |
| 6,786,933 B2 | 9/2004 | Merrill et al. |
| 6,793,681 B1 | 9/2004 | Pope et al. |
| 6,800,670 B2 | 10/2004 | Shen et al. |
| 6,802,866 B2 | 10/2004 | Bunz |
| 6,811,568 B2 | 11/2004 | Minamikawa |
| 6,811,569 B1 | 11/2004 | Afriat et al. |
| 6,818,019 B2 | 11/2004 | Horber |
| 6,818,020 B2 | 11/2004 | Sun et al. |
| 6,827,739 B2 | 12/2004 | Griner et al. |
| 6,827,742 B2 | 12/2004 | Hayes, Jr. et al. |
| 6,840,944 B2 | 1/2005 | Suddaby |
| 6,843,805 B2 | 1/2005 | Webb et al. |
| 6,843,806 B2 | 1/2005 | Hayes, Jr. et al. |
| 6,863,692 B2 | 3/2005 | Meulink |
| 6,866,683 B2 | 3/2005 | Gerbec et al. |
| 6,866,685 B2 | 3/2005 | Chan et al. |
| 6,869,447 B2 | 3/2005 | Lee et al. |
| 6,875,237 B2 | 4/2005 | Dye |
| 6,881,229 B2 | 4/2005 | Khandkar et al. |
| 6,887,276 B2 | 5/2005 | Gerbec et al. |
| 6,896,702 B2 | 5/2005 | Collazo |
| 6,905,515 B1 | 6/2005 | Gilbertson |
| 6,908,486 B2 | 6/2005 | Lewallen |
| 6,916,340 B2 | 7/2005 | Metzger et al. |
| 6,916,341 B2 | 7/2005 | Rolston |
| 6,923,833 B2 | 8/2005 | Wasielewski |
| 6,926,738 B2 | 8/2005 | Wyss |
| 6,926,739 B1 | 8/2005 | O'Connor et al. |
| 6,926,740 B2 | 8/2005 | Lewis et al. |
| 6,944,518 B2 | 9/2005 | Roose |
| 6,953,479 B2 | 10/2005 | Carson et al. |
| 6,962,607 B2 | 11/2005 | Gundlapalli et al. |
| 6,966,932 B1 | 11/2005 | Schroeder |

| | | | |
|---|---|---|---|
| 6,969,406 B2 | 11/2005 | Tornier | |
| 6,972,021 B2 | 12/2005 | Raugel | |
| 6,972,039 B2 | 12/2005 | Metzger et al. | |
| 6,981,991 B2 | 1/2006 | Ferree | |
| 6,986,791 B1 | 1/2006 | Metzger | |
| 7,004,946 B2 | 2/2006 | Parker et al. | |
| 7,022,142 B2 | 4/2006 | Johnson | |
| 7,025,788 B2 | 4/2006 | Metzger et al. | |
| 7,037,310 B2 | 5/2006 | Murphy | |
| 7,044,974 B2 | 5/2006 | Garber et al. | |
| 7,051,417 B2 | 5/2006 | Michelson | |
| 7,056,577 B1 | 6/2006 | Bruce et al. | |
| 7,070,622 B1 | 7/2006 | Brown et al. | |
| 7,074,241 B2 | 7/2006 | McKinnon | |
| 7,105,026 B2 | 9/2006 | Johnson et al. | |
| 7,108,719 B2 | 9/2006 | Horber | |
| 7,125,193 B2 | 10/2006 | Despres, III et al. | |
| 7,131,995 B2 | 11/2006 | Biedermann et al. | |
| 7,153,326 B1 | 12/2006 | Metzger | |
| 7,156,880 B2 | 1/2007 | Evans et al. | |
| 7,166,133 B2 | 1/2007 | Evans et al. | |
| 7,179,295 B2 | 2/2007 | Kovacevic | |
| 7,189,263 B2 | 3/2007 | Erbe et al. | |
| 7,192,448 B2 | 3/2007 | Ferree | |
| 7,198,642 B2 | 4/2007 | Hazebrouck et al. | |
| 7,445,639 B2 | 11/2008 | Metzger et al. | |
| 7,497,874 B1 | 3/2009 | Metzger et al. | |
| 2001/0014828 A1 | 8/2001 | Yoon | |
| 2001/0014829 A1 | 8/2001 | Yoon | |
| 2001/0016780 A1 | 8/2001 | Yong San | |
| 2001/0018616 A1 | 8/2001 | Schwab | |
| 2001/0032021 A1 | 10/2001 | McKinnon | |
| 2001/0037156 A1 | 11/2001 | Burstein et al. | |
| 2001/0039456 A1 | 11/2001 | Boyer et al. | |
| 2001/0039457 A1 | 11/2001 | Boyer et al. | |
| 2001/0041941 A1 | 11/2001 | Boyer et al. | |
| 2001/0051830 A1 | 12/2001 | Tuke et al. | |
| 2002/0007294 A1 | 1/2002 | Bradbury et al. | |
| 2002/0022889 A1 | 2/2002 | Chibrac et al. | |
| 2002/0022890 A1 | 2/2002 | Jacobsson et al. | |
| 2002/0040244 A1 | 4/2002 | Despres et al. | |
| 2002/0040245 A1 | 4/2002 | Lester et al. | |
| 2002/0042656 A1 | 4/2002 | Hunter et al. | |
| 2002/0045949 A1 | 4/2002 | Ling et al. | |
| 2002/0049500 A1 | 4/2002 | Draenert | |
| 2002/0052659 A1 | 5/2002 | Hayes et al. | |
| 2002/0059000 A1 | 5/2002 | Dwyer et al. | |
| 2002/0068980 A1 | 6/2002 | Serbousek et al. | |
| 2002/0072799 A1 | 6/2002 | Despres et al. | |
| 2002/0082706 A1 | 6/2002 | Raugel | |
| 2002/0107577 A1 | 8/2002 | Storer et al. | |
| 2002/0116007 A1 | 8/2002 | Lewis | |
| 2002/0116068 A1 | 8/2002 | McLean | |
| 2002/0120340 A1 | 8/2002 | Metzger et al. | |
| 2002/0120341 A1 | 8/2002 | Stumpo et al. | |
| 2002/0128653 A1 | 9/2002 | Haidukewych | |
| 2002/0138148 A1 | 9/2002 | Hyde | |
| 2002/0138151 A1 | 9/2002 | Hubbard et al. | |
| 2002/0139818 A1 | 10/2002 | McGuffey | |
| 2002/0143402 A1 | 10/2002 | Steinberg | |
| 2002/0143403 A1 | 10/2002 | Vaidyanathan et al. | |
| 2002/0151978 A1 | 10/2002 | Zacouto et al. | |
| 2002/0156536 A1 | 10/2002 | Harris et al. | |
| 2002/0165615 A1 | 11/2002 | Abouaf et al. | |
| 2002/0173853 A1 | 11/2002 | Corl et al. | |
| 2003/0009232 A1 | 1/2003 | Metzger et al. | |
| 2003/0009234 A1 | 1/2003 | Treacy et al. | |
| 2003/0014120 A1 | 1/2003 | Carson et al. | |
| 2003/0022069 A1 | 1/2003 | Karube et al. | |
| 2003/0033018 A1 | 2/2003 | Merchant | |
| 2003/0040805 A1 | 2/2003 | Minamikawa | |
| 2003/0050645 A1 | 3/2003 | Parker et al. | |
| 2003/0050703 A1 | 3/2003 | Harris et al. | |
| 2003/0050705 A1 | 3/2003 | Cueille et al. | |
| 2003/0055508 A1 | 3/2003 | Metzger et al. | |
| 2003/0055509 A1 | 3/2003 | McCue et al. | |
| 2003/0060889 A1 | 3/2003 | Tarabishy | |
| 2003/0060890 A1 | 3/2003 | Tarabishy | |
| 2003/0065397 A1 | 4/2003 | Hanssen et al. | |
| 2003/0074078 A1 | 4/2003 | Doubler et al. |
| 2003/0093156 A1 | 5/2003 | Metzger et al. |
| 2003/0105529 A1 | 6/2003 | Synder et al. |
| 2003/0109933 A1 | 6/2003 | Weissman et al. |
| 2003/0114934 A1 | 6/2003 | Steinberg |
| 2003/0114935 A1 | 6/2003 | Chan et al. |
| 2003/0120346 A1 | 6/2003 | Mercinek et al. |
| 2003/0120347 A1 | 6/2003 | Steinberg |
| 2003/0125810 A1 | 7/2003 | Sullivan et al. |
| 2003/0130740 A1 | 7/2003 | Stocks et al. |
| 2003/0139818 A1 | 7/2003 | Rogers et al. |
| 2003/0149485 A1 | 8/2003 | Tornier |
| 2003/0153981 A1 | 8/2003 | Wang et al. |
| 2003/0153982 A1 | 8/2003 | Pria |
| 2003/0158606 A1 | 8/2003 | Coon et al. |
| 2003/0163202 A1 | 8/2003 | Lakin |
| 2003/0171815 A1 | 9/2003 | Kana et al. |
| 2003/0171817 A1 | 9/2003 | Rambert et al. |
| 2003/0181984 A1 | 9/2003 | Abendschein |
| 2003/0181987 A1 | 9/2003 | Muirhead-Allwood |
| 2003/0204262 A1 | 10/2003 | Ferguson et al. |
| 2003/0204263 A1 | 10/2003 | Justin et al. |
| 2003/0204268 A1 | 10/2003 | Gerbec et al. |
| 2003/0204269 A1 | 10/2003 | Gerbec et al. |
| 2003/0208276 A1 | 11/2003 | Berelsman et al. |
| 2003/0212458 A1 | 11/2003 | Harris et al. |
| 2003/0220697 A1 | 11/2003 | Justin et al. |
| 2003/0220699 A1 | 11/2003 | Hunter et al. |
| 2003/0225457 A1 | 12/2003 | Justin et al. |
| 2003/0225458 A1 | 12/2003 | Donkers et al. |
| 2003/0229356 A1 | 12/2003 | Dye |
| 2003/0229398 A1 | 12/2003 | Iesaka |
| 2004/0002766 A1 | 1/2004 | Hunter et al. |
| 2004/0019380 A1 | 1/2004 | Baege et al. |
| 2004/0019382 A1 | 1/2004 | Amirouche et al. |
| 2004/0019386 A1 | 1/2004 | Ferree |
| 2004/0024460 A1 | 2/2004 | Ferree |
| 2004/0030344 A1 | 2/2004 | Dye et al. |
| 2004/0030394 A1 | 2/2004 | Horber |
| 2004/0030400 A1 | 2/2004 | Horber |
| 2004/0034432 A1 | 2/2004 | Hughes et al. |
| 2004/0039449 A1 | 2/2004 | Tornier |
| 2004/0039451 A1 | 2/2004 | Southworth |
| 2004/0049284 A1 | 3/2004 | German et al. |
| 2004/0049285 A1 | 3/2004 | Haas |
| 2004/0049286 A1 | 3/2004 | German et al. |
| 2004/0054418 A1 | 3/2004 | McLean et al. |
| 2004/0059427 A1 | 3/2004 | Serbousek et al. |
| 2004/0068324 A1 | 4/2004 | Grundei |
| 2004/0073226 A1 | 4/2004 | Cotting et al. |
| 2004/0073315 A1 | 4/2004 | Justin et al. |
| 2004/0078083 A1 | 4/2004 | Gibbs et al. |
| 2004/0083004 A1 | 4/2004 | Wasielewski |
| 2004/0098133 A1 | 5/2004 | Carignan et al. |
| 2004/0098134 A1 | 5/2004 | Meulink |
| 2004/0102851 A1 | 5/2004 | Saladino |
| 2004/0102852 A1 | 5/2004 | Johnson et al. |
| 2004/0107594 A1 | 6/2004 | Afriat |
| 2004/0117023 A1 | 6/2004 | Gerbec et al. |
| 2004/0117024 A1 | 6/2004 | Gerbec et al. |
| 2004/0117029 A1 | 6/2004 | Lewis et al. |
| 2004/0122521 A1 | 6/2004 | Lee et al. |
| 2004/0122524 A1 | 6/2004 | Hunter et al. |
| 2004/0143336 A1 | 7/2004 | Burkinshaw |
| 2004/0143341 A1 | 7/2004 | McLean |
| 2004/0147926 A1 | 7/2004 | Iversen |
| 2004/0153063 A1 | 8/2004 | Harris |
| 2004/0162619 A1 | 8/2004 | Blaylock et al. |
| 2004/0162620 A1 | 8/2004 | Wyss |
| 2004/0162621 A1 | 8/2004 | Crofford |
| 2004/0172137 A1 | 9/2004 | Blaylock et al. |
| 2004/0172139 A1 | 9/2004 | Dwyer et al. |
| 2004/0186580 A1 | 9/2004 | Steinmann |
| 2004/0186586 A1 | 9/2004 | Seyer et al. |
| 2004/0193282 A1 | 9/2004 | Hanes |
| 2004/0199257 A1 | 10/2004 | Dooney |
| 2004/0199259 A1 | 10/2004 | Pichon et al. |
| 2004/0204760 A1 | 10/2004 | Fitz et al. |
| 2004/0204767 A1 | 10/2004 | Park et al. |

| | | | | | | |
|---|---|---|---|---|---|---|
| 2004/0210316 | A1 | 10/2004 | King et al. | 2005/0256584 A1 | 11/2005 | Farrar |
| 2004/0225368 | A1 | 11/2004 | Plumet et al. | 2005/0261776 A1 | 11/2005 | Taylor |
| 2004/0225370 | A1 | 11/2004 | Cruchet et al. | 2005/0267584 A1 | 12/2005 | Burdulis et al. |
| 2004/0225371 | A1 | 11/2004 | Roger | 2005/0267585 A1 | 12/2005 | Sidebotham |
| 2004/0226343 | A1 | 11/2004 | Babler et al. | 2005/0267590 A1 | 12/2005 | Lee |
| 2004/0236428 | A1 | 11/2004 | Burkinshaw et al. | 2005/0278034 A1 | 12/2005 | Johnson et al. |
| 2004/0243249 | A1 | 12/2004 | Ishihara et al. | 2005/0283252 A1 | 12/2005 | Coon et al. |
| 2004/0255749 | A1 | 12/2004 | Hayden | 2005/0283253 A1 | 12/2005 | Coon et al. |
| 2004/0260396 | A1 | 12/2004 | Ferree et al. | 2005/0283254 A1 | 12/2005 | Hayes et al. |
| 2004/0267374 | A1 | 12/2004 | Friedrichs | 2005/0288791 A1 | 12/2005 | Tornier et al. |
| 2004/0267375 | A1 | 12/2004 | Friedrichs | 2005/0288793 A1 | 12/2005 | Dong et al. |
| 2005/0004677 | A1 | 1/2005 | Johnson | 2006/0004463 A1 | 1/2006 | Lewis et al. |
| 2005/0004678 | A1 | 1/2005 | Richards | 2006/0009774 A1 | 1/2006 | Goble et al. |
| 2005/0010288 | A1 | 1/2005 | Merrill et al. | 2006/0009853 A1 | 1/2006 | Justin et al. |
| 2005/0010303 | A1 | 1/2005 | Nogier | 2006/0009854 A1 | 1/2006 | Justin et al. |
| 2005/0010304 | A1 | 1/2005 | Jamali | 2006/0009855 A1 | 1/2006 | Goble et al. |
| 2005/0021149 | A1 | 1/2005 | Borruto et al. | 2006/0009857 A1 | 1/2006 | Gibbs et al. |
| 2005/0027302 | A1 | 2/2005 | Cueille et al. | 2006/0015188 A1 | 1/2006 | Grimes |
| 2005/0033442 | A1 | 2/2005 | Fisher et al. | 2006/0030945 A1 | 2/2006 | Wright |
| 2005/0033445 | A1 | 2/2005 | Siebel | 2006/0052876 A1 | 3/2006 | Wozencroft et al. |
| 2005/0038443 | A1 | 2/2005 | Hedley et al. | 2006/0058883 A1 | 3/2006 | Aram et al. |
| 2005/0043807 | A1 | 2/2005 | Wood | 2006/0058884 A1 | 3/2006 | Aram et al. |
| 2005/0043812 | A1 | 2/2005 | Corl et al. | 2006/0058886 A1 | 3/2006 | Wozencroft |
| 2005/0049524 | A1 | 3/2005 | Lefevre et al. | 2006/0064169 A1 | 3/2006 | Ferree |
| 2005/0049713 | A1 | 3/2005 | Garber et al. | 2006/0074491 A1 | 4/2006 | Smith et al. |
| 2005/0055102 | A1 | 3/2005 | Tornier et al. | 2006/0085079 A1 | 4/2006 | Carroll |
| 2005/0059972 | A1 | 3/2005 | Biscup | 2006/0100714 A1 | 5/2006 | Ensign |
| 2005/0060040 | A1 | 3/2005 | Auxepaules et al. | 2006/0129247 A1 | 6/2006 | Brown et al. |
| 2005/0071014 | A1 | 3/2005 | Barnett et al. | 2006/0142865 A1 | 6/2006 | Hyde |
| 2005/0071015 | A1 | 3/2005 | Sekel | 2006/0142867 A1 | 6/2006 | Metzger et al. |
| 2005/0075641 | A1 | 4/2005 | Singhatat et al. | 2006/0149285 A1 | 7/2006 | Burgi et al. |
| 2005/0080490 | A1 | 4/2005 | Bertram | 2006/0167462 A1 | 7/2006 | Raugel et al. |
| 2005/0085823 | A1 | 4/2005 | Murphy | 2006/0167554 A1 | 7/2006 | Heck et al. |
| 2005/0090903 | A1 | 4/2005 | Khandkar et al. | 2006/0167556 A1 | 7/2006 | Lazennec et al. |
| 2005/0102032 | A1 | 5/2005 | Beynnon et al. | 2006/0167557 A1 | 7/2006 | Terrill |
| 2005/0102033 | A1 | 5/2005 | Lambert et al. | 2006/0167559 A1 | 7/2006 | Johnstone et al. |
| 2005/0102034 | A1 | 5/2005 | E. Hayes et al. | 2006/0167560 A1 | 7/2006 | Heck et al. |
| 2005/0102038 | A1 | 5/2005 | Grundei | 2006/0173547 A1 | 8/2006 | Ensign |
| 2005/0107884 | A1 | 5/2005 | Johnson et al. | 2006/0173548 A1 | 8/2006 | Auxepaules et al. |
| 2005/0119755 | A1 | 6/2005 | Kristensen | 2006/0178749 A1 | 8/2006 | Pendleton et al. |
| 2005/0125067 | A1 | 6/2005 | Sweeney | 2006/0178750 A1 | 8/2006 | Chieng |
| 2005/0131540 | A1 | 6/2005 | Trieu | 2006/0184249 A1 | 8/2006 | Tarabishy |
| 2005/0137603 | A1 | 6/2005 | Belew et al. | 2006/0190086 A1 | 8/2006 | Clemow et al. |
| 2005/0137708 | A1 | 6/2005 | Clark | 2006/0195196 A1 | 8/2006 | Pendleton et al. |
| 2005/0137711 | A1 | 6/2005 | Southworth et al. | 2006/0206210 A1 | 9/2006 | Abicht et al. |
| 2005/0143828 | A1 | 6/2005 | Collins et al. | 2006/0229734 A1 | 10/2006 | Yoon |
| 2005/0143835 | A1 | 6/2005 | Gilbertson | 2006/0235538 A1 | 10/2006 | Rochetin et al. |
| 2005/0143836 | A1 | 6/2005 | Steinberg | 2006/0241776 A1 | 10/2006 | Brown et al. |
| 2005/0149043 | A1 | 7/2005 | Parry et al. | 2006/0241781 A1 | 10/2006 | Brown et al. |
| 2005/0149047 | A1 | 7/2005 | Parry et al. | 2006/0265079 A1 | 11/2006 | D'Alessio |
| 2005/0154470 | A1 | 7/2005 | Sekel | 2007/0010890 A1 | 1/2007 | Collazo |
| 2005/0154471 | A1 | 7/2005 | Aram et al. | 2007/0021838 A1 | 1/2007 | Dugas et al. |
| 2005/0165490 | A1 | 7/2005 | Tornier | 2007/0088443 A1 | 4/2007 | Hanssen et al. |
| 2005/0165491 | A1 | 7/2005 | Diaz | 2007/0129809 A1 | 6/2007 | Meridew et al. |
| 2005/0165492 | A1 | 7/2005 | Fitz | 2007/0173948 A1 | 7/2007 | Meridew et al. |
| 2005/0171612 | A1 | 8/2005 | Rolston | 2007/0196230 A1 | 8/2007 | Hamman et al. |
| 2005/0177172 | A1 | 8/2005 | Acker et al. | 2008/0167722 A1 | 7/2008 | Metzger et al. |
| 2005/0177242 | A1 | 8/2005 | Lotke | 2009/0062806 A1 | 3/2009 | Scott et al. |
| 2005/0177244 | A1 | 8/2005 | Steinberg | 2009/0125114 A1 | 5/2009 | May et al. |
| 2005/0187635 | A1 | 8/2005 | Metzger | 2009/0149964 A1 | 6/2009 | May et al. |
| 2005/0187637 | A1 | 8/2005 | Karrer et al. | 2009/0299482 A1 | 12/2009 | Metzger et al. |
| 2005/0192675 | A1 | 9/2005 | Robinson | | | |
| 2005/0202371 | A1 | 9/2005 | McGuire | FOREIGN PATENT DOCUMENTS | | |
| 2005/0203535 | A1 | 9/2005 | Parry et al. | EP 0000549 A1 | | 2/1979 |
| 2005/0203629 | A1 | 9/2005 | Cipolletti et al. | EP 0378928 A1 | | 7/1990 |
| 2005/0209604 | A1 | 9/2005 | Penenberg et al. | EP 0538987 A1 | | 4/1993 |
| 2005/0211562 | A1 | 9/2005 | Rowe et al. | EP 0555003 A1 | | 8/1993 |
| 2005/0216091 | A1 | 9/2005 | Wasielewski | EP 0689796 A1 | | 1/1996 |
| 2005/0228394 | A1 | 10/2005 | Bihary et al. | EP 0797417 A1 | | 10/1997 |
| 2005/0228395 | A1 | 10/2005 | Auxepaules et al. | EP 853930 A2 | | 7/1998 |
| 2005/0228502 | A1 | 10/2005 | Deloge et al. | EP 0947181 A2 | | 10/1999 |
| 2005/0228503 | A1 | 10/2005 | Gundolf | EP 0985386 A2 | | 3/2000 |
| 2005/0240275 | A1 | 10/2005 | Chappuis | EP 993813 A2 | | 4/2000 |
| 2005/0240276 | A1 | 10/2005 | Shea et al. | EP 01004283 A2 | | 5/2000 |
| 2005/0246026 | A1 | 11/2005 | Lewis et al. | EP 1398007 A2 | | 3/2004 |
| 2005/0246027 | A1 | 11/2005 | Metzger et al. | EP 1430856 A1 | | 6/2004 |
| 2005/0246028 | A1 | 11/2005 | Pappas et al. | FR 2718953 A1 | | 10/1995 |
| 2005/0246030 | A1 | 11/2005 | Yao | FR 2793677 A1 | | 11/2000 |
| 2005/0256576 | A1 | 11/2005 | Moskowitz et al. | GB 1553836 A | | 10/1979 |

| | | | |
|---|---|---|---|
| GB | 2223172 A | 4/1990 | |
| JP | 58141847 A | 8/1983 | |
| WO | WO-9613233 A1 | 5/1996 | |
| WO | WO-0038598 A1 | 7/2000 | |
| WO | WO-0205732 A1 | 1/2002 | |
| WO | WO-03065939 A1 | 8/2003 | |
| WO | WO-2004078069 A2 | 9/2004 | |
| WO | WO-2004080340 A2 | 9/2004 | |

OTHER PUBLICATIONS

"AGC Total Knee System, Tradition Series," brochure, (11 pages) 1995. Biomet Orthopedics, Inc.

"Ascent™ Total Knee System, Revision Surgical Technique," (pp. 1-24) 2001. Biomet Orthopedics, Inc.

"FINN® Knee System Modularity and Surgical Latitude, Product Ordering Information," catalog, (4 pages) 1994. Biomet, Inc.

"FINN® Knee System Modularity and Surgical Latitude," brochure (pp. 1-20) 1995 Biomet, Inc.

"FINN® Knee System Modularity and Surgical Latitude," brochure, (11 pages) 1990. Biomet, Inc.

"Kinemax® Plus Total Stabiliser (TS) Revision Surgical technique, Xcelerate Instrumentation," brochure/catalog. Stryker Howmedica Osteonics (Dated at least as early as Apr. 4, 2005.).

"OSS™ Orthopaedic Salvage System, Femoral/Tibial Augmentation," brochure, pp. 1-9. 2003, 2004 Biomet Orthopedics, Inc.

"Passport™ Revision Instrumentation, Howmedica Osteonics Total Knee Revision System Surgical Protocol," brochure, Jun. 2000 (pp. 1-27) Stryer® Howmedica Osteonics.

"S-Rom Total Hip System Surgical Technique," (19 pages) located at http://www.rpa.spot.pt/Main-Sections/Informacao-ao-Profissional-de-Saude.aspx?lang=en-GB, web site copyrighted 2008; accessed Oct. 13, 2010. DePuy.

"S-Rom Total Hip System Surgical Technique," brochure (17 pages) 2000. DePuy Orthopaedics, Inc. Depuy Orthapaedics, Inc.

"The RHK™ System, RHK™ controlled rotation," brochure (2 sheets) 2004. ArCom™. Biomet Europe.

"Vanguard Complete Knee System, Cruciate Retaining," brochure (6 pages) 2007. Biomet Orthopedics, Inc.

"Vanguard Complete Knee System, System Summary," brochure, (4 sheets) 2007. Biomet Orthopedics, Inc.

European Search Report for EP 02 25 1274 completed on Sep. 12, 2003 (mailed on Sep. 22, 2003).

International Preliminary Report on Patentability and Written Opinion issued Jul. 14, 2009 for PCT/US2008/000374 claiming benefit of U.S. Appl. No. 60/879,733, filed Jan. 10, 2007; and U.S. Appl. No. 60/978,949, filed Oct. 10, 2007.

International Preliminary Report on Patentability for PCT/US2008/079545 issued Apr. 13, 2010, claiming priority to U.S. Appl. No. 60/978,949, filed Oct. 10, 2007.

International Search Report and Written Opinion for PCT/US2008/000374 mailed Jun. 6, 2008.

International Search Report and Written Opinion for PCT/US2008/079545 mailed Jan. 14, 2009 claiming priority to U.S. Appl. No. 60/978,949, filed Oct. 10, 2007.

International Search Report and Written Opinion mailed Jan. 25, 2011 for PCT/US2010/044395 Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.

Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of 12/248,509, filed Oct. 9, 2008.

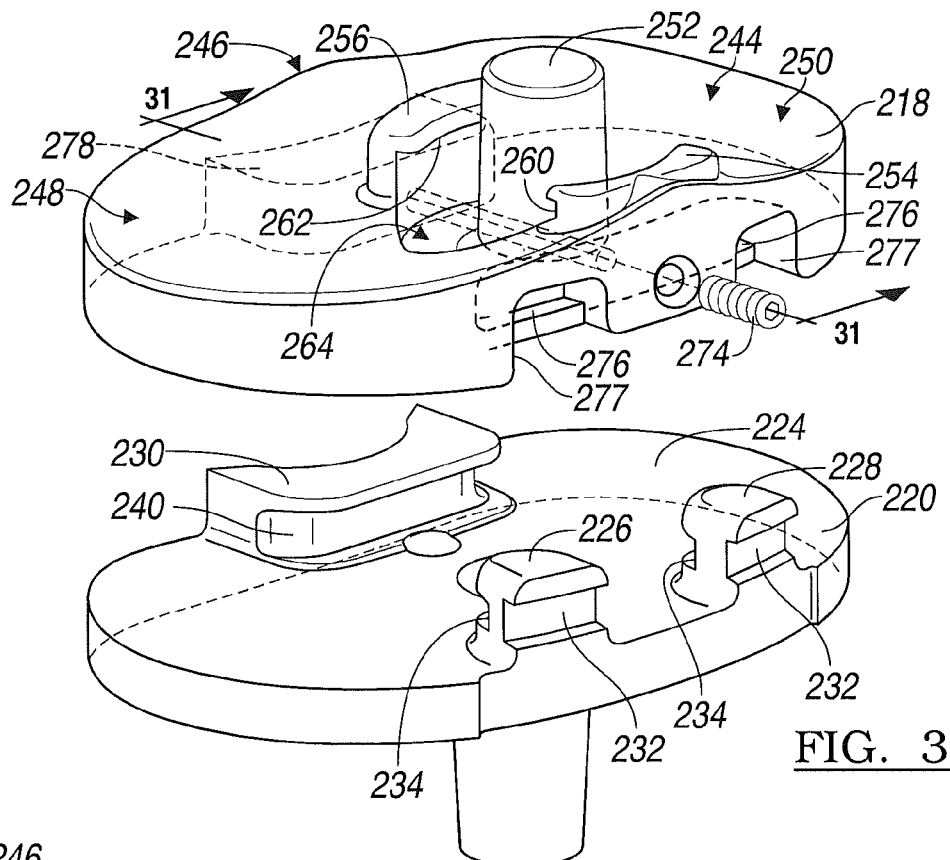
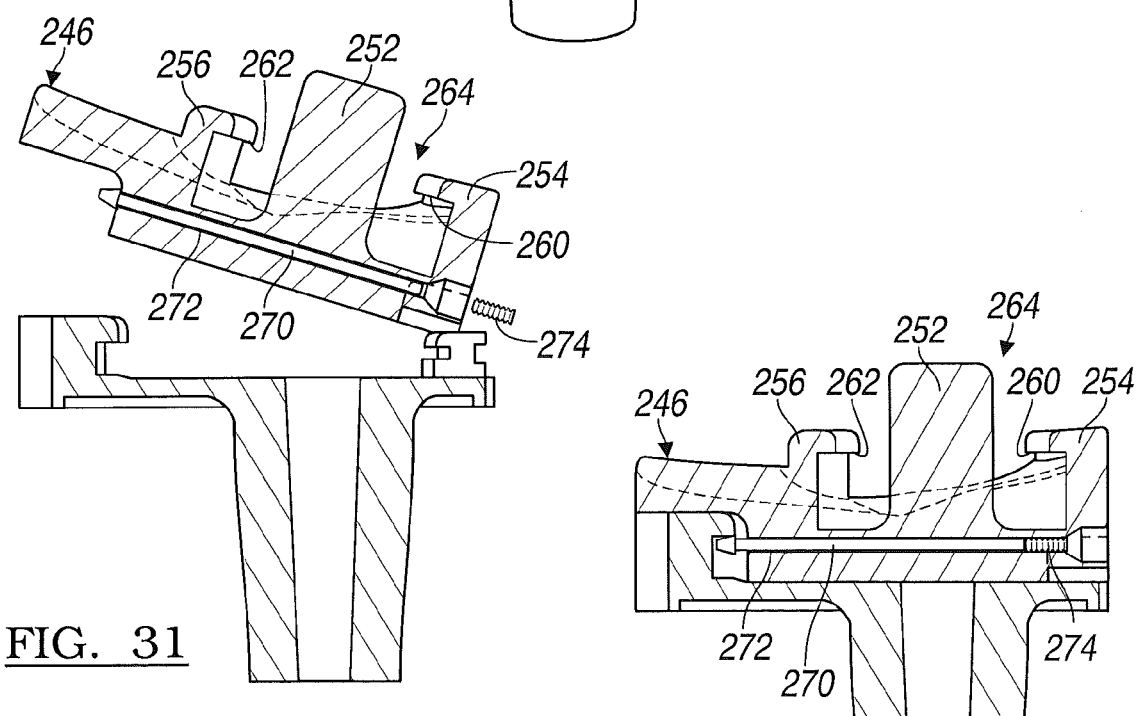
FIG. 30
FIG. 31
FIG. 32

KNEE JOINT PROSTHESIS SYSTEM AND METHOD FOR IMPLANTATION

CROSS-REFERENCE TO RELATED APPLICATIONS

This application is a continuation-in-part of U.S. patent application Ser. No. 12/536,056, filed Aug. 5, 2009, which is a continuation-in-part of U.S. patent application Ser. No. 11/972,359, filed Jan. 10, 2008, which claims priority to U.S. Provisional Application No. 60/978,949, filed Oct. 10, 2007 and U.S. Provisional Application No. 60/879,733 filed Jan. 10, 2007. This application is also a continuation-in-part of U.S. patent application Ser. No. 12/248,517, filed Oct. 9, 2008, which is a continuation-in-part of U.S. patent application Ser. No. 11/972,359, filed Jan. 10, 2008, which claims priority to U.S. Provisional Application No. 60/978,949, filed Oct. 10, 2007 and U.S. Provisional Application No. 60/879, 733 filed Jan. 10, 2007. This application is also a continuation-in-part of U.S. patent application Ser. No. 12/248,509, filed Oct. 9, 2008, which is a continuation-in-part of U.S. patent application Ser. No. 11/972,359, filed Jan. 10, 2008, which claims priority to U.S. Provisional Application No. 60/978,949, filed Oct. 10, 2007. The entire disclosures of each of the above applications are incorporated herein by reference.

FIELD

The present disclosure relates to knee joint prosthesis and more particularly to a hinged knee joint prosthesis and a method of assembling and implanting the same.

BACKGROUND

This section provides background information related to the present disclosure which is not necessarily prior art.

A knee joint prosthesis typically comprises a femoral component and a tibial component. The femoral component and tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. In some instances, the primary knee prosthesis, knee tendons and ligaments may become damaged or deteriorated. In this regard, it may be necessary for a revision knee joint prosthesis to eliminate one or more of these motions in order to provide adequate stability. In this way, it may be desirable to provide a cruciate retaining (CR) revision knee, a fully constrained revision knee, a posterior stabilized (PS) revision knee or a hinged revision knee for example. Furthermore, in some instances it may be necessary to account for bone loss in areas adjacent to such knee joint prostheses.

SUMMARY

This section provides a general summary of the disclosure, and is not a comprehensive disclosure of its full scope or all of its features.

A prosthesis system for replacing a knee joint between a femur and a tibia can include a femoral component, a tibial component, a bearing, a first yoke, and a first key. The femoral component can include a first condylar portion, a second condylar portion, a first sidewall extending superiorly from the first condylar portion, a second sidewall extending superiorly from the second condylar portion where the first and second sidewalls collectively comprise a first hinge portion. The tibial component can have a bone engaging inferior surface and a bearing engaging superior surface. The bearing can have an inferior surface that engages the bearing engaging surface and a superior femoral engaging surface. The bearing can define an opening. The first yoke can have an inferior portion, a superior portion and a yoke keyway extending through the therethrough. The superior portion can have an axle assembly that comprises a second hinge portion that hingedly couples to the first hinge portion. The axle assembly can include at least one axle post having a first engaging portion thereon. The first key can be removably inserted into the yoke keyway. The first key can have a second engaging portion thereon that interacts with a first engaging portion causing the at least one axle post to advance outwardly into locking engagement with the first hinged portion in an assembled position.

According to additional features, the axle assembly can further comprise a first and a second axle post that both meshingly interact with the second engaging portion of the key and advance respectively outwardly into locking engagement with the first hinge portion upon advancement of the first key into the yoke keyway. The first engaging portion can include first threads formed on both of the first and second axle posts. The axle assembly can further comprise an axle shaft that is threadably connected to both of the first threads of the first and second axle posts. Rotation of the axle shaft causes the first and second axle post to threadably interface with the axle shaft and collectively advance inwardly or outwardly based on the direction of rotation.

According to other features, the prosthesis system can further comprise a first gear on the axle shaft that meshingly engages a second gear provided on the second engaging portion of the first key. The first gear rotates upon linear advancement of the first key into the yoke keyway. In the assembled position, the axle assembly extends a distance that is greater than a distance between the first and second sidewalls of the femoral component.

In other features, a hyper-extension stop is selectively coupled to one of the femoral component or the first yoke. The hyper-extension stop abuts the other of the femoral component or the first yoke during rotation of the femoral component about an axis defined by the first hinge portion and controls degrees of hyper-extension of the femoral component relative to the tibial component. The tibial component can have a superiorly extending post that passes through the opening in the bearing in the assembled position. The post can define an annular groove. The bearing can include a first finger that selectively locates into the annular groove in the assembled position. The first yoke can include a second finger that selectively and concurrently locates into the annular groove with the first finger in the assembled position. The first finger can protrude in an anterior direction and the second finger can protrude in a posterior direction. The bearing can define a bearing keyway. When the first key is advanced into the bearing keyway subsequent to being inserted into the yoke keyway, the first key inhibits anterior motion of the first yoke and posterior motion of the bearing while maintaining location of the first and second fingers in the groove of the post.

According to additional features, the prosthesis system can further comprise a second yoke that is selectively and alternatively coupled to the first hinge portion. The second yoke can have a solid axle that extends through the second yoke and at least partially through the first hinge portion. A second key can be selectively and alternatively inserted through a passage in the second yoke and a bearing passage defined through the bearing.

A method of implanting a prosthesis for replacing a knee joint between a femur and a tibia can include, implanting a tibial component having a bone engaging inferior surface, a bearing engaging superior surface and a superiorly extending post that defines a groove thereon. The bearing can be positioned onto the bearing engaging superior surface. The bearing can have a first finger. The bearing can be advanced until the first finger locates into the groove. An amount of constraint that is desired for the prosthesis based on a condition of the femur can be determined. A kit of yokes can be provided that comprise at least a first yoke and a second yoke. Each yoke from the kit of yokes can have at least one axle post that locates into locking engagement with a femoral component in an assembled position. A desired yoke can be selected from the kit of yokes based on the determined amount of constraint. A second finger provided on the selected yoke can be advanced into the groove. A key can be advanced into cooperative engagement with the selected yoke and bearing. The key can inhibit anterior motion of the selected yoke and posterior motion of the bearing while maintaining location of the first and second fingers in the groove of the post.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 30 is an exploded anterior perspective view of a hinged bearing adapter constructed in accordance to one example of the present teachings and shown cooperating with a modular tibial tray;

FIG. 31 is a cross-sectional view of the hinged bearing adapter and tibial tray taken along lines 31-31 of FIG. 30;

FIG. 32 is a cross-sectional view of the hinged bearing adapter and tibial tray of FIG. 31 and shown in an assembled position;

Corresponding reference numerals indicate corresponding parts throughout the several views of the drawings.

DETAILED DESCRIPTION

Example embodiments will now be described more fully with reference to the accompanying drawings.

The following description of the embodiments concerning a hinged knee joint prosthesis are merely exemplary in nature and are not intended to limit the disclosure or its application or uses. Moreover, while the present disclosure is described in detail below generally with respect to a hinged knee joint prosthesis, it will be appreciated by those skilled in the art that the present disclosure is clearly not limited to only a hinged knee joint prosthesis and may be applied to various other types of knee joint prostheses. Furthermore, it will be appreciated that the hinged knee joint prosthesis may be used as part of a revision or primary knee joint procedure.

Figure 1:
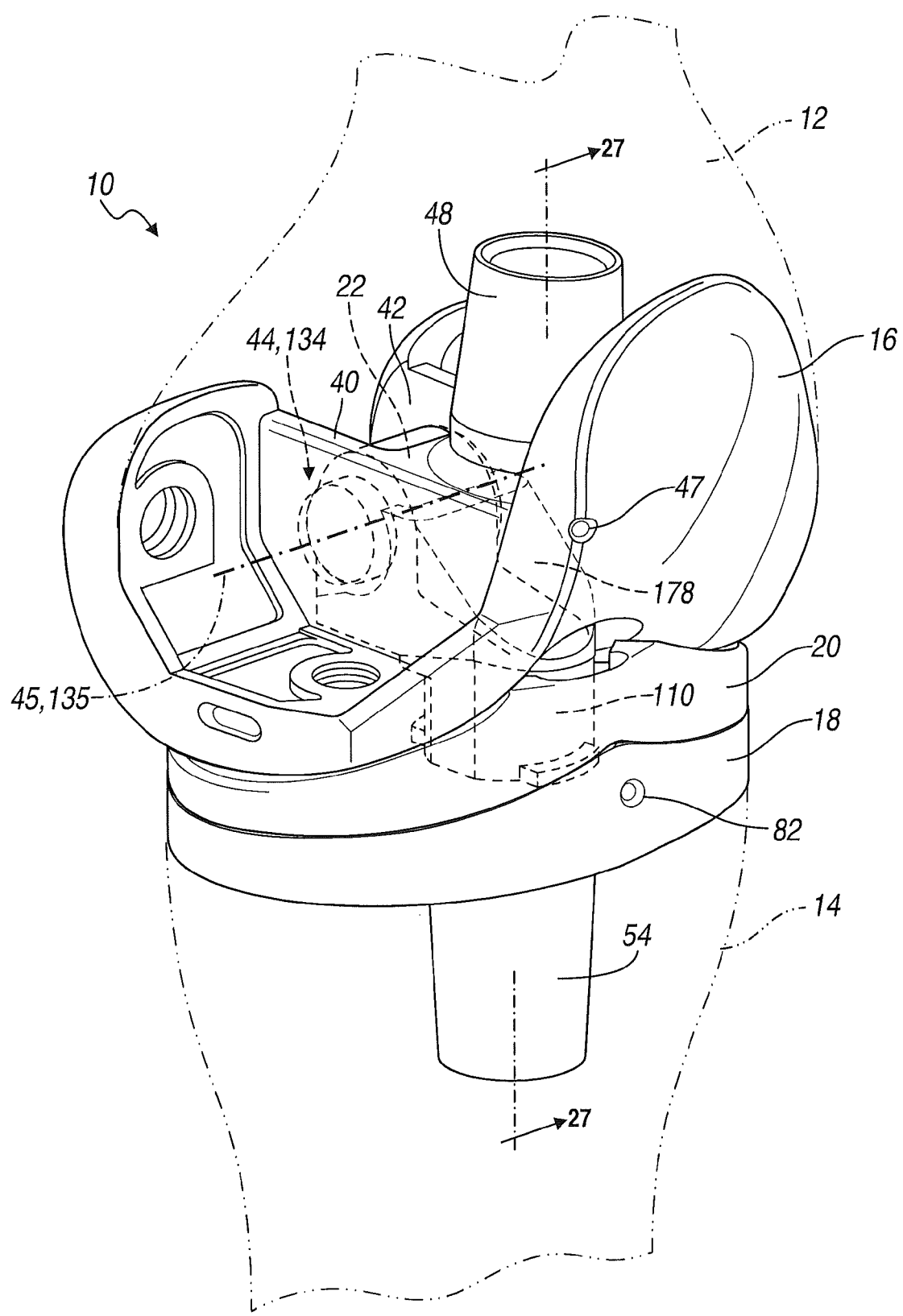
FIG. 1 is an anterior perspective view of a hinged knee joint prosthesis constructed in accordance with one example of the present teachings and shown in an implanted position with a tibia and femur illustrated in phantom.
Figure 2:
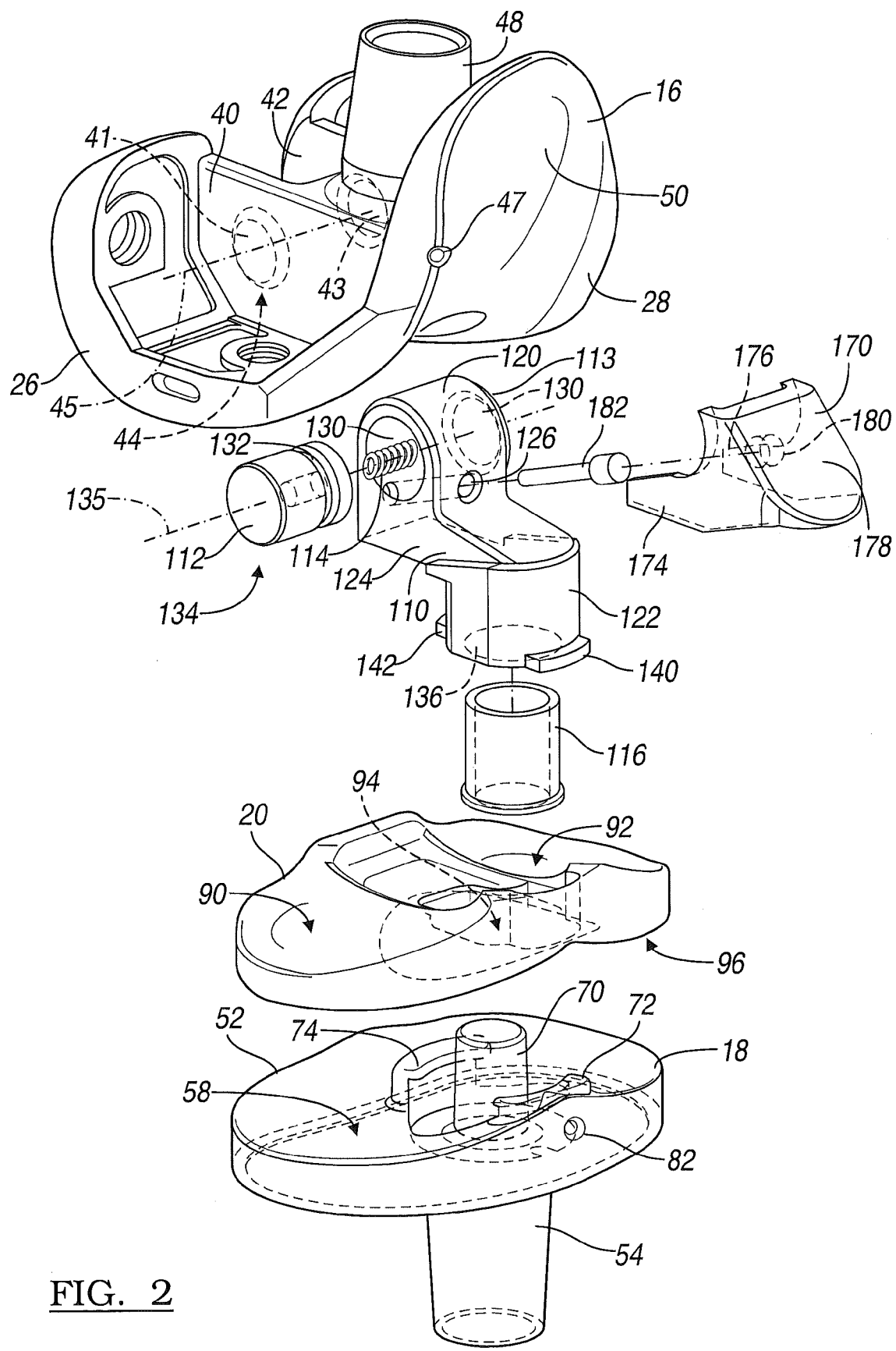
FIG. 2 is an exploded anterior perspective view of the knee joint prosthesis illustrated in FIG. 1.

With initial reference to FIGS. 1 and 2, a knee joint prosthesis constructed in accordance to one example of the present teachings is shown and generally identified at reference numeral 10. The knee joint prosthesis 10 is generally shown as a hinged knee joint prosthesis 10, which is designed to provide adequate stability in case of moderate deterioration or instability of the human knee. This most typically occurs when the anterior and posterior cruciate ligaments are sacrificed or dysfunctional. In some examples, the medial and/or lateral collateral ligaments can be functionally in tact or can also be dysfunctional. The knee joint prosthesis 10 illustrated in FIG. 1 is shown secured to a tibia 12 and a femur 14 of a surgically resected left knee joint, with the tibia 12 and the femur 14 shown in phantom, and with the understanding that a suitable right knee joint prosthesis can be similarly constructed. The knee joint prosthesis 10 can generally include a femoral component 16, a tibial component 18, a rotating tibial bearing 20 and a yoke assembly 22.

Figure 3:
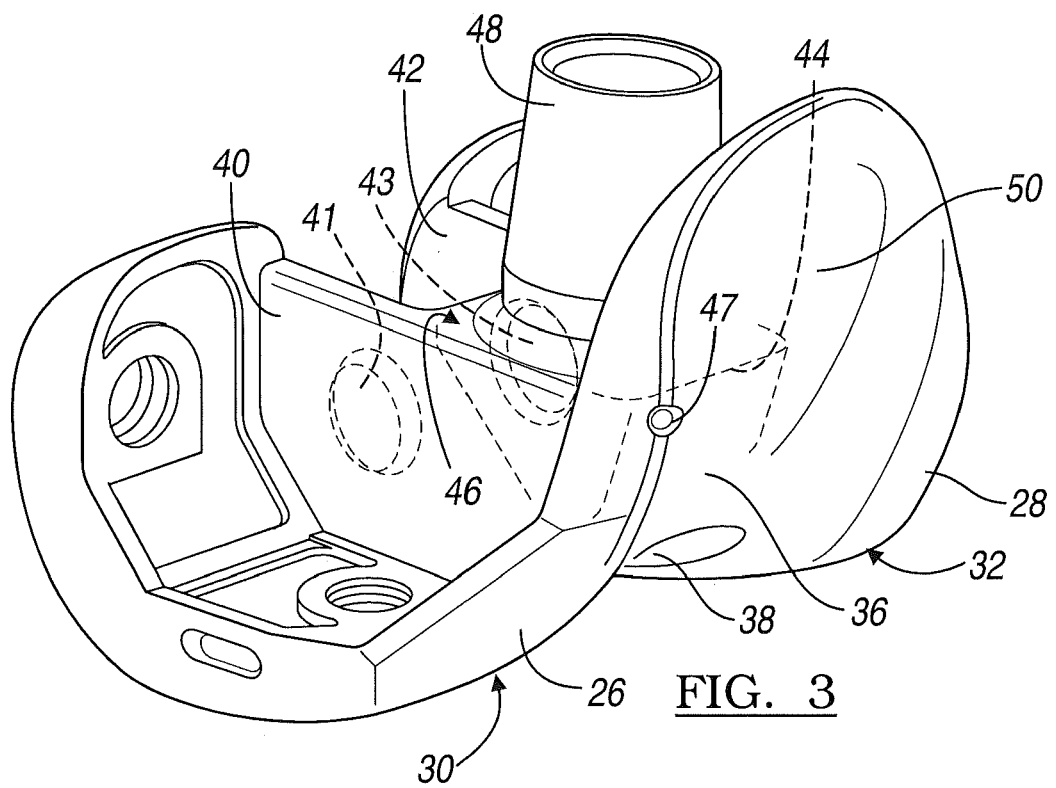
FIG. 3 is a medial perspective view of a right femoral component of the hinged knee joint prosthesis of FIG. 1.
Figure 4:
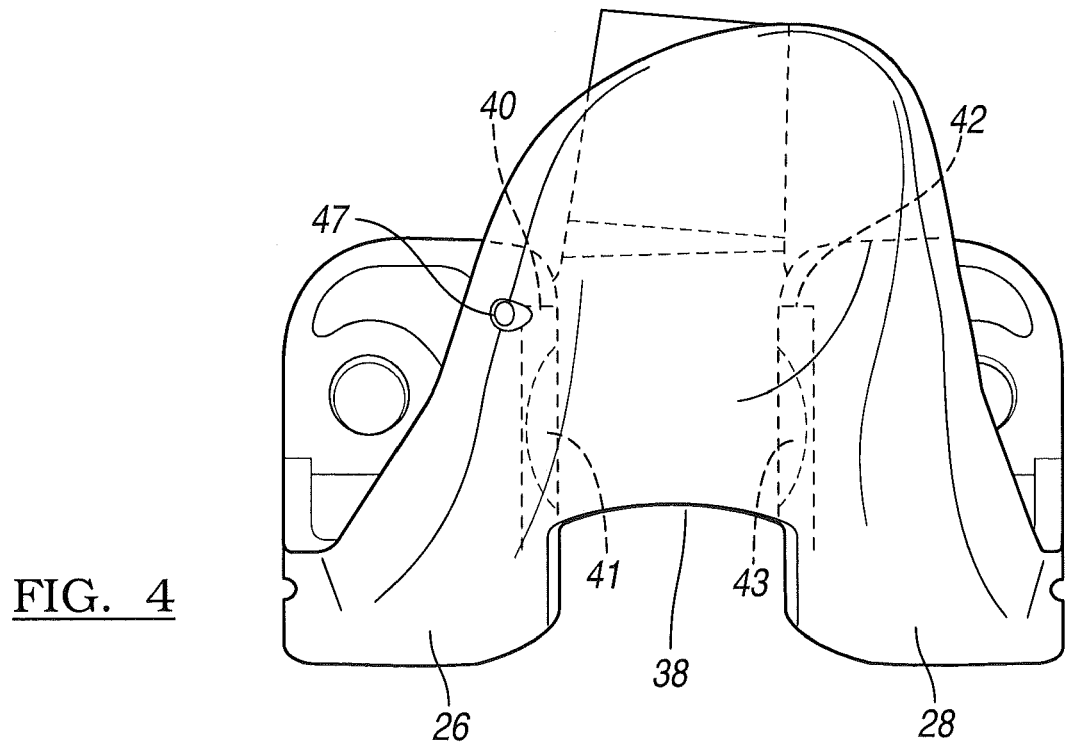
FIG. 4 is an anterior view of the femoral component of FIG. 3.

With continued reference to FIGS. 1 and 2 and additional reference now to FIG. 3, the femoral component 16 will be further described. The femoral component 16 can be adapted to be secured to a distal end of the femur 14 and includes a first condylar portion 26 and a second condylar portion 28 that provide a first femoral bearing surface 30 and a second femoral bearing surface 32, respectively. The first and second condylar portions 26 and 28 of the femoral component 16 can be interconnected by an intercondylar portion 36 that has an intercondylar recess 38. The intercondylar portion 36 can include a first lateral sidewall 40 and a second lateral sidewall 42 that are substantially planar and parallel to one another. Bushings 41 and 43 can be provided on the first and second lateral sidewalls 40 and 42, respectively. The bushings 41 and 43 can be coupled to the first and second lateral sidewalls 40 and 42 or can alternatively be integrally formed with the first and second lateral sidewalls 40 and 42. As will be described herein, the bushings 41 and 43 of the first and second lateral sidewalls 40 and 42 can provide a first hinge portion 44 having a first hinge axis 45. The anterior portions of the first and second lateral sidewalls 40 and 42 can be connected by a superior wall 46. A passage 47 can be formed in the femoral component 16. A superiorly extending portion 48 can be formed on the superior wall 46. The superiorly extending portion 48 can be configured to selectively couple with various adapters and/or stems, such as provided in the Vanguard Complete Knee System (VCKS) manufactured by Biomet Manufacturing Corp. of Warsaw, Ind. A fastener or set screw (not specifically shown) can be advanced through the passage 47 to selectively engage and retain a desired adapter and/or stem. Further description of such components and their assembly to the femoral component may be found in commonly owned and currently pending U.S. patent application Ser. No. 12/248,517, filed on Oct. 9, 2008, which is hereby incorporated by reference.

The femoral component 16 can further include an arcuate patellar portion 50, which is disposed on the anterior surface of the femoral component 16. The patellar portion 50 can be shaped to allow anatomical tracking of a natural or prosthetic patella. The patella prosthesis, which are compatible with the present disclosure may be of varying shape, such as round or dome-shaped and may be constructed from polyethylene, polyethylene with metal backing or other suitable materials. The femoral component 16 can be formed from biocompatible material, such as high strength alloys, including, but not limited to, cobalt-chromium molybdenum alloy or other suitable material. All of the surfaces, which do not contact the femur 14, can be highly polished to provide smooth articulating bearing surfaces.

Figure 5:
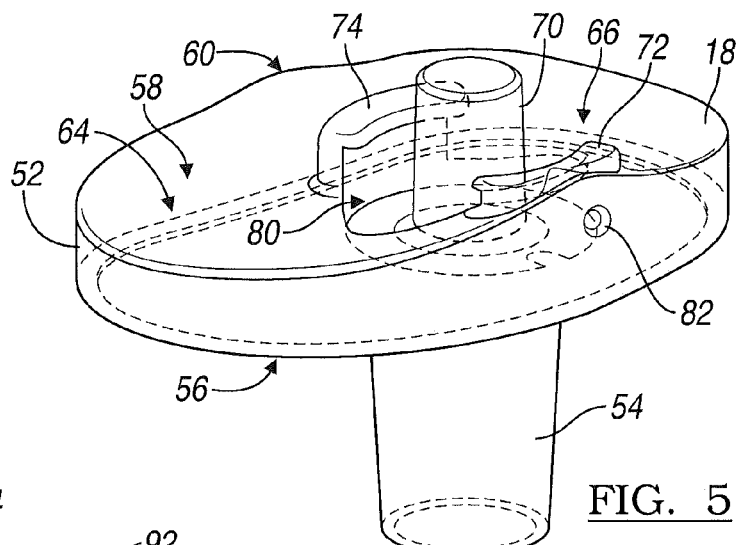
FIG. 5 is an anterior perspective view of a tibial component of the hinged knee joint prosthesis of FIG. 1.
Figure 6:
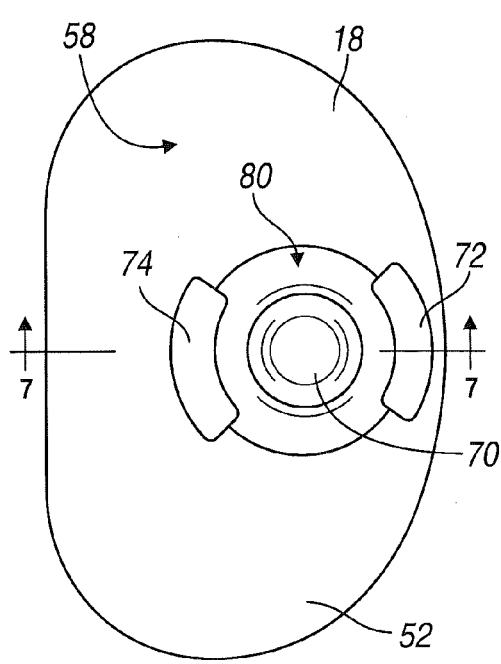
FIG. 6 is a superior view of the tibial component of FIG. 5.
Figure 7:
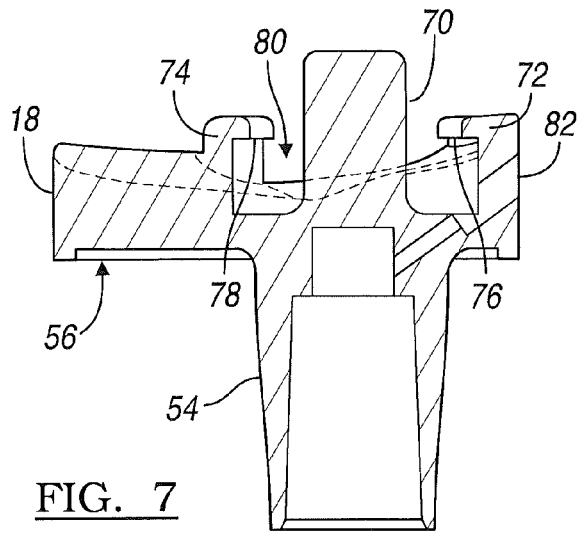
FIG. 7 is a cross-sectional view of the tibial component of FIG. 6 taken along line 7-7.

Turning now to FIGS. 5-7, the tibial component 18 will be further described. The tibial component 18 can be adapted to be secured to the proximal end of the tibia 12 after the tibia 12 has been resected in a manner known in the art. The tibial component 18 can include a platform-like tibial tray 52 having an inferiorly extending tibial stem 54. The tibial stem 54 can be adapted to be received in a corresponding opening made by the surgeon in the longitudinal center of the tibia 12. The tibial tray 52 can have a generally planar inferior bone engaging surface 56 and a bi-helical superior surface 58. The bi-helical superior surface 58 can include a raised middle portion 60, a first depression 64, and a second depression 66, wherein the respective first and second depressions 64 and 66 are formed on either side of the raised middle portion 60.

A superiorly extending post 70 can be centrally formed on the tibial tray 52. An anterior finger 72 and a posterior finger 74 can extend generally superiorly from the raised middle portion 60 of the tibial tray 52. The anterior finger 72 can have a first catch surface 76. The posterior finger 74 can have a second catch surface 78. A channel 80 can be arranged at an annular recess provided between the post 70 and the respective anterior and posterior fingers 72 and 74.

A passage 82 can be formed in the tibial tray 52 that generally extends to the tibial stem 54. The passage 82 can be arranged for accepting a fastener or set screw (not specifically shown) for cooperating with various components (such as stems and/or adapters) that can be coupled to the tibial stem 54. Examples of such stems and adapters may be provided by the Vanguard Complete Knee System (VCKS) manufactured by Biomet Manufacturing Corp. of Warsaw, Ind. Further description of assembly of the tibial component 18 with such components may be found in commonly owned and currently pending U.S. patent application Ser. No. 12/248,517, filed on Oct. 9, 2008, which is hereby incorporated by reference.

The bi-helical superior surface 58 can be substantially polished, such that the rotating tibial bearing 20 may articulate smoothly thereon. The bi-helical superior surface 58 can generally be formed by a first helical portion at the first depression 64 and a second helical portion at the second depression 66. The tibial component 18 can be formed from cobalt-chromium molybdenum or any other suitable biocompatible material. While the anterior finger 72 and the posterior finger 74 are shown and described as being located in an anterior and posterior position on the tibial tray 52, the fingers 72 and 74 can be located at other orientations around the tibial tray 52, such as outboard of the channel 80. In this way, the fingers 72 and 74 can be located at medial and lateral positions or at any angular position relative to the post 70 that can still satisfy the interlocking and functional interconnection with the rotating tibial bearing 20 as will be described.

Figure 8:
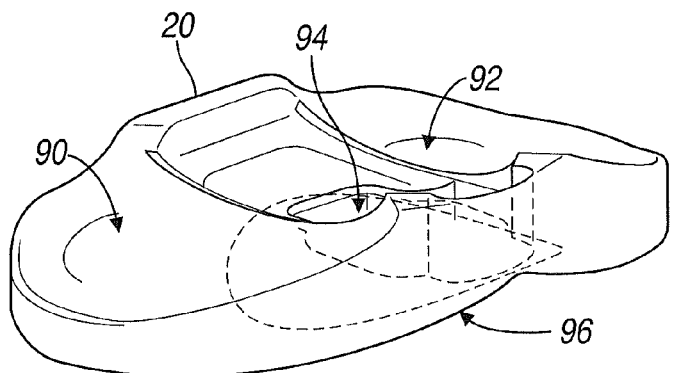
FIG. 8 is an anterior perspective view of a rotating tibial bearing of the hinged knee joint prosthesis of FIG. 1.
Figure 9:
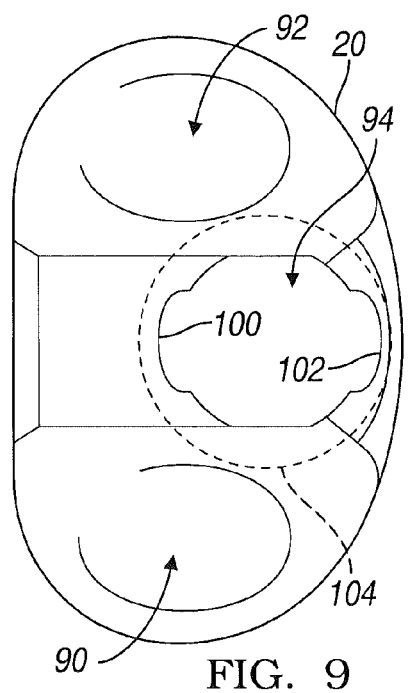
FIG. 9 is a superior view of the rotating tibial bearing of FIG. 8.

With reference now to FIGS. 8 and 9, the rotating tibial bearing 20 will be described in greater detail. The rotating tibial bearing 20 can generally include a first bearing portion 90 and a second bearing portion 92. The first and second bearing portions 90 and 92 are configured to substantially mate with and provide an articulating surface to the first and second femoral bearing surfaces 30 and 32 (FIG. 3) of the femoral component 16. Formed between the first and second bearing portions 90 and 92 is an opening 94. The rotating tibial bearing 20 can have a bi-helical inferior surface 96. A first and a second keyway 100 and 102, respectively can be formed on the rotating tibial bearing 20 at the opening 94. In one example, the first and second keyways 100 and 102 can be arranged in a generally opposing manner in an anterior/posterior orientation. An annular relief 104 can be formed on an inferior side of the rotating tibial bearing 20. The annular relief 104 can be formed a distance radially outward relative to the opening 94. As will become appreciated from the following discussion, the annular relief 104 can accommodate the anterior and posterior fingers 72 and 74 of the tibial component 18. The rotating tibial bearing 20 can be formed from a surgical grade, low friction, low wearing plastic, such as ultra high molecular weight polyethylene (UHMWPE) or other suitable material.

Figure 10:
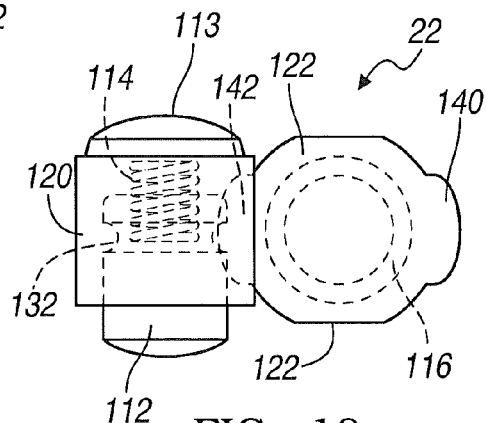
FIG. 10 is a superior view of a yoke assembly of the hinged knee joint prosthesis of FIG. 1.
Figure 11:
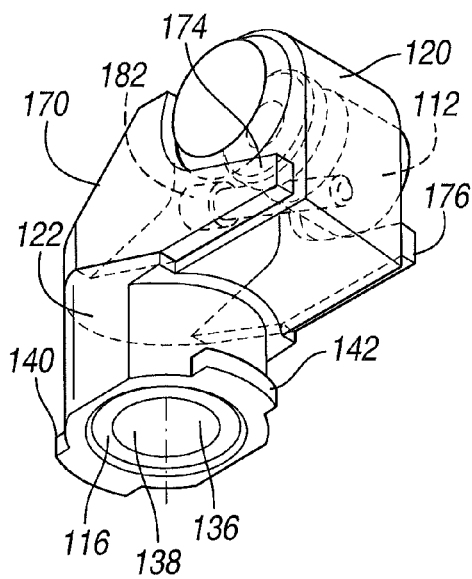
FIG. 11 is a perspective inferior view of the yoke assembly of FIG. 10.

With reference now to FIGS. 2, 10 and 11, the yoke assembly 22 will be described in greater detail. The yoke assembly 22 can generally comprise a yoke 110, an axle post 112, a static axle 113, a biasing member 114 and a bushing 116. The yoke 110 can generally comprise a superior portion 120, an inferior portion 122 and an intermediate connecting portion 124. A passage 126 can be formed generally at an intersection of the superior portion 120 and the connecting portion 124. The superior portion 120 can include a blind bore 130 that receives the biasing member 114 and a first end of the axle post 112. The axle post 112 can have an annular channel 132 formed therearound. The axle post 112 and static axle 113 can collectively comprise a second hinge portion 134 having a second hinge axis 135. The inferior portion 122 can have a bore 136 that receives the bushing 116. The inferior portion 122 can have an anterior tang 140 having a superior or upper surface 141 and a posterior tang 142 having a superior or upper surface 143. As will be described, the axle post 112 is biased axially outwardly by the biasing member 114. The yoke 110 can be formed of cobalt-chromium molybdenum or other suitable biocompatible material. The bushing 116 can have an opening 138 and can be formed of non-metallic biocompatible material, such as PEEK. The bushing 116, being formed on non-metallic material can provide a suitable intermediate buffer between an otherwise metal on metal engagement between the post 70 and the bore 136 of the inferior portion 122 of the yoke 110.

Figure 12:
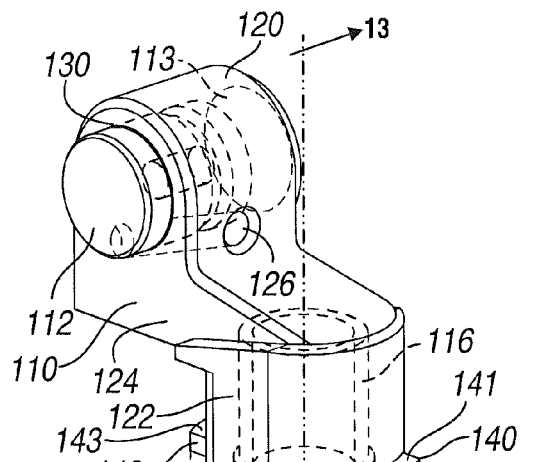
FIG. 12 is an exploded perspective anterior view of the yoke assembly and rotating tibial bearing.
Figure 12:
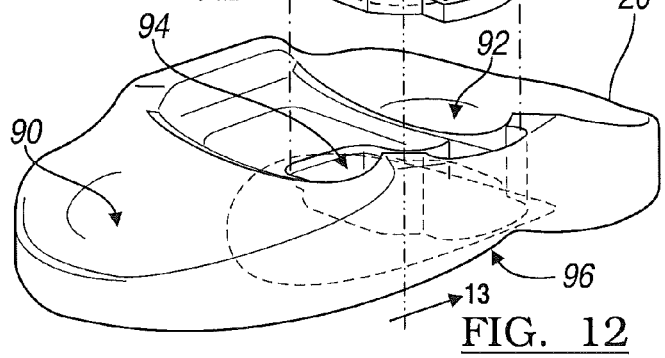

With reference now to FIGS. 12-20, one exemplary method for assembling the yoke assembly 22 with respect to the rotating tibial bearing 20 and tibial tray 52 will be described. At the outset, the yoke 110 can be located generally above or superiorly relative to the rotating tibial bearing 20 (FIG. 12). The respective anterior and posterior tangs 140 and 142 provided on the inferior portion 122 of the yoke 110 can then be rotationally aligned with the respective keyways 100 and 102 formed on the opening 94 of the rotating tibial bearing 20 (see FIG. 12). The yoke 110 can then be advanced downward or inferiorly, such that the anterior and posterior tangs 140 and 142 respectively pass through the keyways 100 and 102 until the tangs 140 and 142 reach a position below or inferiorly relative to the respective keyways 100 and 102 (see FIG. 13).

Figure 14:
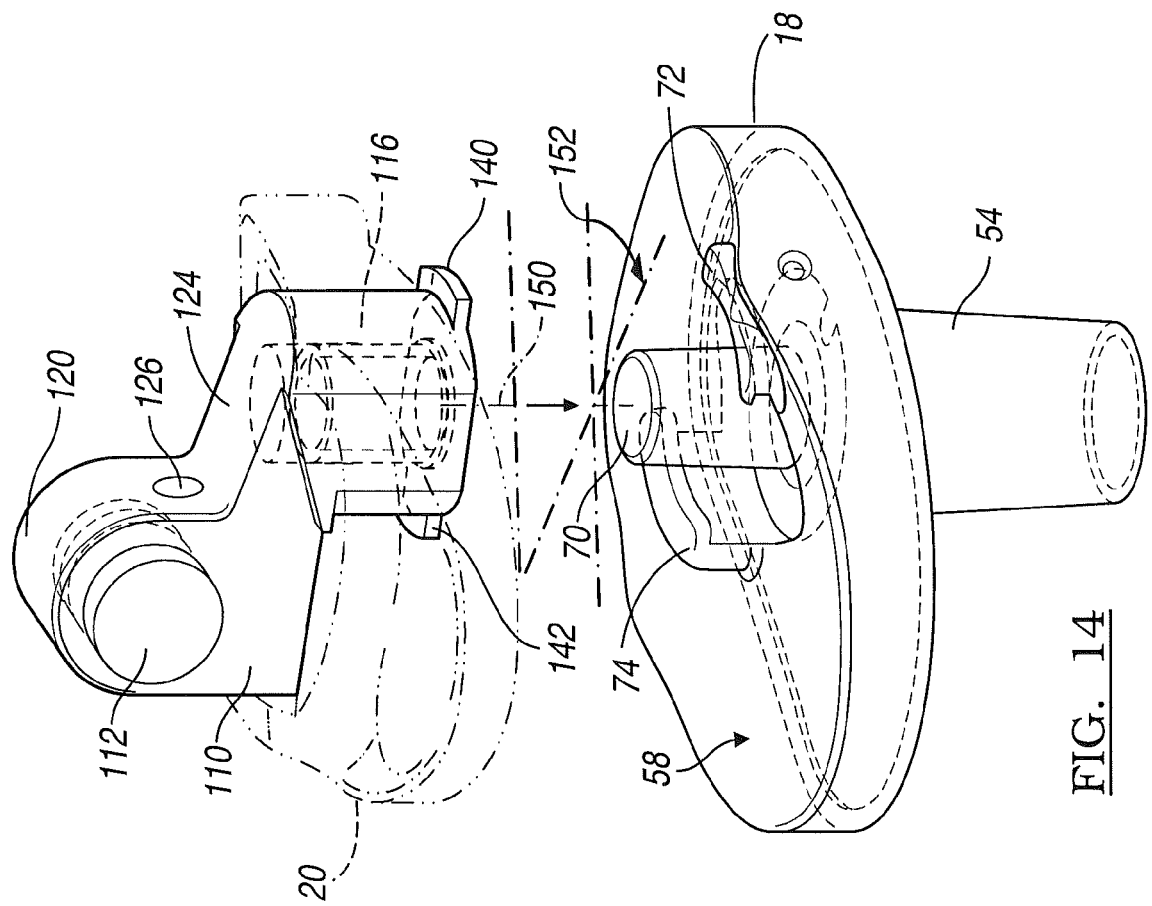
FIG. 14 is an exploded anterior perspective view of the tibial component and yoke assembly shown with the rotating tibial bearing in phantom and illustrating the yoke assembly rotated for alignment with the rotating tibial bearing during an assembly step.
Figure 13:
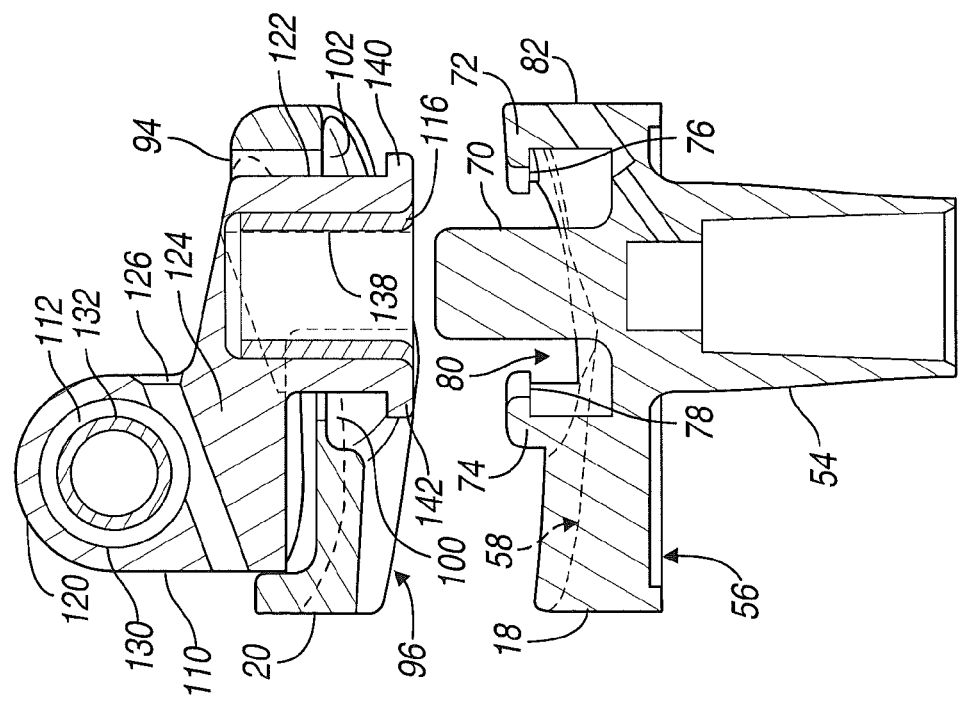
FIG. 13 is a cross-sectional view of the yoke assembly and rotating tibial bearing taken along lines 13-13 of FIG. 12.
Figure 15:
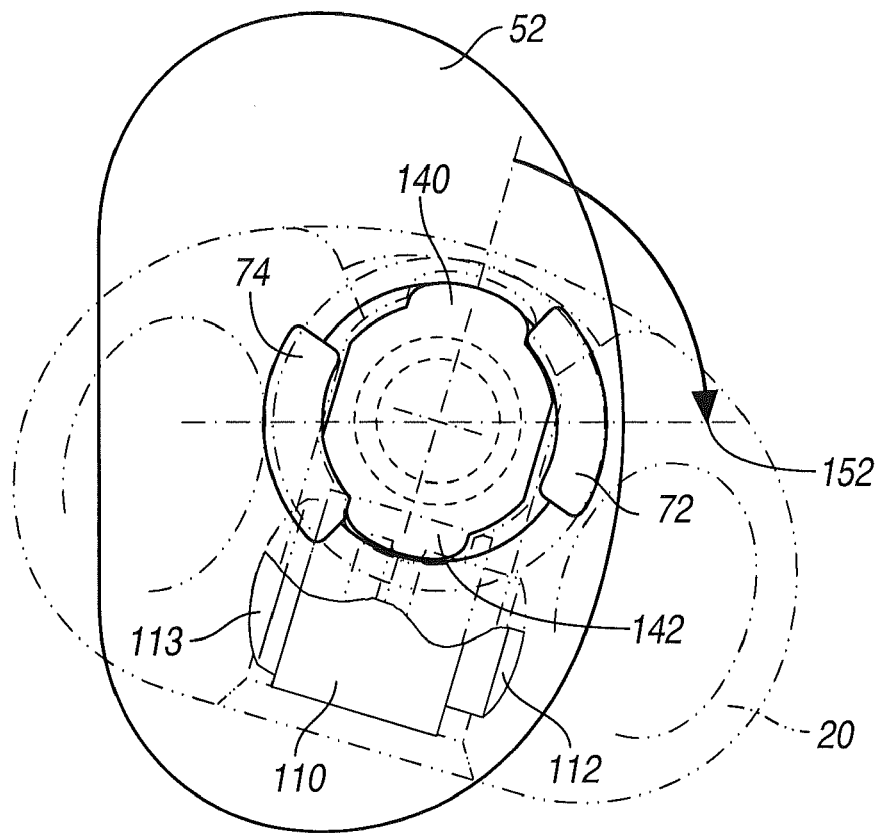
FIG. 15 is a superior view of the rotating tibial bearing and yoke assembly shown rotationally aligned with the rotating tibial bearing during assembly, the rotating tibial bearing shown in phantom and the yoke assembly shown in partial phantom.

At this point, the rotating tibial bearing 20 and yoke assembly 22 can be collectively located above or superiorly relative to the tibial component 18 as shown in FIG. 13. The post 70 of the tibial component 18 can then be axially aligned with the opening 138 of the bushing 116. With reference to FIGS. 14 and 15, the collective assembly of the rotating tibial bearing and yoke assembly 22 can be rotated about a bushing axis 150 extending longitudinally through the opening 138 of the bushing 116 to a position whereby the anterior and posterior tangs 140 and 142 are rotationally out of alignment with the respective anterior and posterior fingers 72 and 74 of the tibial tray 52. In one example, the yoke 110 can be rotated at an angle 152 that is between 70° and 75° (as best illustrated in FIG. 15). It is appreciated by those skilled in the art, however, that the configuration of the tangs 140 and 142, as well as the fingers 72 and 74 can be arranged differently to require a different angle while still reaching similar results. Once the yoke assembly 22 and the rotating tibial bearing 20 have been collectively rotated a sufficient amount about the bushing axis 150, they can be moved collectively downward or inferiorly, such that the post 70 is received by the opening 138 of the bushing 116.

Figure 16:
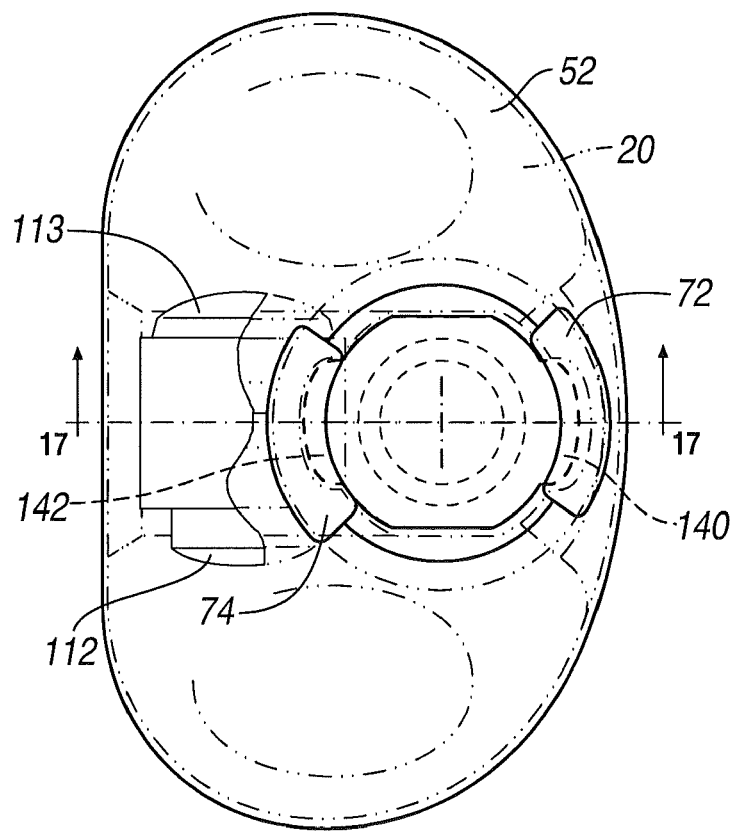
FIG. 16 is a superior view of the rotating tibial bearing and yoke assembly rotated into an assembled position relative to the tibial component.

Turning now to FIGS. 15 and 16, once the anterior and posterior tangs 140 and 142 of the yoke 110 have cleared (passed beyond) the first and second catch surfaces 76 and 78 of the anterior and posterior fingers 72 and 74 of the tibial tray 52, the yoke 110 and bearing tibial bearing 20 may be collectively rotated back to their original position (e.g., to a position where the angle 152 is about 0°) relative to the bushing axis 150 as shown in FIG. 16. In the position shown in FIG. 17, the anterior and posterior tangs 140 and 142 are captured below (inferiorly) the first and second catch surfaces 76 and 78 of the respective anterior and posterior fingers 72 and 74.

Figure 17:
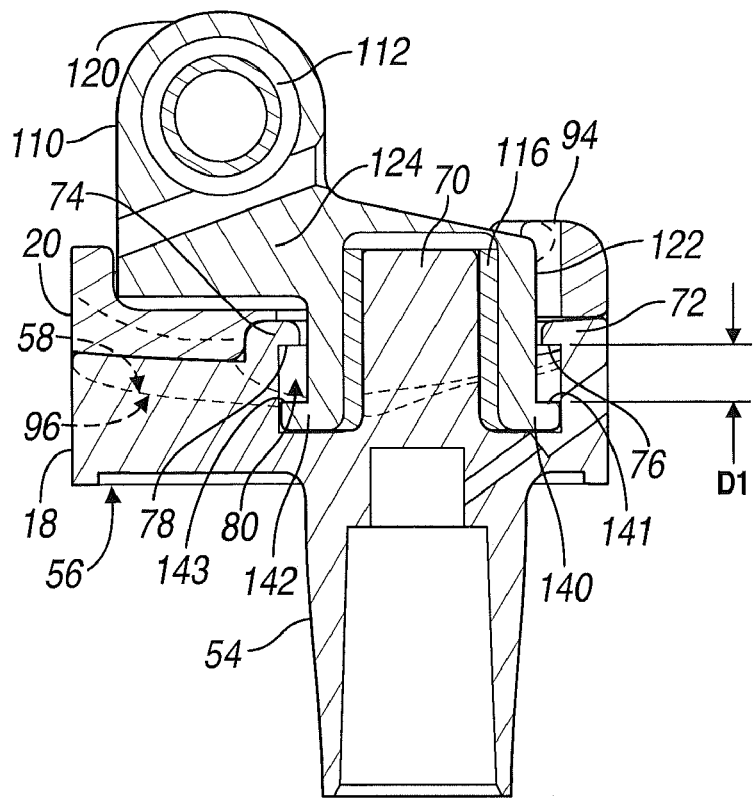
FIG. 17 is a cross-sectional view of the assembled yoke assembly, rotating tibial bearing and tibial component taken along lines 17-17 of FIG. 16.
Figure 18:
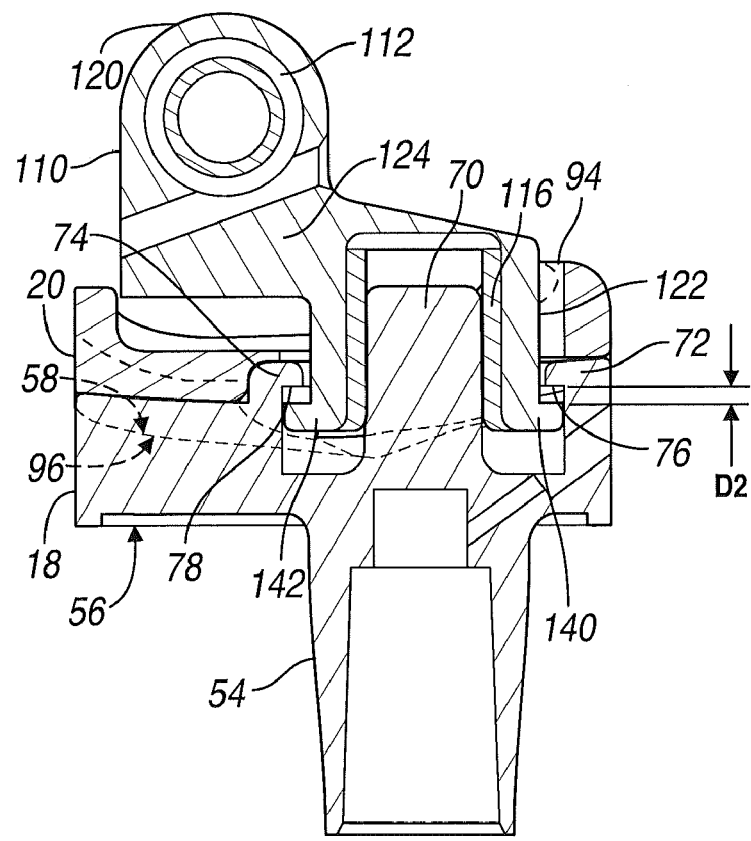
FIG. 18 is a cross-sectional view of the yoke assembly, rotating tibial bearing and tibial component of FIG. 17 shown with the yoke assembly advanced a distance superiorly.

With reference now to FIGS. 17 and 18, the yoke 110 can now be advanced (relative to the rotating tibial bearing 20) in a direction superiorly along the bushing axis 150 from a location shown in FIG. 17 to a location shown in FIG. 18. Explained in more detail, the upper surfaces 141 and 143 of the respective tangs 140 and 142 are offset a distance D1 from the respective first and second catch surfaces 76 and 78 as shown in FIG. 17. The yoke 110 can then be advanced superiorly (relative to the rotating tibial bearing 20) to a position as shown in FIG. 18 wherein the upper surfaces 141 and 143 of the respective anterior and posterior tangs 140 and 142 are offset a distance D2 from the first and second respective catch surfaces 76 and 78. As illustrated, D2 is less than D1. It is also important to recognize that D2 is greater than zero.

Figure 19:
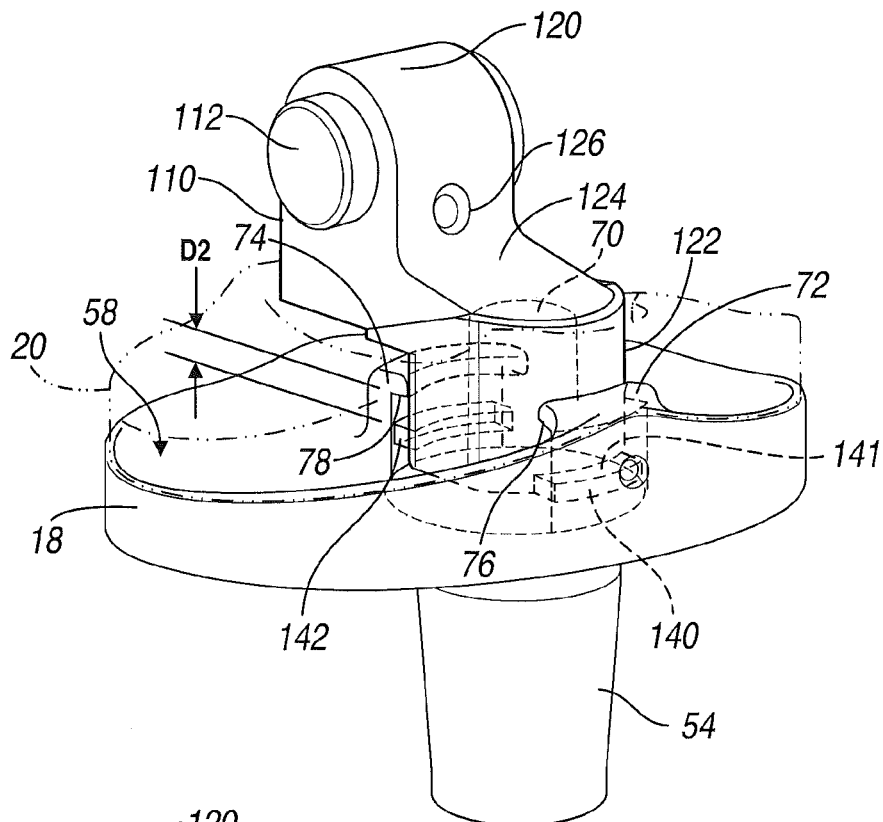
FIG. 19 is an anterior perspective view of the assembled yoke assembly, rotating tibial bearing and tibial component, shown with the rotating tibial bearing in phantom.
Figure 20:
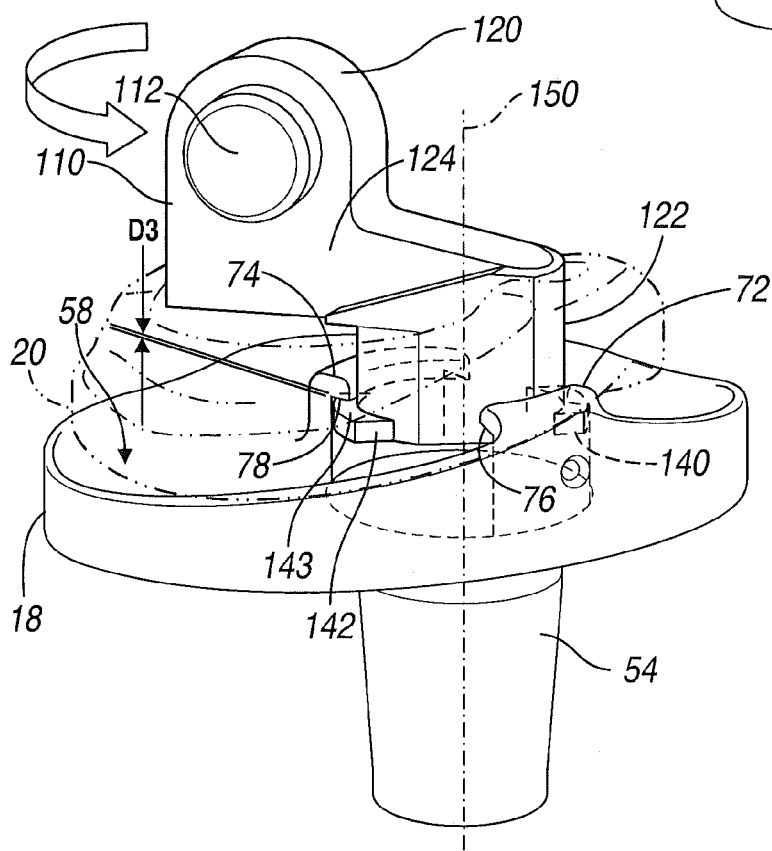
FIG. 20 is an anterior perspective view of the yoke assembly and rotating tibial bearing rotating along a bi-helical engagement surface provided between the rotating tibial bearing and the tibial component causing the rotating tibial bearing and yoke assembly to rise superiorly.
Figure 21:
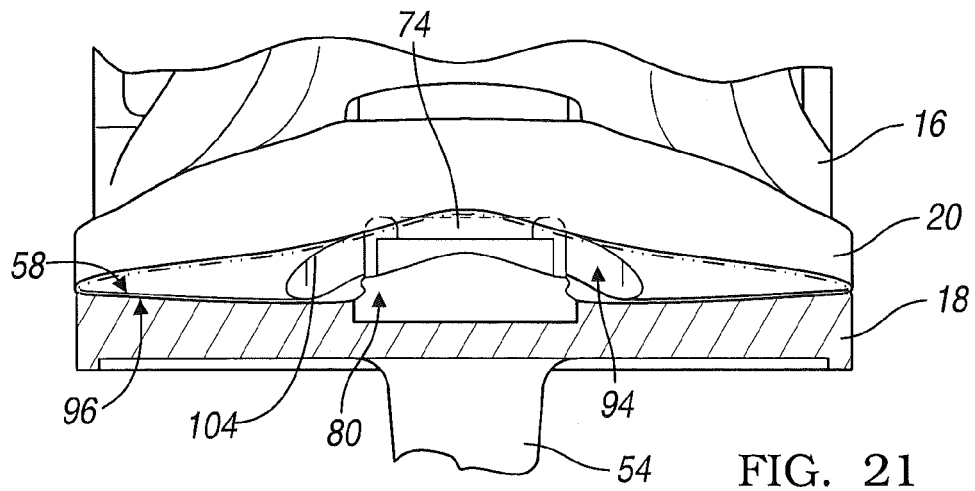
FIG. 21 is an anterior view of the bi-helical engagement surfaces of the rotating tibial bearing and tibial component shown with the tibial component in partial section view.
Figure 22:
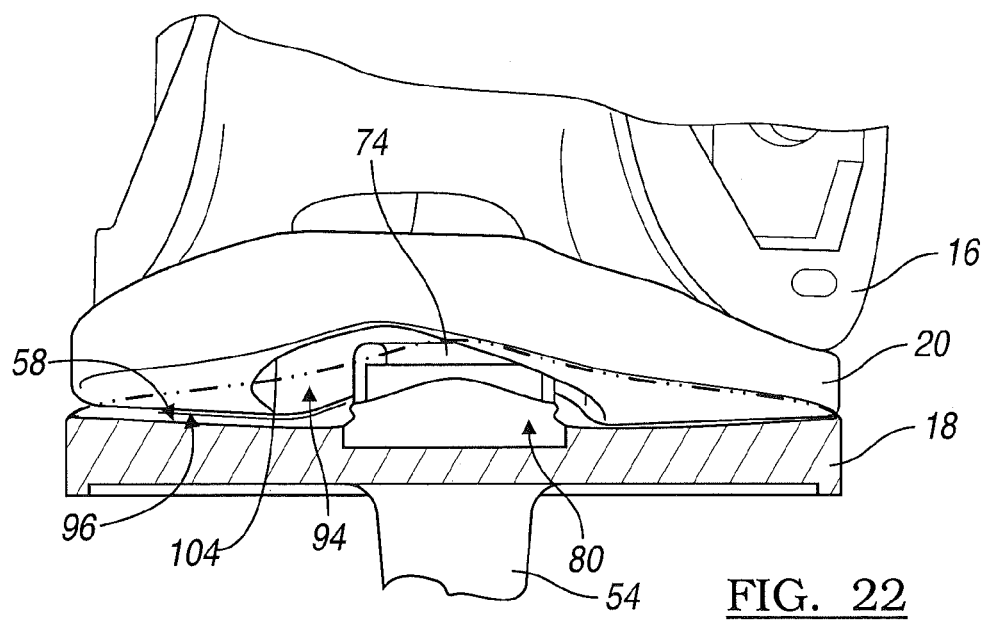
FIG. 22 is an anterior view of the rotating tibial bearing shown rotating with the femoral component about a vertical axis causing the rotating tibial bearing to rise superiorly as a result of slidable engagement between the bi-helical engagement surfaces of the tibial component and rotating tibial bearing.
Figure 26:
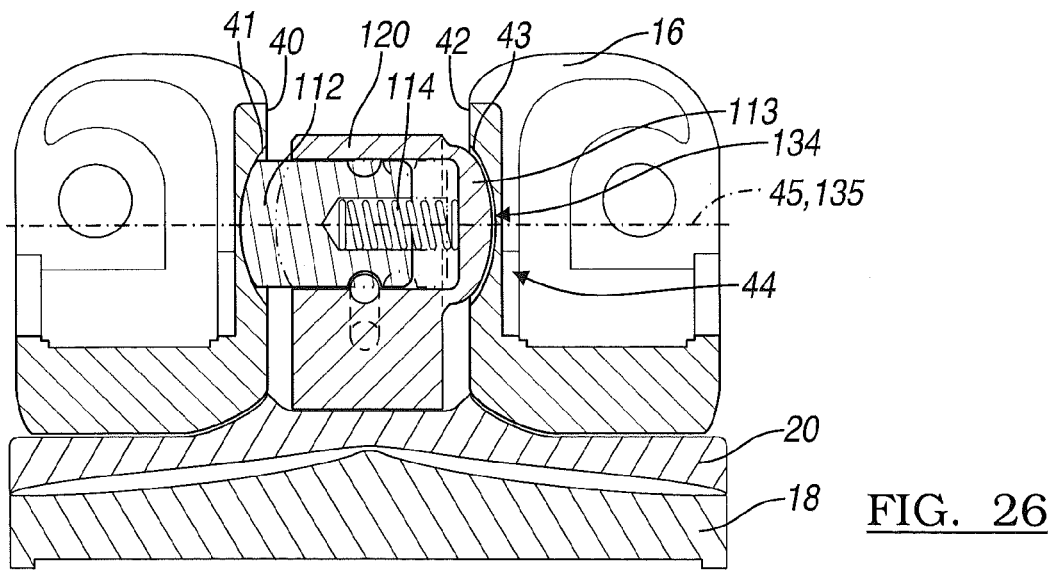
FIG. 26 is a partial cross-sectional view of the femoral component, the yoke assembly, the rotating tibial bearing and the tibial component taken along lines 26-26 of FIG. 23.
Figure 23:
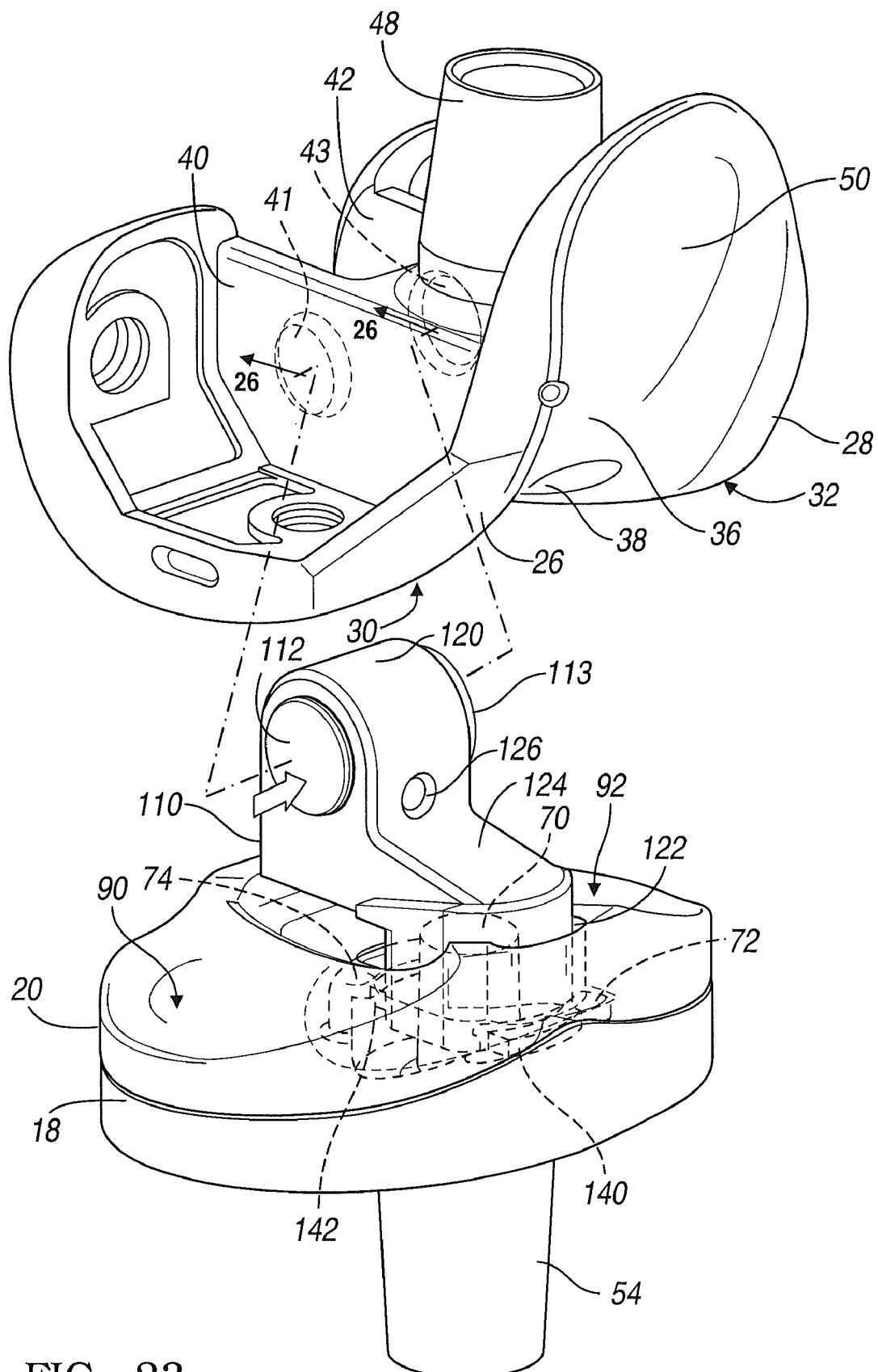
FIG. 23 is an exploded anterior view of the hinged knee joint prosthesis of FIG. 1 shown with the yoke aligned for receipt into the intercondylar recess of the femoral component.
Figure 24:
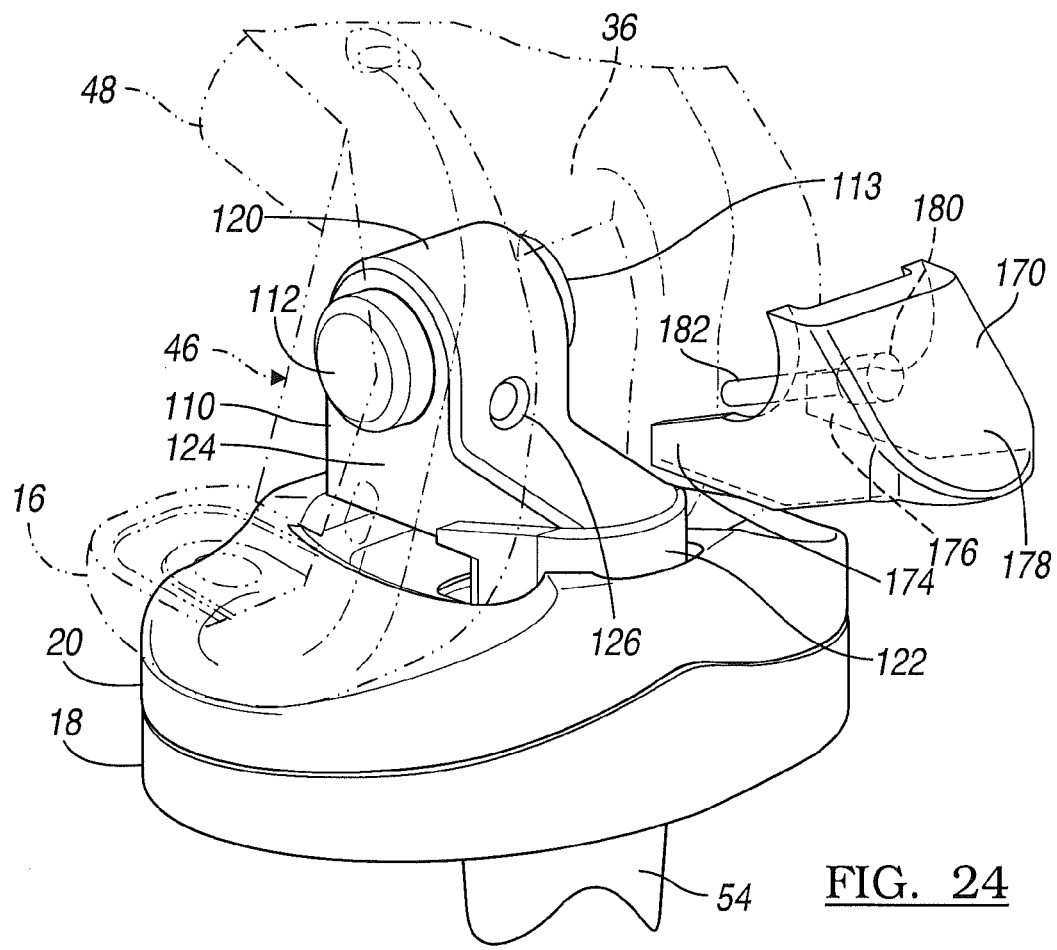
FIG. 24 is an anterior perspective view of the yoke being received by the intercondylar recess of the femoral component while the femoral component is in flexion and ready for receipt of a hyper-extension stop.

As shown in FIGS. 19 and 20, when the rotating tibial bearing 20 (and the yoke 110), rotate around the bushing axis 150 (i.e., around an axis extending in the superior/inferior direction) relative to the tibial component 18 from the position shown in FIG. 19 to the position shown in FIG. 20, the respective bi-helical superior surface 58 of the tibial tray 52 and the bi-helical inferior surface 96 of the rotating tibial bearing 20 slidably engage. In this way, the rotating tibial bearing 20 (and the yoke 110) rise superiorly relative to the tibial component 18, such that a distance D3 is now created between the upper surfaces 141 and 143 of the respective anterior and posterior tangs 140 and 142 and the first and second catch surfaces 76 and 78. As shown, D3 is less than D2. In one example as shown in FIG. 20, the respective bi-helical surfaces 58 and 96 can be configured, such that the rotating tibial bearing 20 (and the yoke 110) can rotate to a position, whereby the upper surfaces 141 and 143 of the respective anterior and posterior tangs 140 and 142 engage the first and second catch surfaces 76 and 78 (explained differently, to a position where D3 is zero).

The engagement of the upper surfaces of the tangs 140 and 142 with the first and second catch surfaces 76 and 78 can inhibit subluxation and further rotation of the rotating tibial bearing 20 (and the yoke 110). Once implanted, the only loading the tangs 140 and 142 experience is when they engage the catch surfaces 76 and 78 (i.e., prevention of subluxation). Other loads including varus, valgus, hyper-extension, flexion, and anterior/posterior drawer forces are transferred from the femur 14 through the yoke 110 to the tibia 12 by way of the post 70 of the tibial tray 52.

With reference now to FIGS. 23-26, assembly of the femoral component 16 to the yoke 110 according to one example will now be described. The superior portion 120 of the yoke 110 can be advanced to an area between the first and second lateral sidewalls 40 and 42 of the femoral component 16. The axle post 112 and static axle 113 can then be aligned with the respective first and second bushings 41 and 43. In one example, the axle post 112 can be depressed inward along the second hinge axis 135 (to an installation position shown in phantom line in FIG. 26) against the bias of the biasing member 114 by the surgeon and/or as a result from sliding along the first lateral sidewall 40 of the femoral component 16. Once the axle post 112 and static axle 113 are axially aligned with the first and second bushings 41 and 43, the bias of the biasing member 114 will urge the axle post 112 axially outwardly (to an assembled position shown in solid line in FIG. 26), such that the respective axle post 112 and static axle 113 nest within the respective concave surfaces provided by the first and second bushings 41 and 43 (see FIG. 26). The first and second hinge portions 44 and 134 are now assembled such that the respective first and second hinge axes 45 and 135 are substantially collinear. The femoral component 16 can now rotate about the second hinge axis 135.

Figure 25:
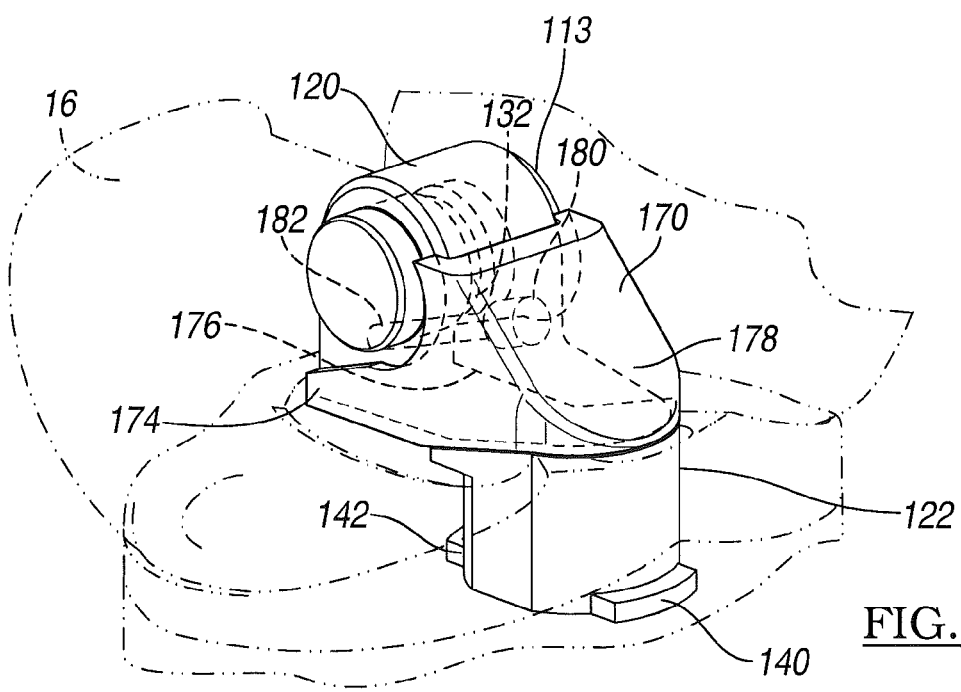
FIG. 25 is a partial anterior perspective view of the yoke assembly assembled with the femoral component and shown with the hyper-extension stop assembled onto the anterior side of the yoke.
Figure 27:
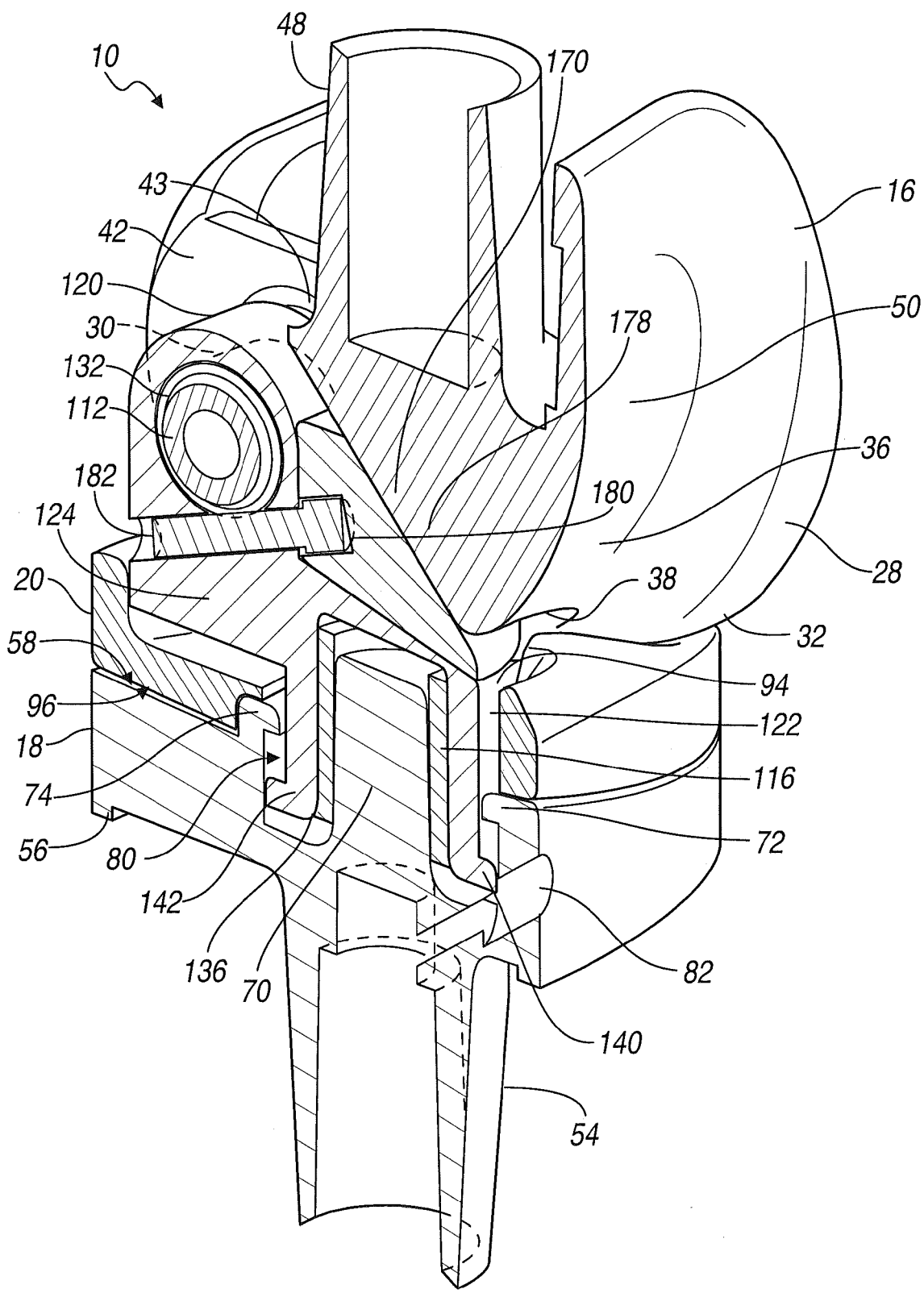
FIG. 27 is a cross-sectional view of the hinged knee joint prosthesis taken along lines 27-27 of FIG. 1.

Next, a hyper-extension stop 170 can be advanced (posteriorly) to a location that engages the yoke 110 (FIG. 25). The hyper-extension stop 170 can generally comprise lateral wings 174 and 176 and a sloped anterior portion 178. An opening 180 can be formed through the sloped anterior portion 178 of the hyper-extension stop 170. A pin 182 can be separately formed or integrally molded to the opening 180 of the hyper-extension stop 170. During assembly, the pin 182 can be located through the passage 126 formed in the connecting portion 124 of the yoke 110. In one example, the pin 182 can also be located at the annular channel 132 of the axle post 112. In one example, the hyper-extension stop 170 can be advanced into engagement with the yoke 110, while the femoral component 16 (and the femur 14) are in flexion relative to the tibial component 18 (and tibia 12). The hyper-extension stop 170 can engage the intercondylar portion 36 and therefore inhibit a hyper-extension of the tibia 12 relative to the femur 14. Furthermore, engagement with the pin 182 with the axle 112 of the yoke assembly 22 (at channel 132) inhibits inferior movement of the yoke 110. As a result, the anterior and posterior tangs 140 and 142 are precluded from attaining the distance D1 (FIG. 17) from the fingers 72 and 74. Therefore, the anterior and posterior tangs 140 and 142 cannot rotate out of alignment with the fingers 72 and 74 to a position shown in FIG. 15 that could potentially dislocate the yoke 110 from the tibial tray 20. The present configuration of the knee joint prosthesis 10 allows it to be easily applied to a range of tibial tray sizes.

Figure 28:
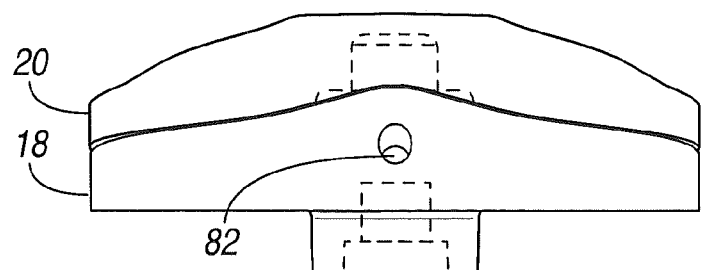
FIG. 28 is an anterior view of the rotating tibial bearing and tibial component coupled to an offset stem adapter and stem according to one example of the present teachings.
Figure 28:
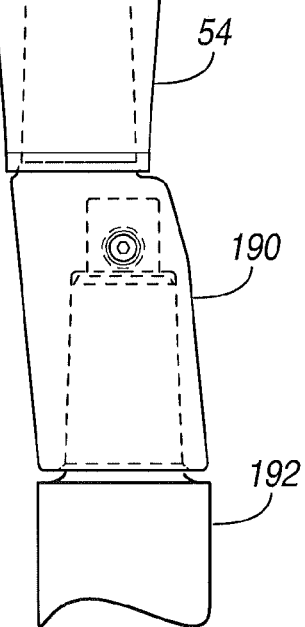
Figure 29:
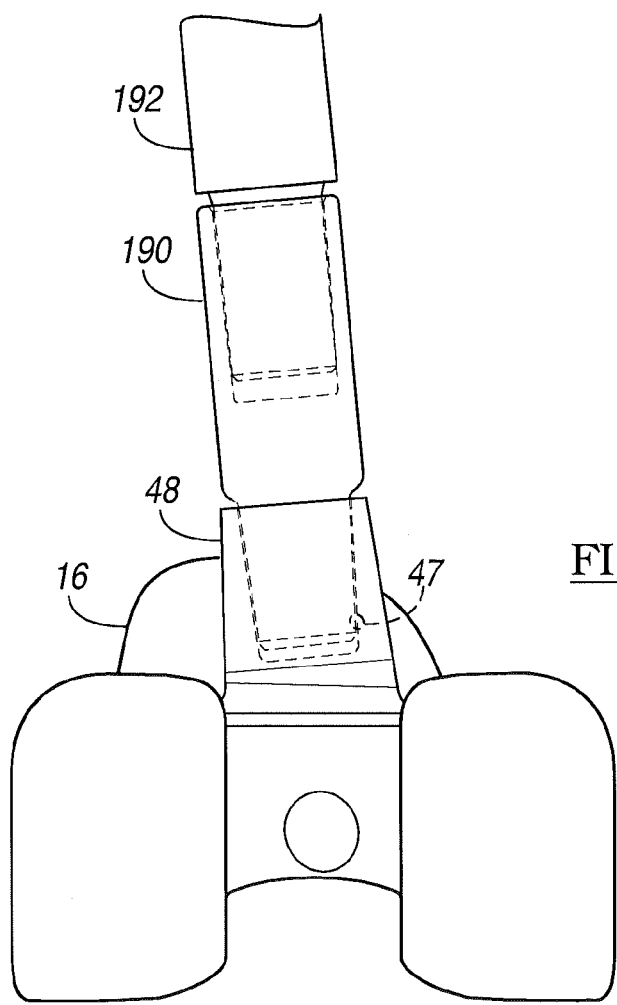
FIG. 29 is a posterior view of the femoral component shown operatively coupled with a stem adapter and stem according to additional features of the present teachings.

As shown in FIGS. 28 and 29, the tibial component 18 and femoral component 16 can both be configured to selectively couple with various adapters and/or stems such as provided in the Vanguard Complete Knee System described above. For example, an offset adapter 190 and stem 192 are shown cooperatively coupled with the tibial component 18 (FIG. 28) and femoral component (FIG. 29), respectively.

Turning now to FIGS. 30-32, a hinged bearing adapter 218 constructed in accordance to one example of the present teachings will be described. The hinged bearing adapter 218 can be used during a revision procedure to intraoperatively couple with a standard modular tibial base or tray 220. It will be appreciated that the hinged bearing adapter 218 can be formed for intraoperatively connecting with any standard tibial tray for converting a conventional modular tibial tray into a hinged knee joint prosthesis. One exemplary tibial tray is commercially available from Biomet Manufacturing Corp. of Warsaw, Ind. as components of the Maxim® Total Knee System, which includes various sizes and configurations of tibial components for different patient requirements. By converting an existing modular tibial tray (such as 220) into a tibial tray suitable for cooperation with a hinge, removal of the existing modular tibial tray is unnecessary. Therefore, a less invasive procedure can be performed minimizing trauma, bone and tissue loss, etc.

Prior to description of the hinged bearing adapter 218, a brief description of the exemplary tibial tray 220 will now be described. The tibial tray 220 can include a generally flat superior surface 224 having a pair of posts 226 and 228 integrally formed at an anterior edge thereof. A retaining rail 230 can extend superiorly from a posterior edge of the tibial tray 220. The posts 226 and 228 can both have an anterior groove 232 and a posterior groove 234, respectively. The retaining rail 230 can have a transverse groove 240 formed on an inwardly facing surface.

The hinged bearing adapter 218 can generally provide a similar superior profile as described above with respect to the tibial component 18. As can be appreciated, the hinged bearing adapter 218 can cooperate with the components of the hinged knee joint prosthesis 10 as described above. The hinged bearing adapter 218 can have a bi-helical superior surface 244. The bi-helical superior surface 244 can include a raised middle portion 246, a first depression 248, and a second depression 250, wherein the respective first and second depressions 248 and 250 are formed on either side of the raised middle portion 246. A superiorly extending post 252 can be centrally formed on the hinged bearing adapter 218. An anterior finger 254 and a posterior finger 256 can extend generally superiorly from the raised middle portion 246 of the hinged bearing adapter 218. The anterior finger 254 can have a first catch surface 260. The posterior finger 256 can have a second catch surface 262. A channel 264 can be arranged at an annular recess provided between the superiorly extending post 252 and the respective anterior and posterior fingers 254 and 256.

The hinged bearing adapter 218 can have a locking bar 270 slidably received within a bore 272 extending in a posterior direction through the hinged bearing adapter 218. A locking screw 274 can threadably cooperate with the bore 272 during an assembly step as will be described. The hinged bearing adapter 218 can also have a pair of engagement surfaces 276 formed thereon for selectively engaging the posterior grooves 234 on the posts 226 and 228 of the tibial tray 220. A pair of voids 277 can be provided on an anterior portion for accommodating the respective posts 226 and 228 of the tibial tray 220. Similarly, the hinged bearing adapter 218 can have a posterior void 278 configured to receive the retaining rail 230 of the tibial tray 220.

With specific reference now to FIGS. 31 and 32, an exemplary sequence of intraoperatively connecting the hinged bearing adapter 218 to the tibial tray 220 will now be described. Initially, the hinged bearing adapter 218 can be tilted generally anteriorly and advanced toward the flat superior surface 224 of the tibial tray 220. Once the respective engagement surfaces 276 locate at the posterior grooves 234 of the tibial tray 220, the hinged bearing adapter 218 can be rotated generally posteriorly from the position shown in FIG. 31 to the position shown in FIG. 32. The posterior rotation of the hinged bearing adapter 218 can facilitate engagement of the engagement surfaces 276 into an interlocking relationship with the posterior grooves 234 of the respective posts 226 and 228. The locking screw 274 can then be threadably advanced into the bore 272 to advance the locking bar 270 in a direction generally posteriorly and into a nesting position within the transverse groove 240 of the retaining rail 230. The hinged bearing adapter 218 is now securably attached to the tibial tray 220.

Figure 33:
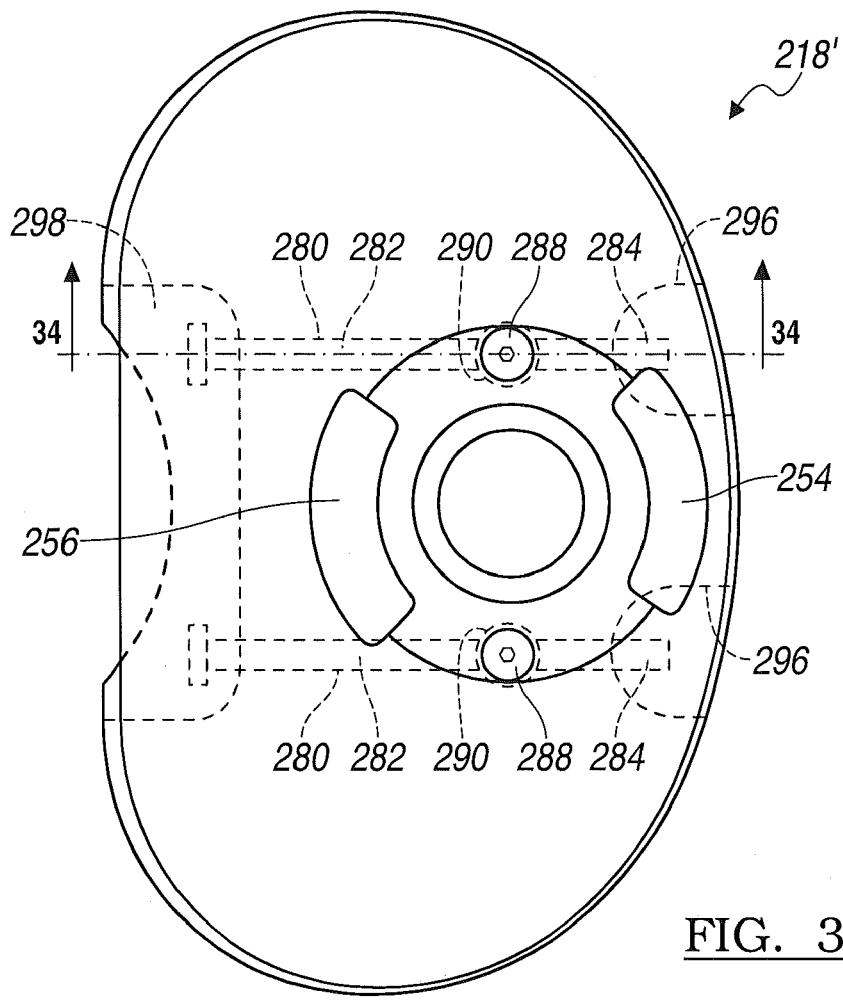
FIG. 33 is a superior view of a hinged bearing adapter constructed in accordance to another example of the present teachings and shown in an assembled position with a modular tibial tray.
Figure 34:
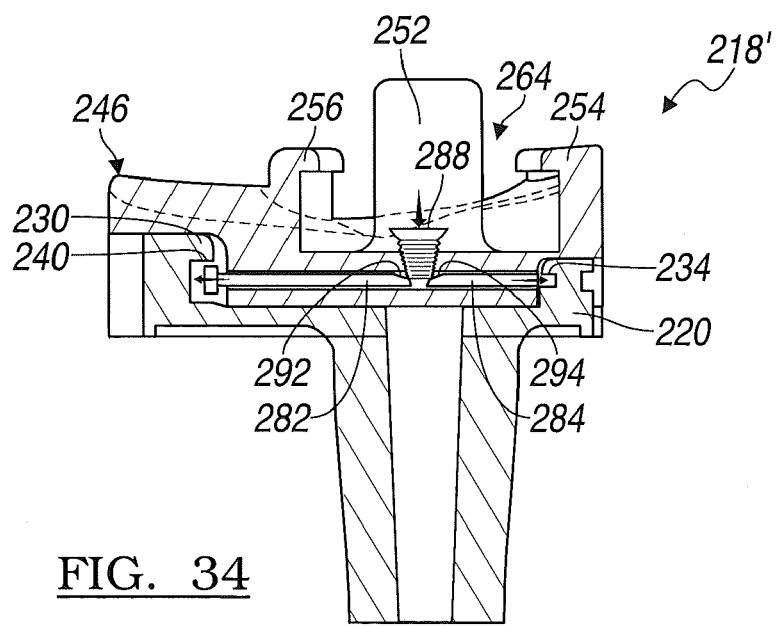
FIG. 34 is a cross-sectional view of the hinged bearing adapter and tibial tray taken along lines 34-34 of FIG. 33.

With reference now to FIGS. 33 and 34, another hinged bearing adapter 218' constructed in accordance to additional features of the present teachings will be described. Except as otherwise described, the hinged bearing adapter 218' can be constructed similarly to the hinged bearing adapter 218 described above with relation to FIGS. 30-32. The hinged bearing adapter 218' can be used to intraoperatively connect with the tibial tray 220 during a revision knee procedure when it is desired to convert a modular tibial tray (such as the exemplary tibial tray 220 illustrated in the drawings) into a hinged knee joint prosthesis.

The hinged bearing adapter 218' can have a pair of posteriorly extending bores 280 that each receive a pair of locking bars 282 and 284, respectively. A pair of fasteners 288 can be received in bores 290 that intersect with the respective bores 280. The respective locking bars 282 and 284 can include angled engagement surfaces 292 and 294, respectively. The hinged bearing adapter 218' can have a pair of void portions 296 arranged on an anterior portion for accommodating the respective posts 226 and 228 of the tibial tray 220. Similarly, the hinged bearing adapter 218' can have a posterior void portion 298 configured to receive the retaining rail 230 of the tibial tray 220.

During assembly, the hinged bearing adapter 218' can be advanced inferiorly toward the flat superior surface 224 of the tibial tray 220, such that the posts 226 and 228 are received by the void portions 296 and the retaining rail 230 is received by the posterior void portion 298. The fasteners 288 are then threadably advanced driven into the respective bores 290, such that they slidably advance along the angled surfaces 292 and 294 of the respective locking bars 282 and 284. This action causes the locking bars 282 to advance posteriorly into engagement with the transverse groove 240 of the retaining rail 230. This action also causes concurrent movement of the locking bars 284 to advance anteriorly into engagement with the posterior grooves 234 of the posts 226 and 228.

Figure 35:
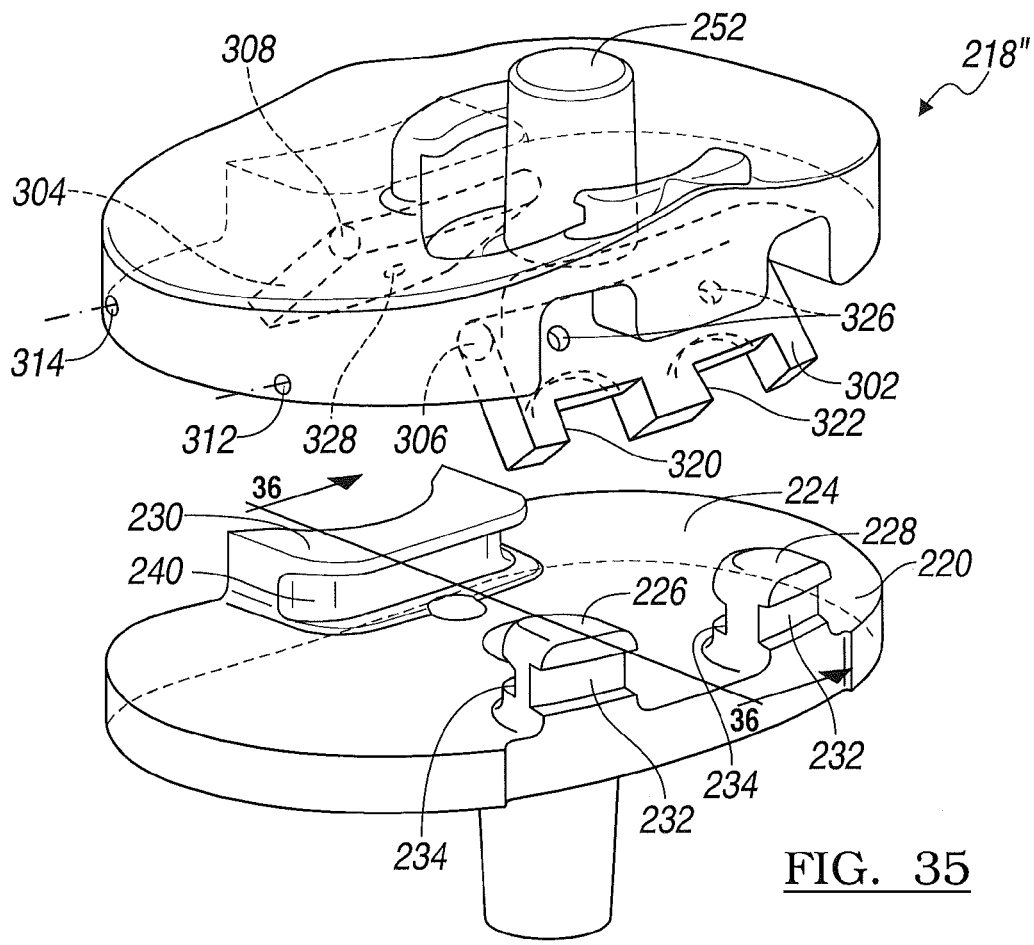
FIG. 35 is an exploded anterior perspective view of another hinged bearing adapter constructed in accordance to additional features of the present teachings and shown with a modular tibial tray 220.
Figure 36:
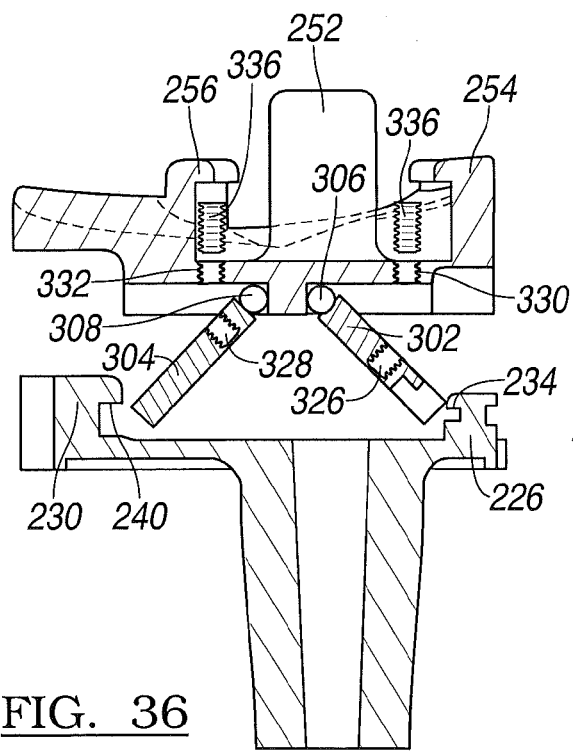
FIG. 36 is a cross-sectional view of the hinged bearing adapter and modular tibial tray taken along line 36-36 of FIG. 35.
Figure 37:
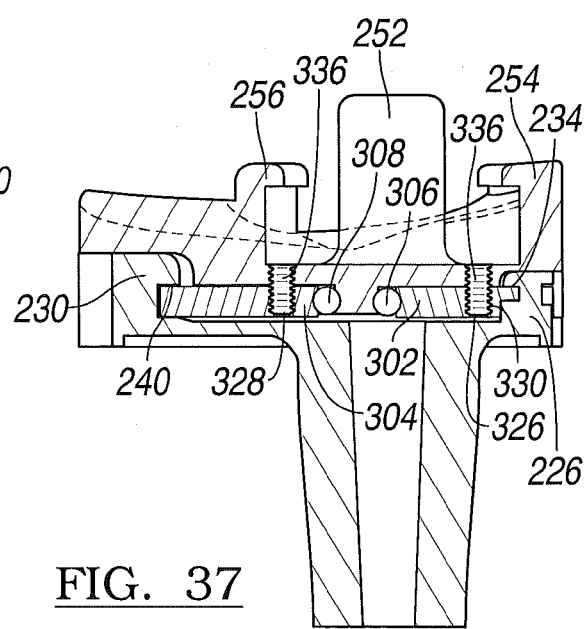
FIG. 37 is a cross-sectional view of the hinged bearing adapter and modular tibial tray of FIG. 36 and shown with a pair of hinged portions locked in an assembled position relative to the modular tibial tray.

With reference now to FIGS. 35-37, another hinged bearing adapter 218" constructed in accordance to additional features of the present teachings will be described. Except as otherwise described, the hinged bearing adapter 218" can be constructed similarly to the hinged bearing adapter 218 described above with relation to FIGS. 30-32. The hinged bearing adapter 218" can be used to intraoperatively connect with the tibial tray 220 during a revision knee procedure when it is desired to convert a modular tibial tray (such as the exemplary tibial tray 220 illustrated in the drawings) into a hinged knee joint prosthesis.

The hinged bearing adapter 218" can include first and second hinge portions 302 and 304. The hinge portions 302 and 304 can rotate about respective axles 306 and 308, respectively. A pair of passages 312 and 314 can be formed through the hinged bearing adapter 218" for receipt of the respective axles 306 and 308 during a manufacturing step.

The first hinge portion 302 can include a pair of notch portions 320 and 322 for cooperating with the respective posts 226 and 228 during intraoperative assembly of the hinged bearing adapter 218" to the tibial tray 220. First and second throughbores 326 can be formed through the first hinge portion 302. Similarly, a throughbore 328 can be formed through the second hinge portion 304. A complementary pair of passages 330 can be formed through the hinged bearing adapter 218" that align coaxially with the throughbores 326 in an installed position as will be described. Similarly, an opening 332 can be formed through the hinged bearing adapter 218" for aligning coaxially with the throughbore 328 of the second hinge portion 304 in an assembled position as will be described. Set screws 336 can be provided for aligning with the respective passages 330 and 332 and the throughbores 326 and 328.

During an exemplary assembly sequence, the hinged bearing adapter 218" can be advanced inferiorly toward the flat superior surface 224 of the tibial tray 220, such that the first hinge portion 302 locates into an interlocked position with the anterior grooves 234 of the first and second posts 226 and 228, respectively. Similarly, the second hinge portion 304 can locate into the transverse groove 240 of the retaining rail 230. As the hinged bearing adapter 218" is further advanced inferiorly, the first hinge portion 302 rotates about the hinge axle 306 in a counterclockwise direction (as viewed in FIG. 36) while the second hinge portion 304 rotates about the hinge axle 308 in a clockwise direction until reaching a generally horizontal position relative to the flat superior surface 224 of the tibial tray 220 as shown in FIG. 37.

The set screws 336 can then be threadably advanced through the respective passages 330 and 332 to threadably mate with the throughbores 326 and 328 to effectively lock the first and second hinge portions 302 and 304 in a closed position and locked relative to the tibial tray 220. It is appreciated that the first and second hinge portions 302 and 304 can be constructed differently. Likewise, it is appreciated that the interlocking feature may be achieved with only a single hinge or alternatively additional hinge portions. Likewise, the location and configuration of the respective passages 330 and 332 is merely exemplary and other locations may be additionally or alternatively provided. Moreover, other configurations may be implemented for selectively locking the respective first and second hinge portions 302 and 304 in the locked position shown in FIG. 37.

As used herein, the terms superior, superiorly, superior direction are used to generally refer to the anatomical meaning, such as higher in place or position or generally situated above. Similarly, the terms inferior, inferiorly, inferior direction are used to generally refer to the anatomical meaning, such as lower in place or position or generally situated below.

Figure 38:
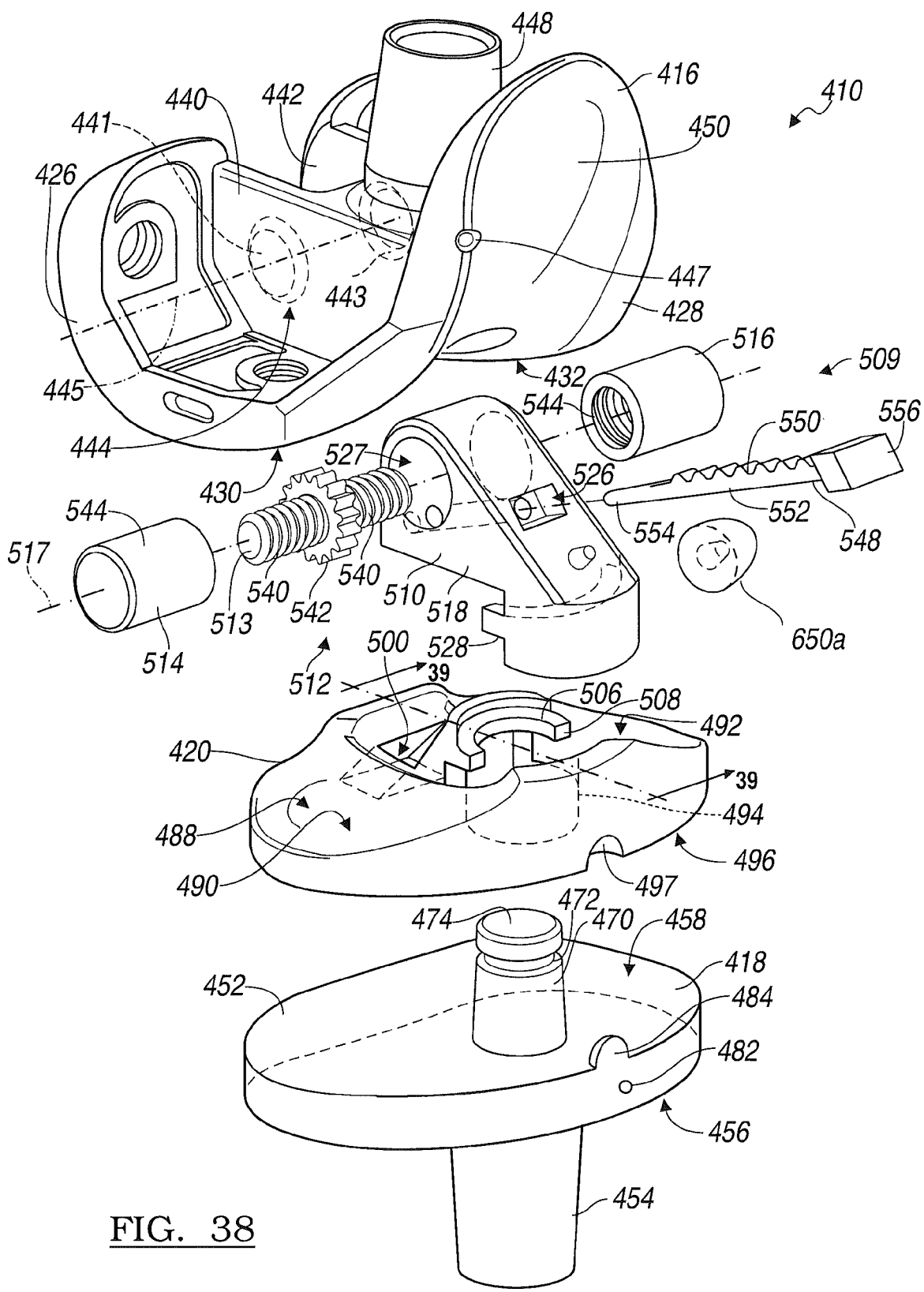
FIG. 38 is an exploded anterior view of a knee prosthesis system constructed in accordance to additional features of the present teachings.
Figure 51:
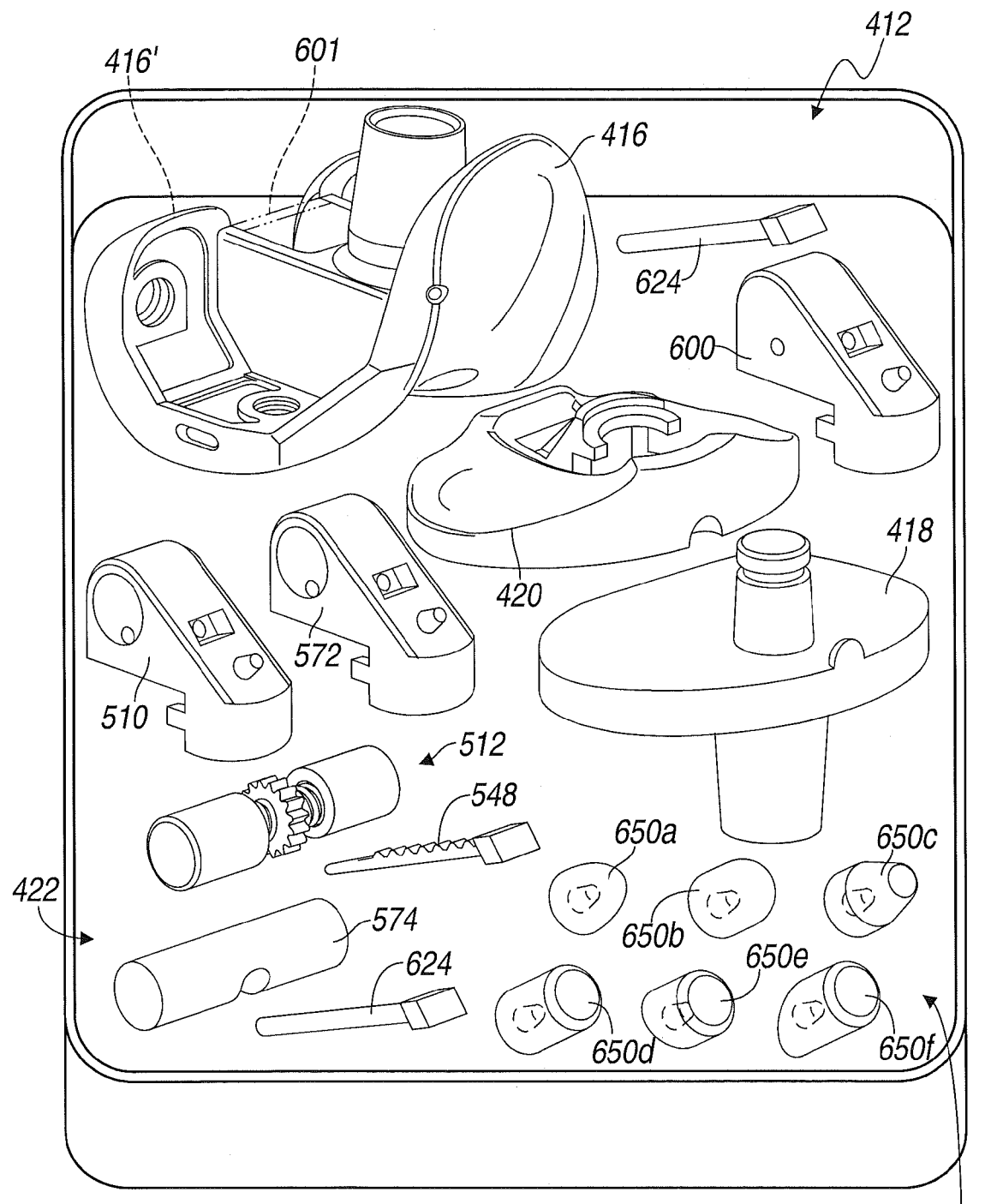
FIG. 51 is a knee joint prosthesis kit constructed in accordance with one example of the present teachings.

With initial reference to FIGS. 38 and 51, a knee joint prosthesis system constructed in accordance to another example of the present teachings is shown and identified at reference numeral 410. The knee joint prosthesis system 410 is generally shown as a hinged knee joint prosthesis system 410, which is designed to provide adequate stability in case of moderate deterioration or instability of the human knee. The knee joint prosthesis system 410 illustrated in FIG. 38 can be secured to a tibia and a femur, such as of a surgically resected left knee joint shown and described above with respect to FIG. 1. The knee joint prosthesis system 410 can generally include a kit 412 (FIG. 51) having a femoral component 416, a femoral component 416', a tibial component 418, a tibial bearing 420 and a kit of yoke assemblies 422. The femoral component 410 is shown as a left femoral component with the understanding that a suitable right knee joint prosthesis can be similarly constructed. The kit 412 can also include similar components having different sizes.

Figure 45:
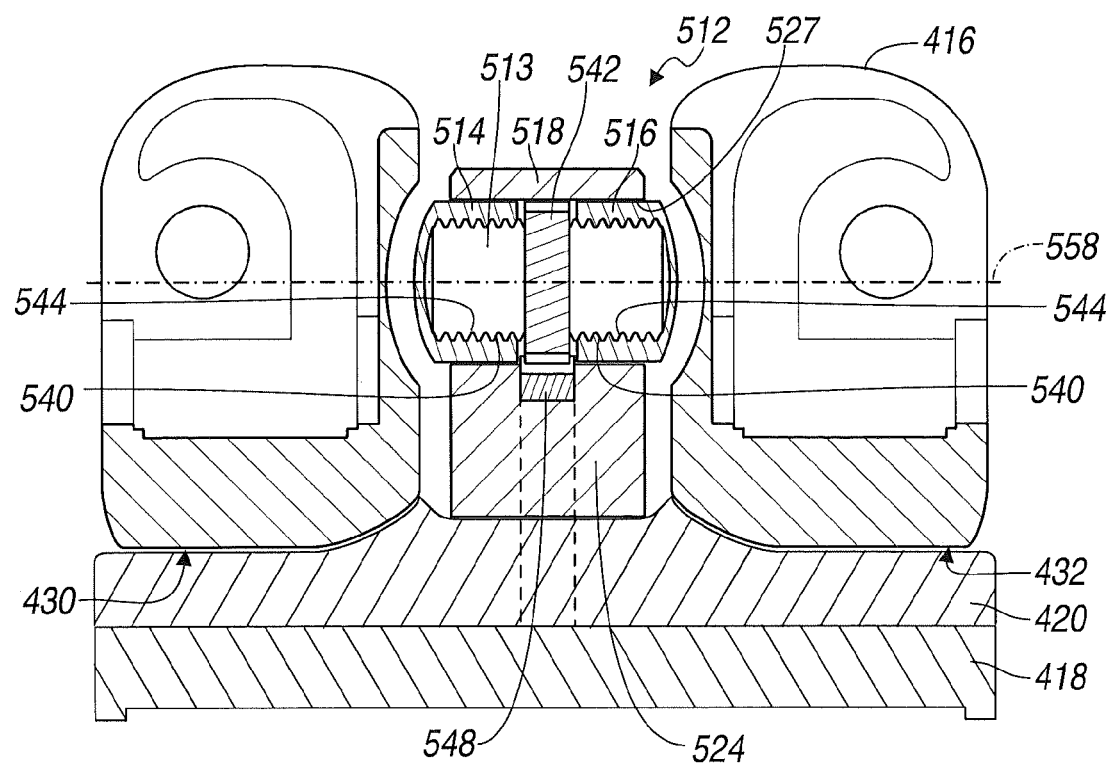
FIGS. 45 and 46 are sectional views of the knee joint prosthesis system shown during an assembly sequence and corresponding to the views shown in FIGS. 43 and 44 where an axle assembly advances outwardly into engagement with the femoral component.
Figure 46:
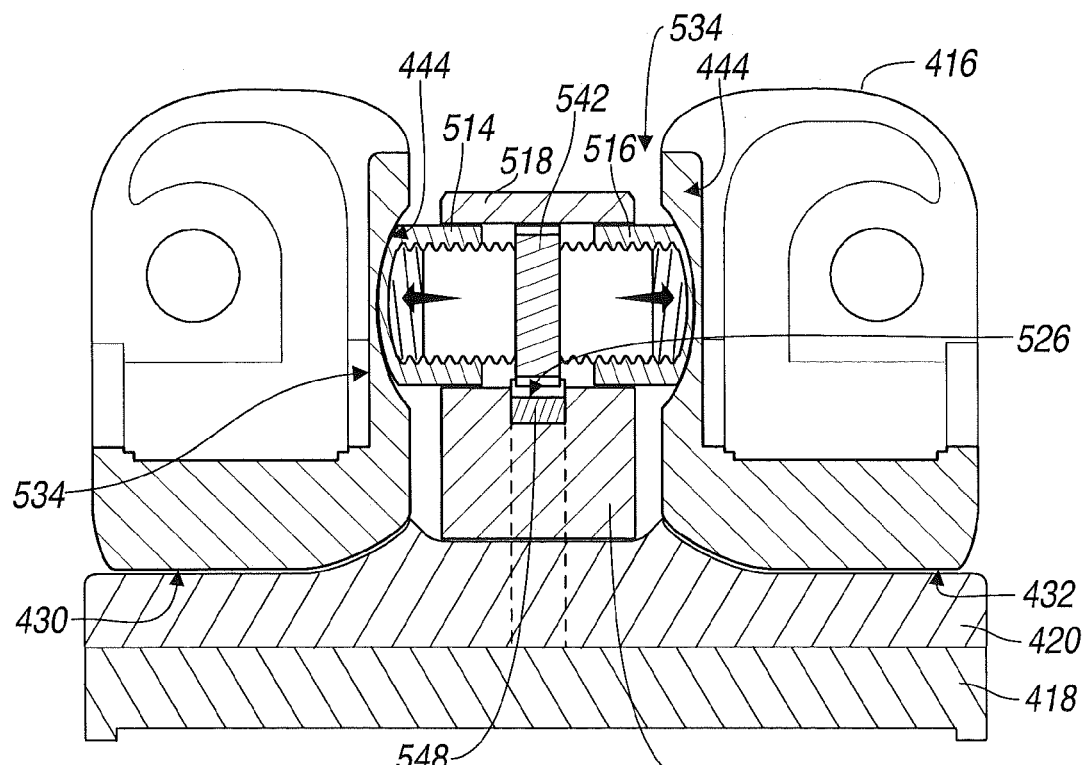

With continued reference to FIG. 38 and additional reference now to FIGS. 45 and 46, the femoral component 416 will be further described. The femoral component 416 can be constructed similar to the femoral component 16 illustrated in FIG. 1 and described above. While not specifically described again, like reference numerals increased by 400 have been used to identify similar features on the femoral component 416.

Figure 39:
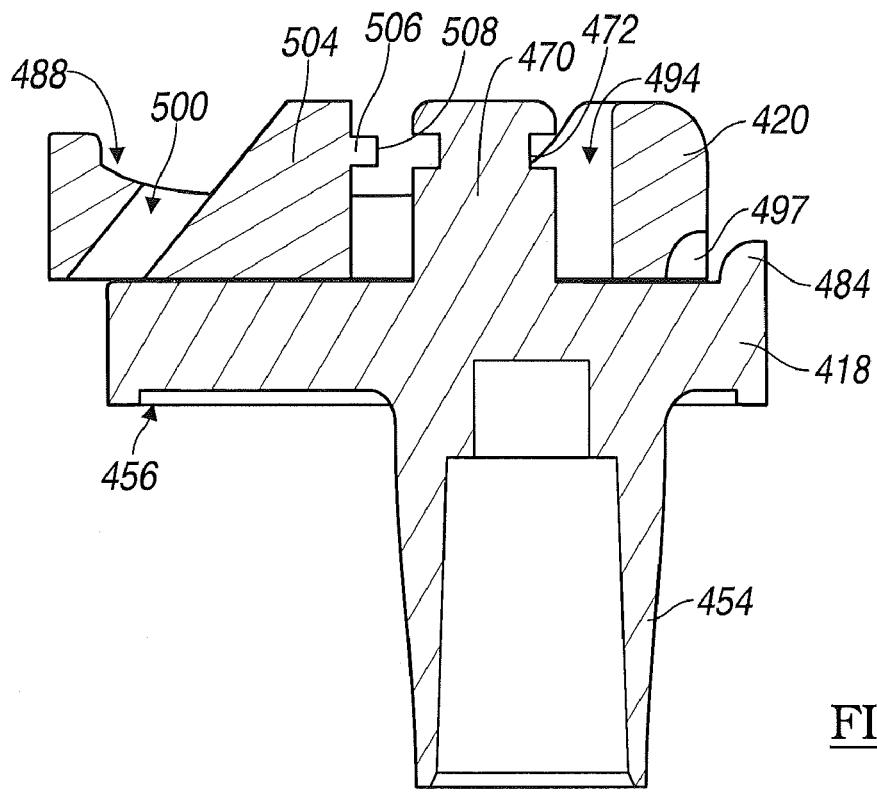
FIG. 39 is a cross-sectional view of the tibial bearing and tibial tray of the knee joint prosthesis taken along line 39-39 of FIG. 38 and shown with the bearing located on a superior bearing engaging surface of the tibial tray during an assembly step.
Figure 40:
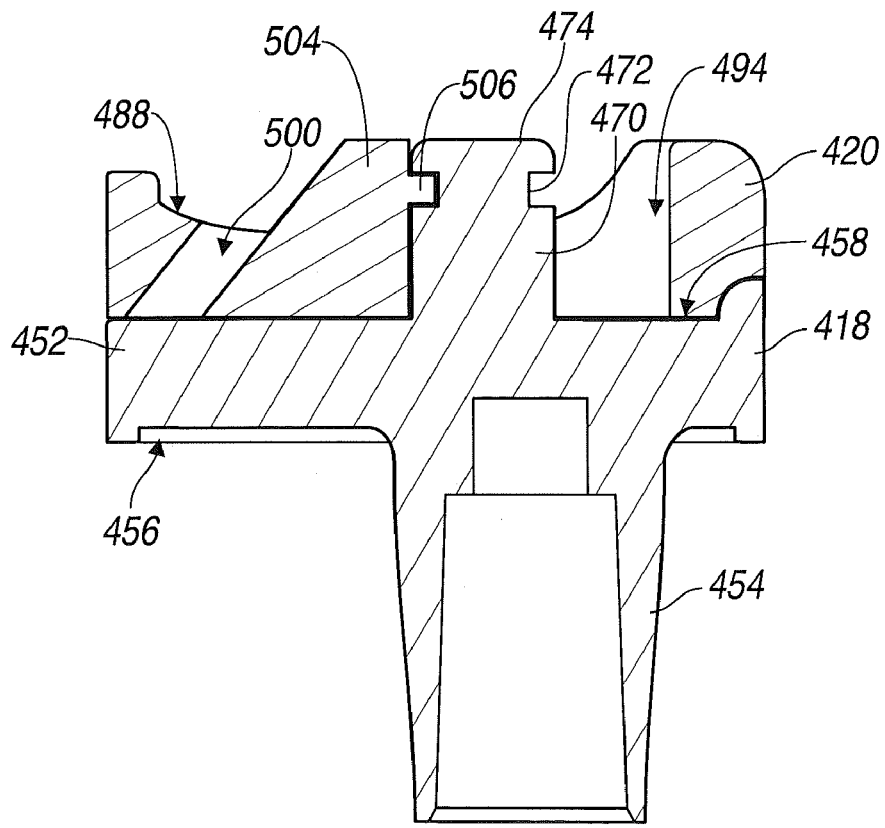
FIG. 40 is a cross-sectional view of the tibial bearing and tibial tray taken along line 39-39 of FIG. 38 and illustrating the tibial bearing advanced in an anterior direction.

With reference to FIGS. 38-40, the tibial component 418 will be further described. The tibial component 418 can be adapted to be secured to the proximal end of the tibia 12 after the tibia 12 has been resected in a manner known in the art. The tibial component 418 can include a platform-like tibial tray 452 having an inferiorly extending tibial stem 454. The tibial stem 454 can be adapted to be received in a corresponding opening made by the surgeon in the longitudinal center of the tibia 12. The tibial tray 452 can have a generally planar inferior bone engaging surface 456 and a superior bearing engaging surface 458. The inferior bone engaging surface 456 can have a porous coating for facilitating bony ingrowth.

A superiorly extending post 470 can be centrally formed on the tibial tray 452. A groove 472 can be formed annularly around the superiorly extending post 470. In one example, the groove 472 can be located generally near a terminal end 474 of the superiorly extending post 470. As will be described in greater detail, the groove 472 can be arranged to selectively locate anti-luxation features of the tibial bearing 420 and a selected yoke assembly from the kit of yoke assemblies 422 in an assembled position.

A passage 482 can be formed in the tibial tray 452 that generally extends to the tibial stem 454. The passage 482 can be arranged for accepting a fastener or set screw (not specifically shown) for cooperating with various components (such as stems and/or adapters) that can be coupled to the tibial stem 454. Examples of such stems and adapters may be provided by the Vanguard Complete Knee System manufactured by Biomet Manufacturing Corp. of Warsaw, Ind. A tab 484 can extend generally upright from the superior bearing engaging surface 458 of the tibial tray 452 for nesting into a portion of the tibial bearing 420 as will be described.

The superior surface 458 can be substantially smooth, such that the tibial bearing 420 may rest thereon. The tibial component 418 can be formed from cobalt-chromium molybdenum or any other suitable biocompatible material.

With continued reference to FIGS. 38-40, the tibial bearing 420 will be described in greater detail. The tibial bearing 420 can generally include a superior bearing surface 488 including a first bearing portion 490 and a second bearing portion 492. The first and second bearing portions 490 and 492 are configured to substantially mate with and provide an articulating surface to the first and second femoral bearing surfaces 430 and 432 (FIG. 38) of the femoral component 416. Formed between the first and second bearing portions 490 and 492 is an opening 494. The tibial bearing 420 can have a flat or substantially flat inferior anterior surface 496. A notch 497 can be formed into the inferior surface 496. A first keyway 500 can be formed in the tibial bearing 420. In one example, the first keyway 500 can be angled in a generally posterior direction from the superior bearing surface 488 to the inferior surface 496 (see FIG. 40). A superiorly extending protrusion 504 can be included on the tibial bearing 420. The superiorly extending protrusion 504 can include a first anti-luxation ring 506 that has a finger 508. The finger 508 can be generally in the form of a half or partial cylinder. The tibial bearing 420 can be formed from a surgical grade, low friction, low wearing plastic, such as UHMWPE or other suitable material.

With reference now to FIGS. 38 and 41-46, a first yoke assembly 509 of the kit of yoke assemblies 422 will be described in greater detail. The first yoke assembly 509 can generally comprise a first yoke 510 and an axle post assembly 512 having an axle post or shaft 513, a first axle post 514 and a second axle post 516. The axle post assembly 512 can extend generally along an axis 517. The first yoke 510 can generally comprise a yoke body 518 having a superior portion 520, an inferior portion 522 and an intermediate connecting portion 524. A second keyway 526 can be formed generally between the axle post assembly 512 and the inferior portion 522. An axle passage 527 can be formed in the yoke body 518 along the axis 517. The inferior portion 522 can include a second anti-luxation ring 528 that has a finger 530. The finger 530 can be in the form of a half or partial cylinder. The first yoke 510 can be formed of cobalt-chromium molybdenum or other suitable biocompatible material including non-metallic biocompatible material, such as PEEK and/or UHMWPE.

The axle post assembly 512 can comprise a second hinge portion 534 (FIG. 46) that selectively engages the first hinge portion 444 in an assembled position. The axle shaft 513 (FIG. 38) of the axle post assembly 512 can comprise threaded portions 540 and a gear 542. The threaded portions 540 can be threadably connected to complementary threads 544 formed around an inner diameter of the first and second axle posts 514 and 516. In one example, the threaded portions 540 can be threaded in a direction, such that rotation of the axle post 513 in a first direction causes both of the axle posts 514 and 516 to advance linearly outwardly (to the position shown in FIG. 46). Similarly, rotation of the axle post 513 in an opposite direction will cause the threaded portions 540 to threadably mate with the threads 544 and cause the axle posts 514 and 516 to retract inwardly toward each other (to the position shown in FIG. 45).

Figure 44:
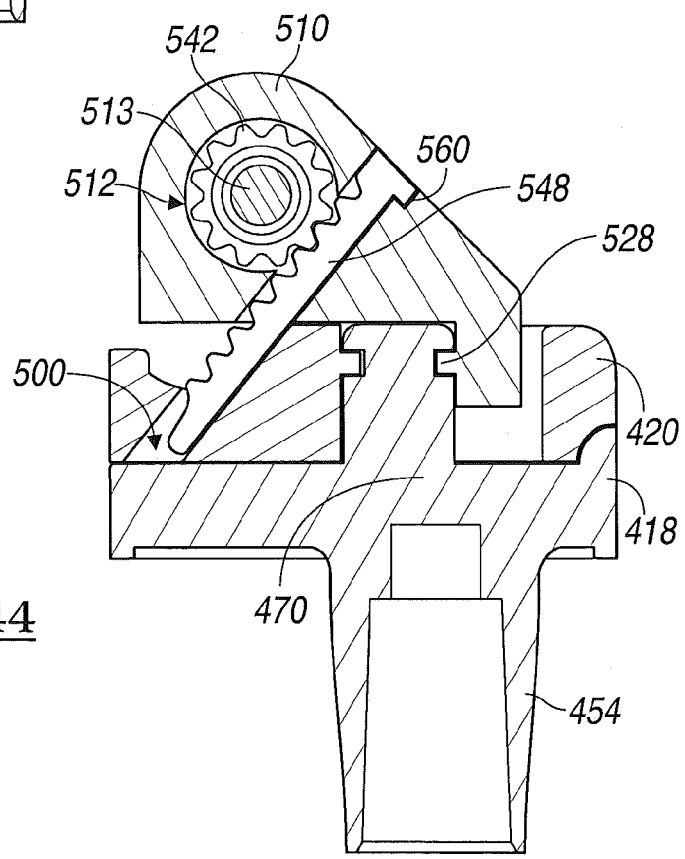

A key 548 can be advanced into the second keyway 526 of the first yoke 510 (see FIGS. 43-46) to cause expansion or retraction of the axle posts relative to the axle passage 527 in the yoke body 518. The key 548 can include a toothed portion or gear 550 formed along a key body 552 having a distal tip 554 and a proximal head 556. As can be appreciated, the gear 550 of the key 552 can meshingly engage the gear 542 provided on the axle shaft 513 to impart rotational motion of the axle post 513 around its longitudinal axis 558. The respective threaded portions 540 of the axle shaft 513 and the threaded portions 544 of the axle posts 514 and 516 can threadably cooperate to expand the axle posts 514 and 516 outwardly upon linear advancement of the key 548 into the second keyway 526. The head 556 can suitably nest into a countersink 560 formed on the yoke body 518 in an assembled position (see FIG. 44). Notably, in the assembled position, as shown in FIG. 44, the first key 552 provides a locked relationship with the axle post assembly 512, such that retraction of the axle posts 514 and 516 (e.g., in a direction toward each other) is precluded. Explained differently, the axle posts 514 and 516 are locked in the outwardly expanded position (FIG. 56) with the first key 548 in the assembled position (FIG. 44).

With specific reference now to FIGS. 39 and 40, assembly of the tibial bearing 420 relative to the tibial component 418 will be described. At the outset, the inferior surface 496 of the tibial bearing 420 is positioned onto the superior surface 458 of the tibial component 418 as shown in FIG. 39. As illustrated, the tibial bearing 420 is located such that the superiorly extending protrusion 504 is positioned such that the anti-luxation ring 506 is located posteriorly relative to the groove 472 on the superiorly extending post 470 on the tibial component 418. Next, the tibial bearing 420 is slidably advanced anteriorly (in a direction rightward as viewed from FIGS. 39-40), such that the first anti-luxation ring 506 is located into the groove 472. In one example, the tab 484 on the tibial component 418 can locate into the notch 497 of the tibial bearing 420. Other configurations are contemplated.

Figure 41:
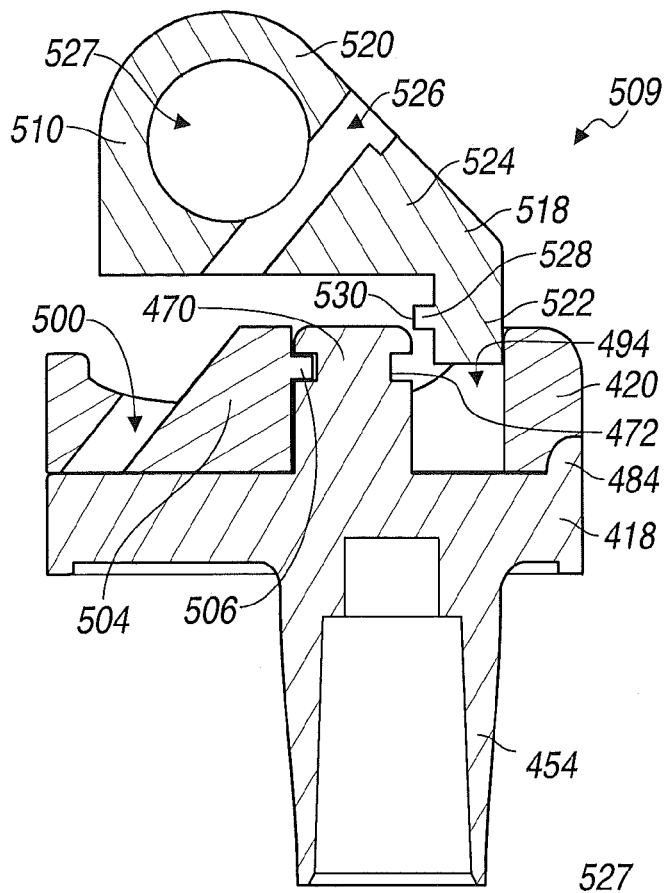
FIG. 41 is the cross-sectional view of the tibial bearing and tibial tray of FIG. 40 and shown with a yoke initially positioned proximate to an opening in the tibial bearing.
Figure 42:
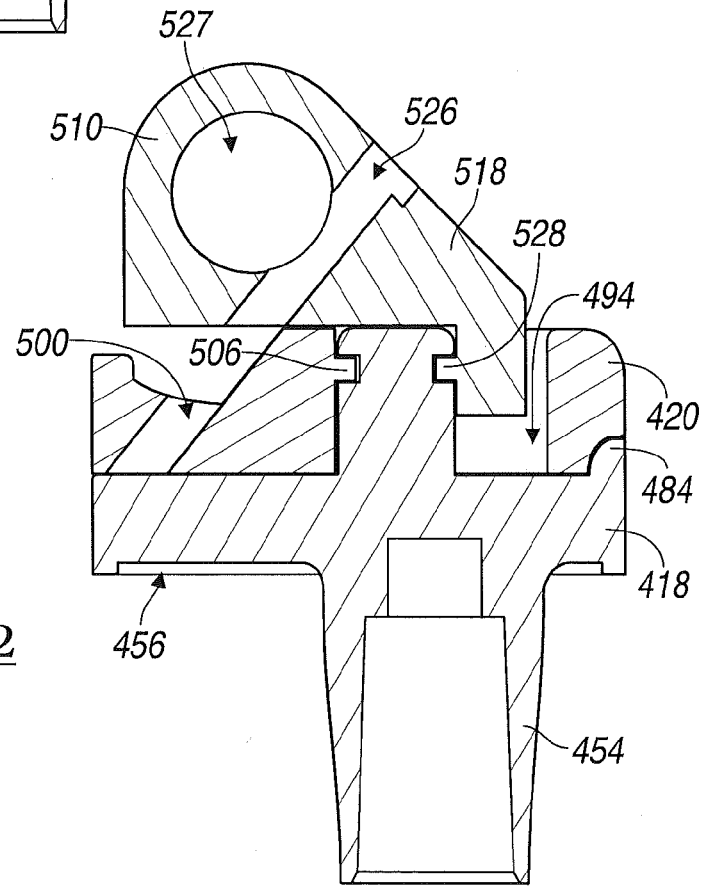
FIG. 42 is the cross-sectional view of the yoke, tibial bearing and tibial tray of FIG. 41 and shown with the yoke advanced in an inferior direction and moved slightly posterior in an engaged position with a post of the tibial tray.
Figure 43:
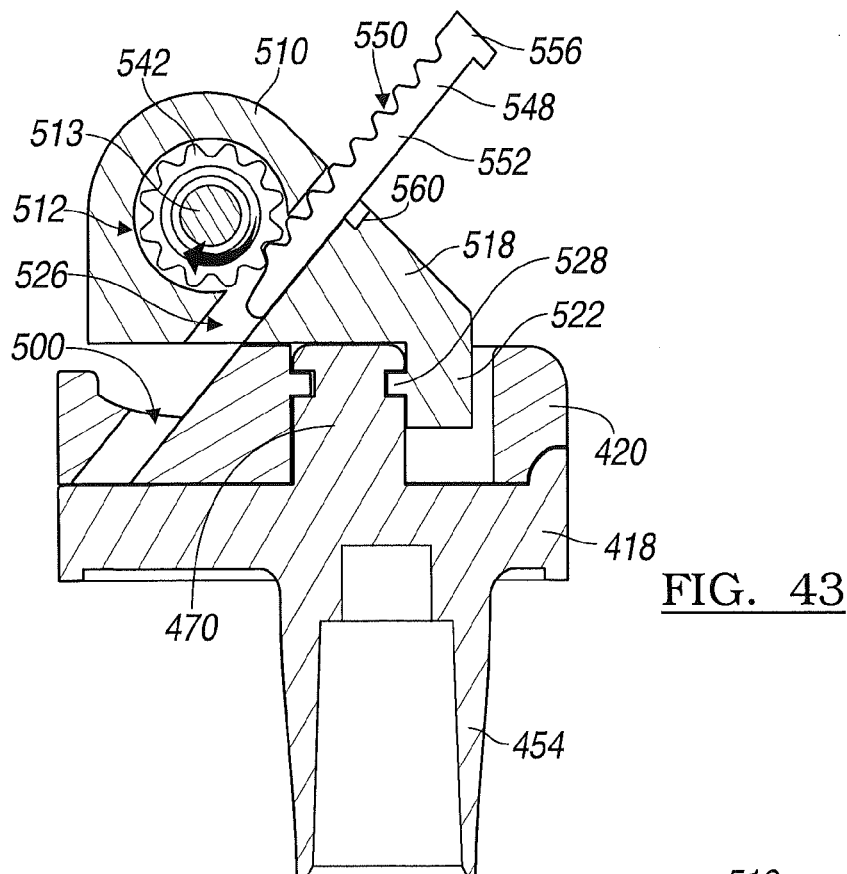
FIGS. 43 and 44 are cross-sectional views of a yoke assembly, the tibial bearing and tibial tray illustrating an assembly sequence where a key is advanced into a passage on the yoke and engages an axle assembly provided in the yoke.

Once the desired yoke assembly is selected from the kit of yoke assemblies 422 depending upon the level of constraint that is desired, the yoke is positioned relative to the tibial bearing 420. For purposes of discussion, the first yoke assembly 509 will be described as illustrated in FIGS. 41 and 42, however, it is appreciated that positioning of other yoke assemblies relative to the tibial bearing 420 and the tibial component 418 will be carried out similarly. The inferior portion 522 of the yoke body 518 is initially partially advanced into the opening 494 provided on the tibial bearing 420 and between the post 470.

Once the second anti-luxation ring 528 is aligned with the groove 472 of the superiorly extending post 470, the yoke body 518 is advanced generally posterior (in a direction leftward as viewed from FIGS. 41-42) such that the second anti-luxation ring 528 locates into the groove 472 as illustrated in FIG. 42. Notably, the interaction of the respective first and second anti-luxation rings 506 and 528 substantially inhibits upward (superior) movement of either of the yoke body 518 or the tibial bearing 420. However, in the position shown in FIG. 42, the yoke body 518 is essentially free to move anteriorly and the tibial bearing 420 is free to move posteriorly.

Advancement of the first key 548 through the second keyway 526 of the yoke body 518 and then the first keyway 500 of the tibial bearing 420 (FIGS. 43 and 44), couples the first and second anti-luxation rings 506 and 528 into a fixed position relative to each other and therefore to a fixed position within the groove 472 of the superiorly extending post 470. Once the first key 548 is inserted to the assembled position (FIG. 44), the yoke body 518 is inhibited from anterior movement and the tibial bearing 420 is inhibited from posterior movement. Additionally, the tab 484 nests into the notch 497 in the bearing 420. In other examples, the notch 497 and tab 484 may not be included and the bearing 420 is free to rotate on the tray 418.

Figure 47:
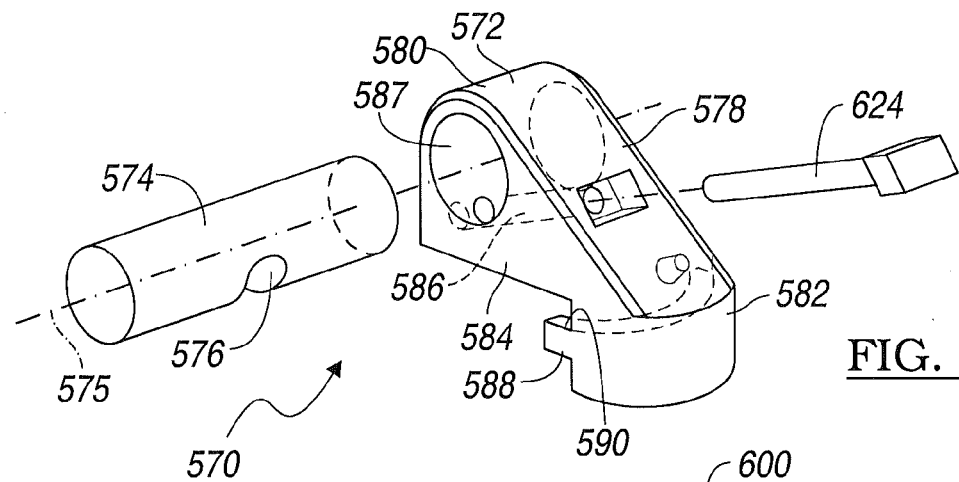
FIG. 47 is a yoke assembly constructed in accordance to additional features of the present teachings.
Figure 48:
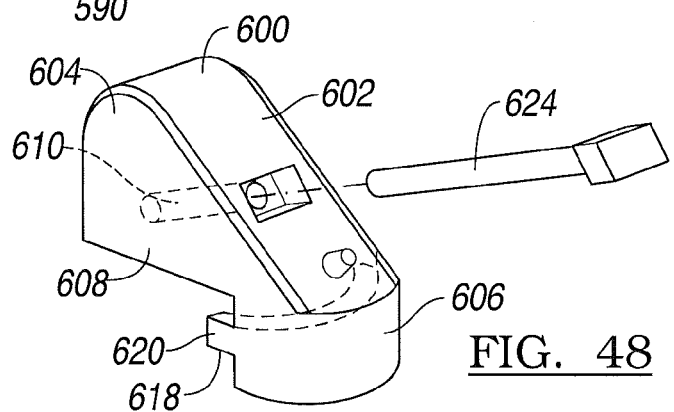
FIG. 48 is a yoke constructed in accordance to still other features of the present teachings.

Turning now to FIGS. 47 and 48, additional yokes of the kit of yoke assemblies 422 and constructed in accordance to other features of the present teachings will now be described. As illustrated in FIG. 47, a second yoke assembly 570 can generally comprise a second yoke 572 and an axle shaft 574. The axle shaft 574 is a single piece or unitary unit that extends along an axis 575 and includes a notch 576. The second yoke 572 can generally comprise a yoke body 578 having a superior portion 580, an inferior portion 582 and an intermediate connecting portion 584. A keyway 586 can be formed generally between the axle shaft 574 and the inferior portion 582. An axle passage 587 can be formed in the yoke body 578. The inferior portion 582 can include an anti-luxation ring 588 that has a finger 590. The finger 590 can be in the form of a half or partial cylinder. The second yoke 572 can be formed of cobalt-chromium molybdenum or other suitable biocompatible material, including non-metallic biocompatible material, such as PEEK and/or UHMWPE.

As illustrated in FIG. 48, a third yoke 600 can be used when it is not necessary to provide an axle that couples with a femoral component. For example, the third yoke 600 can be used in a posterior stabilized knee. In such an example, the third yoke 600 can cooperate with the femoral component 416' (FIG. 51) having a cam engaging surface 601. The third yoke 600 can generally include a yoke body 602 having a superior portion 604, an inferior portion 606 and an intermediate connecting portion 608. A keyway 610 can be formed generally through the intermediate connecting portion 608. The inferior portion 606 can include an anti-luxation ring 618 that has a finger 620. The finger 620 can be in the form of a half or partial cylinder. The third yoke 600 can be formed of cobalt-chromium molybdenum or other suitable biocompatible material, including non-metallic biocompatible material, such as PEEK and/or UHMWPE.

Both of the second and third yokes 572 and 600 can cooperate with a second key 624 that locks the respective yokes 570 or 600 to the tibial bearing 420. The second key 624 can be linearly advanced through either of the keyways 586 or 610 similar to described above with respect to the first key 548 cooperating with the first yoke 510. The second key 624 however does not include a gear or other feature that imparts motion onto the axle. In the example shown in FIG. 47, the second key 624 locates into the notch 576 of the solid axle shaft 574 to inhibit lateral motion of the axle shaft 574 through the passage 587. During assembly, the axle shaft 574 can be passed through sidewalls of a femoral component, such as the sidewalls 440 and 442 illustrated in FIG. 38. In one example, instead of the bushings 441 and 443 identified on the femoral component 416, openings can be formed through the sidewalls 440 and 442 for receiving the axle shaft 574. In the example shown in FIG. 48, the second key 624 can be passed through the keyway 610 to lock the third yoke 600 relative to the tibial bearing 420 and tibial component 418. When using the third yoke 600 illustrated in FIG. 48, the surgeon can incorporate a yoke that does not require coupling relative to the femoral component (such as the femoral component 416'). As can be appreciated, the kit 412 can be used by a surgeon to intraoperatively select various components depending on the level of constraint desired. For example, in some instances, it may be desirable to intraoperatively select either a hinged knee configuration or a posterior stabilized knee configuration. In one exemplary sequence, a femoral component 416, 416' can be implanted. A tibial tray 418 can be implanted. The femoral component 416, 416' and the tibial tray 418 can then be located relative to each other such as by hingedly coupling as described above, or locating a third yoke 600 relative to the femoral component 416' in a posterior stabilized knee configuration.

Figure 49:
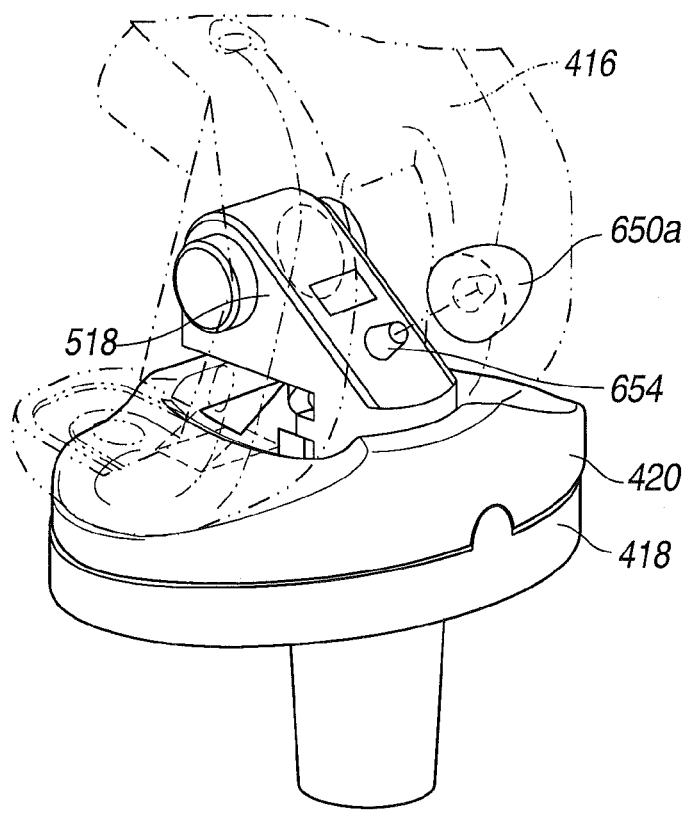
FIG. 49 is an anterior perspective view of the knee joint prosthesis system of FIG. 1 shown with the femoral component in phantom and illustrating a hyper-extension bumper shown in exploded view.
Figure 50:
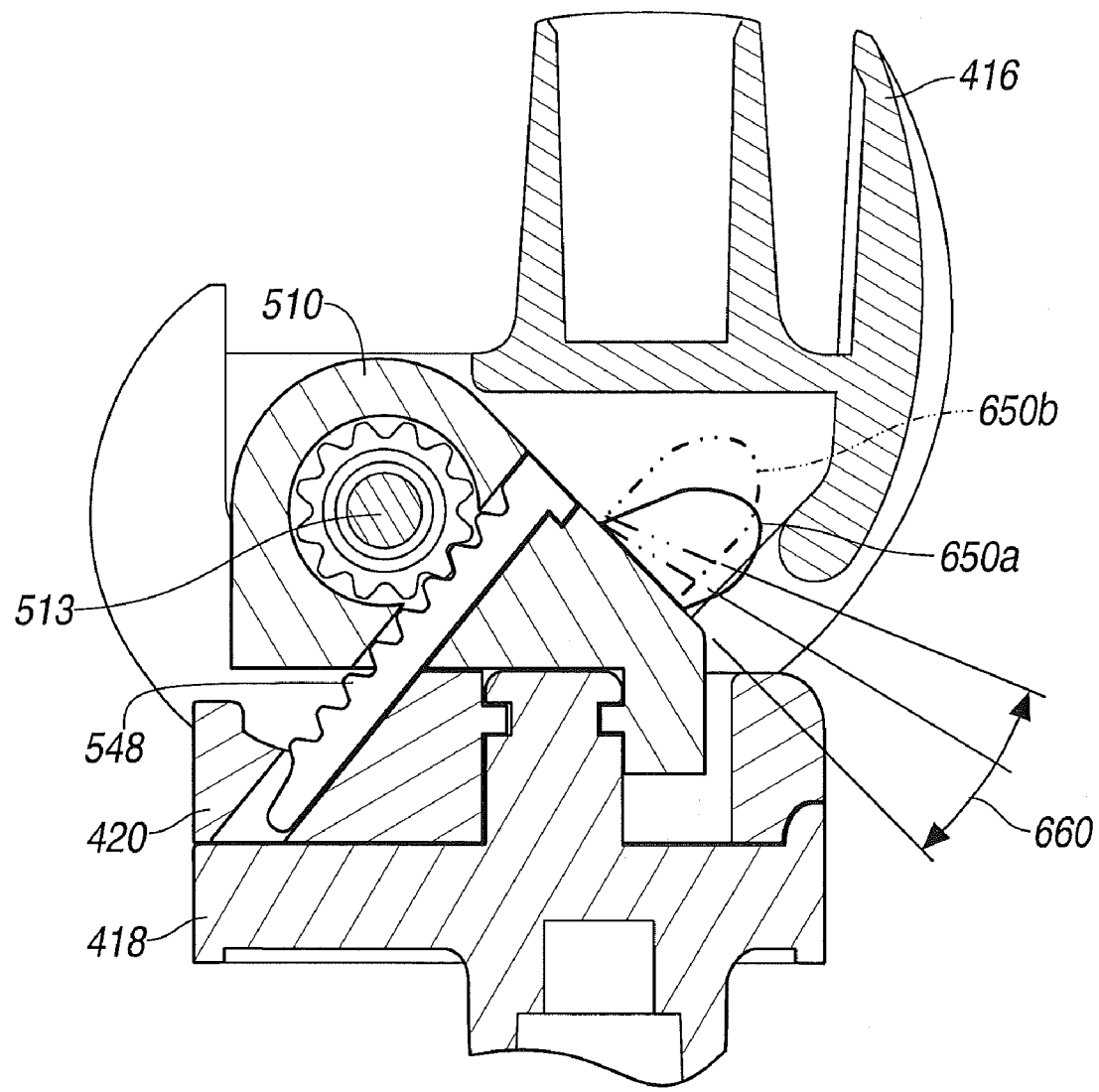
FIG. 50 is a cross-sectional view of the knee joint prosthesis system illustrating various hyper-extension bumpers cooperating between the femoral component and yoke according to various features.

Turning now to FIG. 49, a hyper-extension bumper 650A selected from a kit of hyper-extension bumpers 652 illustrated in FIG. 51 will be described according to one example. In general, the kit of hyper-extension bumpers 652 can generally include a series of hyper-extension bumpers 650A, 650B, 650C, 650D, 650E and 650F. Each of the hyper-extension bumpers can provide a different configuration that corresponds to a different degree of allowed hyper-extension of the femoral component 416. In this way, a surgeon can select any of the hyper-extension bumpers of the kit 652 depending upon the desired allowed rotational limit of the femoral component. In the particular example shown, the hyper-extension bumper 650A is shown coupled to a nub 654 extending from the first yoke body 518 with the understanding that the hyper-extension bumper 650A can be alternately configured for attachment to the femoral component 416 instead of the first yoke body 518. As illustrated in FIG. 50, depending on the hyper-extension bumper selected, such as the hyper-extension bumper 650A or the hyper-extension bumper 650B shown in phantom, the femoral component is permitted to rotate to different maximum allowable degrees of flexion until the femoral component 416, hyper-extension bumper 650A and yoke body 518 all touch. An exemplary range of maximum allowable rotation is identified by angle 660 and may be generally 5° in either direction.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthesis system for replacing a knee joint between a femur and a tibia, the prosthesis system comprising:
   a femoral component including a first condylar portion, a second condylar portion, a first sidewall extending superiorly from the first condylar portion, and a second sidewall extending superiorly from the second condylar portion;
   a tibial component having a post, a bone engaging inferior surface and a bearing engaging superior surface;
   a bearing having an inferior surface that engages the bearing engaging surface and a superior femoral engaging surface, the bearing defining an opening;
   a first yoke having an inferior portion, a superior portion and a yoke keyway extending through the first yoke; and
   a first key that is removably inserted into the yoke keyway, the first key locking the first yoke relative to the bearing in an assembled position;
   wherein the bearing has a bearing keyway and wherein the first key extends through at least portions of the yoke keyway and the bearing keyway to lock the first yoke and the bearing relative to the post in the assembled position.

2. The prosthesis system of claim 1 wherein the first and second sidewalls collectively comprise a first hinge portion and wherein the superior portion of the first yoke has an axle assembly including an axle post comprising a second hinge portion that hingedly couples to the first hinge portion.

3. A prosthesis system for replacing a knee joint between a femur and a tibia, the prosthesis system comprising:
   a femoral component including a first condylar portion, a second condylar portion, a first sidewall extending superiorly from the first condylar portion, a second sidewall extending superiorly from the second condylar portion, the first and second sidewalls collectively comprising a first hinge portion;
   a tibial component having a bone engaging inferior surface and a bearing engaging superior surface;
   a bearing having an inferior surface that engages the bearing engaging surface and a superior femoral engaging surface, the bearing defining an opening;
   a first yoke having an inferior portion, a superior portion and a yoke keyway extending through the first yoke, the superior portion having an axle assembly that comprises a second hinge portion that hingedly couples to the first hinge portion, the axle assembly including at least one axle post having a first engaging portion thereon;
   a first key that is removably inserted into the yoke keyway, the first key having a second engaging portion thereon that interacts with the first engaging portion causing the at least one axle post to be in locking engagement with the first hinge portion in an assembled position; and
   wherein the axle assembly further comprises a first and a second axle post that both meshingly interact with the second engaging portion of the key and advance respectively outwardly into locking engagement with the first hinge portion upon advancement of the first key into the yoke keyway.

4. The prosthesis system of claim 3 wherein the first engaging portion includes first threads formed on both of the first and second axle posts.

5. The prosthesis system of claim 4 wherein the axle assembly further comprises an axle shaft that is threadably connected to both of the first threads of the first and second axle posts, wherein rotation of the axle shaft causes the first and second axle posts to threadably interface with the axle shaft and collectively advance inwardly or outwardly based on the rotation.

6. The prosthesis system of claim 5, further comprising a first gear on the axle shaft that meshingly engages a second gear provided on the second engaging portion of the first key.

7. The prosthesis system of claim 6 wherein the first gear rotates upon linear advancement of the first key into the yoke keyway.

8. The prosthesis system of claim 3 wherein in the assembled position the axle post extends a distance that is greater than a distance between the first and second sidewalls of the femoral component.

9. The prosthesis system of claim 3, further comprising a hyper-extension stop that selectively couples with one of the femoral component and the first yoke and abuts the other of the femoral component and the first yoke during flexion of the femoral component about an axis defined by the first hinge portion and controls amount of hyper-extension of the femoral component relative to the tibial component.

10. A prosthesis system for replacing a knee joint between a femur and a tibia, the prosthesis system comprising:
- a femoral component including a first condylar portion, a second condylar portion, a first sidewall extending superiorly from the first condylar portion, a second sidewall extending superiorly from the second condylar portion, the first and second sidewalls collectively comprising a first hinge portion;
- a tibial component having a bone engaging inferior surface and a bearing engaging superior surface;
- a bearing having an inferior surface that engages the bearing engaging surface and a superior femoral engaging surface, the bearing defining an opening;
- a first yoke having an inferior portion, a superior portion and a yoke keyway extending through the first yoke, the superior portion having an axle assembly that comprises a second hinge portion that hingedly couples to the first hinge portion, the axle assembly including at least one axle post having a first engaging portion thereon;
- a first key that is removably inserted into the yoke keyway, the first key having a second engaging portion thereon that interacts with the first engaging portion causing the at least one axle post to be in locking engagement with the first hinge portion in an assembled position;
- wherein the tibial component has a superiorly extending post including an annular groove and that passes through the opening in the bearing in the assembled position, wherein the bearing includes a first finger that selectively locates into the annular groove in the assembled position.

11. The prosthesis system of claim 10 wherein the first yoke includes a second finger that selectively and concurrently locates into the annular groove with the first finger in the assembled position.

12. The prosthesis system of claim 11 wherein the first finger protrudes in an anterior direction and the second finger protrudes in a posterior direction.

13. The prosthesis system of claim 11 wherein the bearing defines a bearing keyway, wherein the first key is advanced into the bearing keyway subsequent to being inserted into the yoke keyway, the first key inhibiting anterior motion of the first yoke and posterior motion of the bearing while maintaining location of the first and second fingers in the groove of the post.

14. A prosthesis system of claim 3, further comprising:
- a second yoke that is selectively and alternatively coupled to the first hinge portion, the second yoke having a solid axle that extends through the second yoke and at least partially through the first hinge portion; and
- a second key that is selectively and alternatively inserted through a passage in the second yoke and a bearing passage defined through the bearing.

* * * * *

UNITED STATES PATENT AND TRADEMARK OFFICE
CERTIFICATE OF CORRECTION

PATENT NO. : 8,328,873 B2
APPLICATION NO. : 12/729852
DATED : December 11, 2012
INVENTOR(S) : Robert Metzger et al.

It is certified that error appears in the above-identified patent and that said Letters Patent is hereby corrected as shown below:

On the Title Page
Item (57), Abstract, Line 11, After "inferior" insert --surface--.
Item (57), Abstract, Line 14, After "extending" delete "through the".

In the Specification
Column 1, Line 29, Delete "prosthesis" and insert --prostheses--.
Column 2, Line 15, Delete "through the".
Column 7, Line 2, Delete "prosthesis" and insert --prostheses--.
Column 9, Line 20, Delete "bearing tibial bearing 20" and insert --rotating tibial bearing 20--.

In the Claims
Column 18, Line 20-23, Claim 1, should read:

and a yoke keyway extending through the first yoke;
an axle associated with the first yoke, the first
      sidewall and the second sidewall a first key that is removably inserted into the yoke keyway,
  wherein advancement of the first key into the yoke keyway
causes the axle to move into locking engagement with at least
      one of the first and second sidewall,
the first key locking the first yoke relative to the bearing
in an assembled position;

Signed and Sealed this
Twenty-fourth Day of March, 2015

Michelle K. Lee
*Director of the United States Patent and Trademark Office*